(12) United States Patent
Brammer et al.

(10) Patent No.: US 12,128,179 B2
(45) Date of Patent: Oct. 29, 2024

(54) AEROSOL DELIVERY DEVICE INCLUDING A BUBBLE JET HEAD AND RELATED METHOD

(71) Applicant: RAI Strategic Holdings, Inc., Winston-Salem, NC (US)

(72) Inventors: David Allan Brammer, Smyrna, GA (US); David Jackson, Gainesville, GA (US); Nigel Flynn, Flowery Branch, GA (US); Eric T. Hunt, Pfafftown, NC (US); Stephen Benson Sears, Siler City, NC (US); Dennis Lee Potter, Kernersville, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 17/895,867

(22) Filed: Aug. 25, 2022

(65) Prior Publication Data

US 2022/0401669 A1 Dec. 22, 2022

Related U.S. Application Data

(63) Continuation of application No. 16/723,032, filed on Dec. 20, 2019, now Pat. No. 11,458,265, which is a
(Continued)

(51) Int. Cl.
*A61M 15/02* (2006.01)
*A24F 40/10* (2020.01)
(Continued)

(52) U.S. Cl.
CPC .......... *A61M 15/025* (2014.02); *A24F 40/42* (2020.01); *A24F 40/44* (2020.01); *A24F 40/48* (2020.01);
(Continued)

(58) Field of Classification Search
CPC .......... A24F 40/10; A24F 40/40; A24F 40/42; A24F 40/44; A24F 40/46; A24F 40/48;
(Continued)

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

ImTech; I-Jet Fluid Jetting and Printing Tool Data Sheet; website visited Jul. 26, 2014 http:/imtech-or.com/wp-content/uploads/2013/03/IJet-IIS.pdf.
(Continued)

*Primary Examiner* — Justine R Yu
*Assistant Examiner* — Alexander Morales
(74) *Attorney, Agent, or Firm* — Womble Bond Dickinson (US) LLP

(57) ABSTRACT

The present disclosure relates to aerosol delivery devices. The aerosol delivery devices include mechanisms configured to deliver an aerosol precursor composition from a reservoir to an atomizer including a vaporization heating element to produce a vapor. For example, a bubble jet head may be configured to dispense the aerosol precursor composition to the atomizer. The bubble jet head may be fixedly coupled to the atomizer. The bubble jet head may include a precursor inlet, an ejection heating element, and a precursor nozzle. The atomizer may include a vaporization heating element.

22 Claims, 30 Drawing Sheets

Related U.S. Application Data continuation of application No. 14/524,778, filed on Oct. 27, 2014, now Pat. No. 10,548,351.

(60) Provisional application No. 61/897,917, filed on Oct. 31, 2013.

(51) Int. Cl.

| | | |
|---|---|---|
| *A24F 40/42* | (2020.01) | |
| *A24F 40/44* | (2020.01) | |
| *A24F 40/48* | (2020.01) | |
| *A24F 40/485* | (2020.01) | |
| *A24F 40/50* | (2020.01) | |
| *A61M 11/00* | (2006.01) | |
| *A61M 11/04* | (2006.01) | |
| *A61M 15/06* | (2006.01) | |
| *A61M 16/00* | (2006.01) | |
| *F24H 1/00* | (2022.01) | |
| *H05B 3/02* | (2006.01) | |

(52) U.S. Cl.
 CPC ............ *A24F 40/485* (2020.01); *A24F 40/50* (2020.01); *A61M 11/007* (2014.02); *A61M 15/06* (2013.01); *F24H 1/0018* (2013.01); *H05B 3/02* (2013.01); *A24F 40/10* (2020.01); *A61M 11/042* (2014.02); *A61M 2016/0024* (2013.01); *A61M 2205/8206* (2013.01)

(58) Field of Classification Search
 CPC ..... A24F 40/485; A24F 40/50; A61M 11/007; A61M 11/042; A61M 15/0001; A61M 15/025; A61M 15/06; A61M 2016/0018; A61M 2016/0024; A61M 2205/8206; A61M 11/041; A61M 11/044; F24H 1/0018; H05B 3/02; B05B 1/24; B05B 7/16; B05B 9/002
 USPC ........... 604/134–136; 239/13, 128, 133–136; 131/194
 See application file for complete search history.

(56) References Cited

U.S. PATENT DOCUMENTS

| | | | |
|---|---|---|---|
| 2,104,266 | A | 1/1938 | McCormick |
| 3,200,819 | A | 4/1963 | Gilbert |
| 4,284,089 | A | 8/1981 | Ray |
| 4,303,083 | A | 12/1981 | Burruss, Jr. |
| 4,735,217 | A | 4/1988 | Gerth et al. |
| 4,771,295 | A | 9/1988 | Baker et al. |
| 4,793,365 | A | 12/1988 | Sensabaugh, Jr. et al. |
| 4,848,374 | A | 7/1989 | Chard et al. |
| 4,907,606 | A | 3/1990 | Lilja et al. |
| 4,911,181 | A | 3/1990 | Vromen et al. |
| 4,922,901 | A | 5/1990 | Brooks et al. |
| 4,945,931 | A | 8/1990 | Gori |
| 4,947,874 | A | 8/1990 | Brooks et al. |
| 4,947,875 | A | 8/1990 | Brooks et al. |
| 4,986,286 | A | 1/1991 | Roberts et al. |
| 4,990,939 | A | 2/1991 | Sekiya et al. |
| 5,019,122 | A | 5/1991 | Clearman et al. |
| 5,042,510 | A | 8/1991 | Curtiss et al. |
| 5,060,671 | A | 10/1991 | Counts et al. |
| 5,085,638 | A | 2/1992 | Farbstein et al. |
| 5,093,894 | A | 3/1992 | Deevi et al. |
| 5,101,839 | A | 4/1992 | Jakob et al. |
| 5,144,962 | A | 8/1992 | Counts et al. |
| 5,154,192 | A | 10/1992 | Sprinkel et al. |
| 5,224,498 | A | 7/1993 | Deevi et al. |
| 5,228,460 | A | 7/1993 | Sprinkel et al. |
| 5,249,586 | A | 10/1993 | Morgan et al. |
| 5,261,424 | A | 11/1993 | Sprinkel, Jr. |
| 5,322,075 | A | 6/1994 | Deevi et al. |
| 5,353,813 | A | 10/1994 | Deevi et al. |
| 5,369,723 | A | 11/1994 | Counts et al. |
| 5,372,148 | A | 12/1994 | McCafferty et al. |
| 5,388,574 | A | 2/1995 | Ingebrethsen et al. |
| 5,408,574 | A | 4/1995 | Deevi et al. |
| 5,468,936 | A | 11/1995 | Deevi et al. |
| 5,498,850 | A | 3/1996 | Das |
| 5,515,842 | A | 5/1996 | Ramseyer et al. |
| 5,530,225 | A | 6/1996 | Hajaligol |
| 5,564,442 | A | 10/1996 | MacDonald et al. |
| 5,573,692 | A | 11/1996 | Das et al. |
| 5,591,368 | A | 1/1997 | Fleischhauer et al. |
| 5,649,554 | A | 7/1997 | Sprinkel et al. |
| 5,659,656 | A | 8/1997 | Das |
| 5,665,262 | A | 9/1997 | Hajaligol et al. |
| 5,666,977 | A | 9/1997 | Higgins et al. |
| 5,687,746 | A | 11/1997 | Rose et al. |
| 5,703,633 | A | 12/1997 | Gehrer et al. |
| 5,708,465 | A | 1/1998 | Morita et al. |
| 5,726,421 | A | 3/1998 | Fleischhauer et al. |
| 5,727,571 | A | 3/1998 | Meiring et al. |
| 5,743,251 | A | 4/1998 | Howell et al. |
| 5,745,137 | A | 4/1998 | Scheffelin et al. |
| 5,799,663 | A | 9/1998 | Gross et al. |
| 5,819,756 | A | 10/1998 | Mielordt |
| 5,865,185 | A | 2/1999 | Collins et al. |
| 5,865,186 | A | 2/1999 | Volsey, II |
| 5,878,752 | A | 3/1999 | Adams et al. |
| 5,894,841 | A | 4/1999 | Voges |
| 5,934,289 | A | 8/1999 | Watkins et al. |
| 5,954,979 | A | 9/1999 | Counts et al. |
| 5,967,148 | A | 10/1999 | Harris et al. |
| 5,970,974 | A | 10/1999 | Van Der Linden et al. |
| 6,040,560 | A | 3/2000 | Fleischhauer et al. |
| 6,053,176 | A | 4/2000 | Adams et al. |
| 6,089,857 | A | 7/2000 | Matsuura et al. |
| 6,095,153 | A | 8/2000 | Kessler et al. |
| 6,125,853 | A | 10/2000 | Susa et al. |
| 6,155,268 | A | 12/2000 | Takeuchi |
| 6,164,287 | A | 12/2000 | White |
| 6,196,218 | B1 | 3/2001 | Voges |
| 6,196,219 | B1 | 3/2001 | Hess et al. |
| 6,234,167 | B1 | 5/2001 | Cox et al. |
| 6,501,052 | B2 | 12/2002 | Cox et al. |
| 6,601,776 | B1 | 8/2003 | Oljaca et al. |
| 6,615,840 | B1 | 9/2003 | Fournier et al. |
| 6,688,313 | B2 | 2/2004 | Wrenn et al. |
| 6,772,756 | B2 | 8/2004 | Shayan |
| 6,803,545 | B2 | 10/2004 | Blake et al. |
| 6,810,883 | B2 | 11/2004 | Felter et al. |
| 6,854,461 | B2 | 2/2005 | Nichols |
| 6,854,470 | B1 | 2/2005 | Pu |
| 7,117,867 | B2 | 10/2006 | Cox et al. |
| 7,131,599 | B2 | 11/2006 | Katase |
| 7,293,565 | B2 | 11/2007 | Griffin et al. |
| 7,311,503 | B2 | 12/2007 | Van Lintel et al. |
| 7,513,253 | B2 | 4/2009 | Kobayashi et al. |
| 7,775,459 | B2 | 8/2010 | Martens, III et al. |
| 7,832,410 | B2 | 11/2010 | Hon |
| 7,845,359 | B2 | 12/2010 | Montaser |
| 7,896,006 | B2 | 3/2011 | Hamano et al. |
| 8,127,772 | B2 | 3/2012 | Montaser |
| 8,156,944 | B2 | 4/2012 | Han |
| 8,314,591 | B2 | 11/2012 | Terry et al. |
| 8,365,742 | B2 | 2/2013 | Hon |
| 8,393,331 | B2 | 3/2013 | Hon |
| 8,402,976 | B2 | 3/2013 | Fernando et al. |
| 8,490,628 | B2 | 7/2013 | Hon |
| 8,499,766 | B1 | 8/2013 | Newton |
| 8,528,569 | B1 | 9/2013 | Newton |
| 8,550,069 | B2 | 10/2013 | Alelov |
| 8,689,804 | B2 | 4/2014 | Fernando et al. |
| 8,881,737 | B2 | 11/2014 | Collett et al. |
| 8,893,726 | B2 * | 11/2014 | Hon .................... H05B 3/0014 131/273 |
| 9,352,246 | B2 * | 5/2016 | Roux .................... B01B 1/005 |
| 9,484,155 | B2 | 11/2016 | Peckerar et al. |
| 10,034,988 | B2 | 7/2018 | Wensley et al. |
| 11,458,265 | B2 * | 10/2022 | Brammer ................ A24F 40/42 |

(56) References Cited

U.S. PATENT DOCUMENTS

| | | |
|---|---|---|
| 2002/0092519 A1* | 7/2002 | Davis .................. B41J 2/14016 128/200.14 |
| 2002/0146242 A1 | 10/2002 | Vieira |
| 2002/0164169 A1 | 11/2002 | Arai et al. |
| 2003/0108342 A1 | 6/2003 | Sherwood et al. |
| 2003/0226837 A1 | 12/2003 | Blake et al. |
| 2004/0017203 A1 | 1/2004 | Becker et al. |
| 2004/0021749 A1 | 2/2004 | Chou et al. |
| 2004/0081624 A1 | 4/2004 | Nguyen et al. |
| 2004/0118401 A1 | 6/2004 | Smith et al. |
| 2004/0118941 A1 | 6/2004 | Joseph et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2005/0096687 A1 | 5/2005 | Rassman et al. |
| 2005/0157578 A1 | 7/2005 | Noguchi et al. |
| 2005/0279854 A1* | 12/2005 | Martens ............. B05B 17/0646 239/34 |
| 2006/0016453 A1 | 1/2006 | Kim |
| 2006/0081239 A1 | 4/2006 | Alley et al. |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0145161 A1 | 6/2007 | Tomita et al. |
| 2007/0215167 A1 | 9/2007 | Crooks et al. |
| 2007/0250002 A1 | 10/2007 | Oliver |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0173341 A1* | 7/2009 | Reinhold ............. A61M 15/02 239/311 |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0078015 A1 | 4/2010 | Imran |
| 2010/0083956 A1* | 4/2010 | Fukumoto ............. A61M 11/003 128/200.14 |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036346 A1 | 2/2011 | Cohen et al. |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0175960 A1* | 7/2011 | Fukumoto .................. B41J 2/03 347/14 |
| 2011/0262650 A1* | 10/2011 | Lee .......................... B05B 5/001 427/457 |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0048266 A1 | 3/2012 | Alelov |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0199663 A1 | 8/2012 | Qiu |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0008457 A1 | 1/2013 | Zheng et al. |
| 2013/0037041 A1 | 2/2013 | Worm et al. |
| 2013/0056013 A1 | 3/2013 | Terry et al. |
| 2013/0081623 A1 | 4/2013 | Buchberger |
| 2013/0081625 A1 | 4/2013 | Rustad et al. |
| 2013/0081642 A1 | 4/2013 | Safari |
| 2013/0123703 A1 | 5/2013 | Shay |
| 2013/0192619 A1 | 8/2013 | Tucker et al. |
| 2013/0197475 A1 | 8/2013 | Dunn |
| 2013/0220315 A1 | 8/2013 | Conley et al. |
| 2013/0255702 A1 | 10/2013 | Griffith et al. |
| 2013/0284194 A1 | 10/2013 | Newton |
| 2013/0306084 A1 | 11/2013 | Flick |
| 2013/0319439 A1 | 12/2013 | Gorelick et al. |
| 2013/0319440 A1 | 12/2013 | Capuano |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0007863 A1 | 1/2014 | Chen |
| 2014/0060554 A1 | 3/2014 | Collett et al. |
| 2014/0060555 A1 | 3/2014 | Chang et al. |
| 2014/0069424 A1 | 3/2014 | Poston et al. |
| 2014/0076310 A1 | 3/2014 | Newton |
| 2014/0096781 A1 | 4/2014 | Sears et al. |
| 2014/0096782 A1 | 4/2014 | Ampolini et al. |
| 2014/0150783 A1 | 6/2014 | Liu |
| 2014/0270729 A1 | 9/2014 | DePiano et al. |
| 2015/0114409 A1 | 4/2015 | Brammer et al. |
| 2015/0114411 A1 | 4/2015 | Buchberger |
| 2015/0292084 A1* | 10/2015 | Glaudel ................. C23C 16/455 700/282 |
| 2015/0367013 A1* | 12/2015 | Gruenbacher ....... B41J 2/14201 239/13 |
| 2016/0037826 A1 | 2/2016 | Hearn et al. |
| 2016/0106154 A1 | 4/2016 | Lord |

FOREIGN PATENT DOCUMENTS

| | | |
|---|---|---|
| CA | 2808836 | 3/2012 |
| CN | 1541577 | 11/2004 |
| CN | 2719043 | 8/2005 |
| CN | 1753819 | 3/2006 |
| CN | 101084801 | 12/2007 |
| CN | 200983833 | 12/2007 |
| CN | 200997909 | 1/2008 |
| CN | 101116542 | 2/2008 |
| CN | 101176805 | 5/2008 |
| CN | 201064185 | 5/2008 |
| CN | 101228969 | 7/2008 |
| CN | 201379072 | 1/2010 |
| CN | 102355914 | 2/2012 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2218760 | 8/2010 |
| EP | 2 316 286 | 5/2011 |
| GB | 2099710 | 12/1982 |
| GB | 2469850 | 11/2010 |
| JP | 2000-185403 | 7/2000 |
| KR | 10-2009-0067164 | 6/2009 |
| RU | 2320374 C2 | 3/2008 |
| RU | 103281 U1 | 4/2011 |
| UZ | 02238 | 12/2002 |
| WO | WO 1995/01137 | 1/1995 |
| WO | WO 1997/48293 | 12/1997 |
| WO | WO 98/57556 | 12/1998 |
| WO | WO 2004/043175 | 5/2004 |
| WO | WO 2005/099494 | 10/2005 |
| WO | WO 2005/120614 | 12/2005 |
| WO | WO 2007/078273 | 7/2007 |

(56) References Cited

FOREIGN PATENT DOCUMENTS

| WO | WO 2007/131449 | 11/2007 |
|---|---|---|
| WO | WO 2008/043122 | 4/2008 |
| WO | WO-2009069519 A1 | 6/2009 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/091593 | 8/2010 |
| WO | WO 2010/118644 | 10/2010 |
| WO | WO 2010/140937 | 12/2010 |
| WO | WO 2011/010334 | 1/2011 |
| WO | WO-2011137453 A2 | 11/2011 |
| WO | WO 2012/026963 | 3/2012 |
| WO | WO 2012/072762 | 6/2012 |
| WO | WO 2012/100523 | 8/2012 |
| WO | WO-2012129812 A1 | 10/2012 |
| WO | WO-2013027249 A1 | 2/2013 |
| WO | WO 2013/089551 | 6/2013 |
| WO | WO 2013/128176 | 9/2013 |
| WO | WO 2013/152873 | 10/2013 |

OTHER PUBLICATIONS

International Search Report and Written Opinion of the International Searching Authority for corresponding International Application No. PCT/US2014/062815.

Hewlett-Packard Thermal Ink-Jet Print Cartridge Designer's Guide, Second Edition; pp. 13-24 (believed to be publicly available before Oct. 31, 2013 for purposes of examination).

David A Henderson; Novel Piezo Motor Enables Positive Displacement Microfluidic Pump; Presented at NSTI Nanotech 2007; 2007 New Scale Technologies, Inc. http://www.newscaletech.com/doc_downloads/Positive_Displacement_Microfluidic_Pump.pdf.

CurieJet®; Low-Power Micro Pump; Ultra Low-Power Slim Diaphragm MicroPump; document downloaded Jul. 29, 2014 http://downloads.microjet.com.tw/CurieJet/CurieJet_Micropump_Catalog%20Ver.20131220.pdf.

Electroosmotic Pump; Wikipedia; website visited Jul. 29, 2014 http://en.wikipedia.org/wiki/Electroosmotic_pump.

Mp6 Piezoelectric Diaphragm Micropump; website visited Jul. 29, 2014 http://www.servoflo.com/micropumps/mp6.html.

The Lee Company; Electro-Fluidic Systems—Pumps; website visited Jul. 29, 2014 http://www.theleeco.com/electro-fluidic-systems/pumps/pumps.cfm.

Piezoelectric Micro Pumps SDMP—Standard Series—Takasago Fluidic Systems; website visited Jul. 29, 2014 http://www.takasago-fluidics.com/products_pump/transfer/SDMP_Standard/.

AdTech Ceramics; Multi Layer Aluminum Nitride (AIN)—Chattanooga, Tennessee; website visited Jul. 29, 2014 http://www.adtechceramics.com/multi-layer-aluminum-nitride-ain.html.

Microfab Technologies; Dispensing Devices; Low Temperature Devices and High Temperature Devices; website visited Aug. 7, 2014 http://www.microfab.com/index.php?option=com_content&view=category&layout=blog&id=10&Itemid=10.

International Search Report and Written Opinion of the International Searching Authority for corresponding International Application No. PCT/US2014/062803 mailed Feb. 6, 2015.

"Combination", Oxford Dictionaries, accessed at www.en.oxforddictionaries.com on Oct. 3, 2017. (Year: 2017).

Office Action issued Oct. 20, 2023, in corresponding Chinese application No. 202111220716.9.

* cited by examiner

START

DIRECT AN AIRFLOW FROM A CONTROL BODY COMPRISING A POWER SOURCE THROUGH A CARTRIDGE COMPRISING A RESERVIOR — 2402

DISPENSE AN AEROSOL PRECURSOR COMPOSITION FROM THE RESERVIOR VIA A BUBBLE JET HEAD — 2404

HEAT THE AEROSOL PRECURSOR COMPOSITION DISPENSED FROM THE RESERVOIR BY THE BUBBLE JET HEAD WITH AN ATOMIZER — 2406

END

AEROSOL DELIVERY DEVICE INCLUDING A BUBBLE JET HEAD AND RELATED METHOD

CROSS-REFERENCE TO RELATED APPLICATIONS

This application is a continuation of U.S. application Ser. No. 16/723,032, filed Dec. 20, 2019, which is a continuation of U.S. application Ser. No. 14/524,778, filed Oct. 27, 2014, which claims the benefit of U.S. Provisional Application No. 61/897,917; filed Oct. 31, 2013, which applications are hereby incorporated by reference in their entirety in this application.

FIELD OF THE DISCLOSURE

The present disclosure relates to aerosol delivery devices, such as smoking articles; and more particularly, to aerosol delivery devices that utilize electrically generated heat for the production of aerosol (e.g., smoking articles commonly referred to as electronic cigarettes). Aerosol delivery devices including mechanisms for delivery of an aerosol precursor composition to an atomizer are provided. The smoking articles may be configured to heat an aerosol precursor, which incorporates materials made or derived from tobacco or otherwise incorporate tobacco, capable of vaporizing to form an inhalable aerosol for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. Pub. Nos. 2013/0255702 to Griffith, Jr. et al. and 2014/0096781 to Sears et al., which are incorporated herein by reference. See also, for example, the various types of smoking articles, aerosol delivery devices and electrically powered heat generating sources referenced by brand name and commercial source in U.S. patent application Ser. No. 14/170,838, filed Feb. 3, 2014, to Bless et al., which is incorporated herein by reference.

However, it may be desirable to provide aerosol delivery devices with enhanced functionality. In this regard, it may be desirable to improve delivery of an aerosol precursor composition to an atomizer.

BRIEF SUMMARY OF THE DISCLOSURE

The present disclosure relates to aerosol delivery systems. Such systems have the ability to generate aerosol as a result of heat generated by electrical power sources, and to deliver aerosol that is intended to be drawn into the mouth of a user. Of particular interest are aerosol delivery systems that provide components of tobacco in an aerosol form, such as is provided to smokers by devices commonly known or characterized as electronic cigarettes. As used herein, the term "aerosol" is meant to include vapors, gases and aerosols of a form or type suitable for human inhalation, whether or not visible, and whether or not of a form that might be considered to be "smoke-like."

Various embodiments of mechanisms for delivering an aerosol precursor composition to an atomizer are provided. These mechanisms may include bubble jet heads, as described hereinafter. As described herein, a bubble jet head is a component configured to heat a fluid (e.g., an aerosol precursor composition) to produce a bubble of vapor that applies pressure to the fluid and ejects one or more droplets of the fluid therefrom. Bubble jet heads may be defined as including an inlet (e.g., a precursor inlet), an ejection heating element, and a nozzle (e.g., a precursor nozzle), which may be housed within, or defined by, a wafer, substrate, or housing.

In one aspect an aerosol delivery device is provided. The aerosol delivery device may include a reservoir at least partially filled with an aerosol precursor composition. Further, the aerosol delivery device may include a bubble jet head in fluid communication with the reservoir. The bubble jet head may be configured to dispense the aerosol precursor composition from the reservoir. Additionally, the aerosol delivery device may include an atomizer configured to heat the aerosol precursor composition dispensed by the bubble jet head to produce an aerosol. The bubble jet head and the atomizer may be fixedly coupled to one another.

In some embodiments the aerosol delivery device may further include an outer body and a housing received within the outer body. The bubble jet head and the atomizer may be fixedly coupled to one another via the housing. The bubble jet head may be coupled to the atomizer via one or more spacers. Further, the bubble jet head and the atomizer may be electrically coupled via a flexible circuit.

In some embodiments the atomizer may include a housing, a vaporization heating element coupled to the housing, and a reinforcement member coupled to and configured to support the housing. The reinforcement member may define a cutout. The aerosol delivery device may additionally include an outer body, wherein a heating surface of the atomizer is oriented at a non-zero angle with respect to a longitudinal axis of the outer body.

In some embodiments the aerosol delivery device may include an outer body. A heating surface of the atomizer may be oriented substantially parallel to a longitudinal axis of the outer body. The bubble jet head may be configured to eject the aerosol precursor composition substantially perpendicularly to a heating surface of the atomizer. A heating surface of the atomizer may be non-planar. The heating surface of the atomizer may be substantially conical. A heating surface of the atomizer may be textured.

In some embodiments the reservoir may include a reservoir substrate configured to direct the aerosol precursor composition to the bubble jet head. The bubble jet head may be coupled to a distal end of the reservoir. The bubble jet head may be coupled to a lateral side of the reservoir. The bubble jet head and the atomizer may be positioned between the reservoir and a mouthpiece. Alternatively, the reservoir may be positioned between a mouthpiece and the atomizer and the bubble jet head. The aerosol delivery device may further include a cartridge comprising a base and a control body comprising a coupler. The base may be configured to engage the coupler to provide a mechanical and electrical connection between the cartridge and the control body.

In an additional aspect a combined dispenser and atomizer assembly is provided. The combined dispenser and atomizer assembly may include a housing, a bubble jet head including an ejection heating element configured to dispense an aerosol precursor composition from a reservoir, and an atomizer including a vaporization heating element configured to heat the aerosol precursor composition dispensed by the bubble jet head to produce an aerosol. The bubble jet head and the atomizer may be coupled to one another via the housing. The housing may be configured for receipt within an outer body of an aerosol delivery device.

In some embodiments the bubble jet head may further include a precursor inlet and a precursor nozzle. The atomizer may further include an aerosol outlet. An area of the aerosol outlet may be greater than an area of the precursor nozzle. A thermal mass of the ejection heating element may be less than a thermal mass of the vaporization heating element. The ejection heating element, the precursor nozzle, and the vaporization heating element may be axially aligned. The housing may define at least one of the precursor inlet, the precursor nozzle, and the aerosol outlet.

In an additional aspect, an aerosol delivery device is provided. The aerosol delivery device may include a reservoir at least partially filled with an aerosol precursor composition. Further, the aerosol delivery device may include a housing including a precursor inlet in fluid communication with the reservoir, an ejection heating element, and a precursor nozzle. The ejection heating element may be configured to eject the aerosol precursor composition received through the precursor inlet out through the precursor nozzle. Additionally, the aerosol delivery device may include an atomizer configured to heat the aerosol precursor composition dispensed from the housing to produce an aerosol. The ejection heating element and the atomizer may be fixedly coupled to one another.

In some embodiments the atomizer may be received within the housing, and the housing and the reservoir may be received within an outer body. In another embodiment the housing may be coupled to the atomizer via one or more spacers. The housing and the atomizer may be electrically coupled via a flexible circuit.

In some embodiments the atomizer may include an atomizer housing, a vaporization heating element coupled to the housing, and a reinforcement member coupled to and configured to support the housing. The reinforcement member may define a cutout. The aerosol delivery device may additionally include an outer body, and a heating surface of the atomizer may be oriented at a non-zero angle with respect to a longitudinal axis of the outer body. In another embodiment the heating surface of the atomizer may be oriented substantially parallel to a longitudinal axis of the outer body.

In some embodiments the precursor nozzle may be configured to eject the aerosol precursor composition substantially perpendicularly to a heating surface of the atomizer. The heating surface of the atomizer may be non-planar. The heating surface of the atomizer may be substantially conical. The heating surface of the atomizer may be textured.

In some embodiments the reservoir may include a reservoir substrate configured to direct the aerosol precursor composition to the precursor inlet. The housing may be coupled to a distal end of the reservoir. In another embodiment the housing may be coupled to a lateral side of the reservoir. The housing and the atomizer may be positioned between the reservoir and a mouthpiece. In another embodiment the reservoir may be positioned between a mouthpiece and the atomizer and the housing. The aerosol delivery device may additionally include a cartridge including a base, and a control body including a coupler. The base may be configured to engage the coupler to provide a mechanical and electrical connection between the cartridge and the control body.

In an additional aspect a combined dispenser and atomizer assembly is provided. The combined dispenser and atomizer assembly may include a housing, an ejection heating element configured to dispense an aerosol precursor composition from a reservoir, and a vaporization heating element configured to heat the aerosol precursor composition dispensed by the ejection heating element to produce an aerosol. The ejection heating element and the vaporization heating element may be received within the housing, and the housing may be configured for receipt within an outer body of an aerosol delivery device.

In some embodiments the combined dispenser and atomizer assembly may additionally include a precursor inlet, a precursor nozzle, a vaporization heating element and an aerosol outlet. An area of the aerosol outlet may be greater than an area of the precursor nozzle. A thermal mass of the ejection heating element may be less than a thermal mass of the vaporization heating element. The ejection heating element, the precursor nozzle, and the vaporization heating element may be axially aligned. The housing may define at least one of the precursor inlet, the precursor nozzle, and the aerosol outlet.

In an additional aspect a method for aerosolization in an aerosol delivery device is provided. The method may include directing an airflow from a control body including a power source through a cartridge including a reservoir. The method may additionally include dispensing an aerosol precursor composition from the reservoir via a precursor inlet, an ejection heating element, and a precursor nozzle. The method may further include heating (e.g., vaporizing) the aerosol precursor composition dispensed from the reservoir with an atomizer.

In some embodiments dispensing the aerosol precursor composition and heating the aerosol precursor composition may include independently applying power from the power source to the ejection heating element and the atomizer. Dispensing the aerosol precursor composition and heating the aerosol precursor composition may include directing power to the atomizer after applying power to the ejection heating element. The method may additionally include preheating the aerosol precursor composition with the ejection heating element prior to dispensing the aerosol precursor composition. Further, the method may include detecting a temperature of the aerosol precursor composition, wherein preheating the aerosol precursor composition includes preheating the aerosol precursor composition to a desired temperature. Preheating the aerosol precursor composition may include applying a relatively smaller pulse width or pulse amplitude of power to the ejection heating element as compared to dispensing the aerosol precursor composition. In some embodiments heating the aerosol precursor composition with the atomizer may include heating the aerosol precursor composition with a vaporization heating element.

In an additional aspect, a method for aerosolization in an aerosol delivery device is provided. The method may include directing an airflow from a control body comprising a power source through a cartridge including a reservoir. Further, the method may include dispensing an aerosol precursor composition from the reservoir via a bubble jet head. Additionally, the method may include heating the aerosol precursor composition dispensed from the reservoir by the bubble jet head with an atomizer.

In some embodiments dispensing the aerosol precursor composition and heating the aerosol precursor composition may include independently applying power from the power source to the bubble jet head and the atomizer. Dispensing the aerosol precursor composition and heating the aerosol precursor composition may include directing power to the atomizer after applying power to the bubble jet head. The method may additionally include preheating the aerosol precursor composition with the bubble jet head prior to dispensing the aerosol precursor composition. Further, the method may include detecting a temperature of the aerosol precursor composition. Preheating the aerosol precursor composition may include preheating the aerosol precursor composition to a desired temperature. Preheating the aerosol precursor composition may include applying a relatively smaller pulse width or pulse amplitude of power to the bubble jet head as compared to dispensing the aerosol precursor composition.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
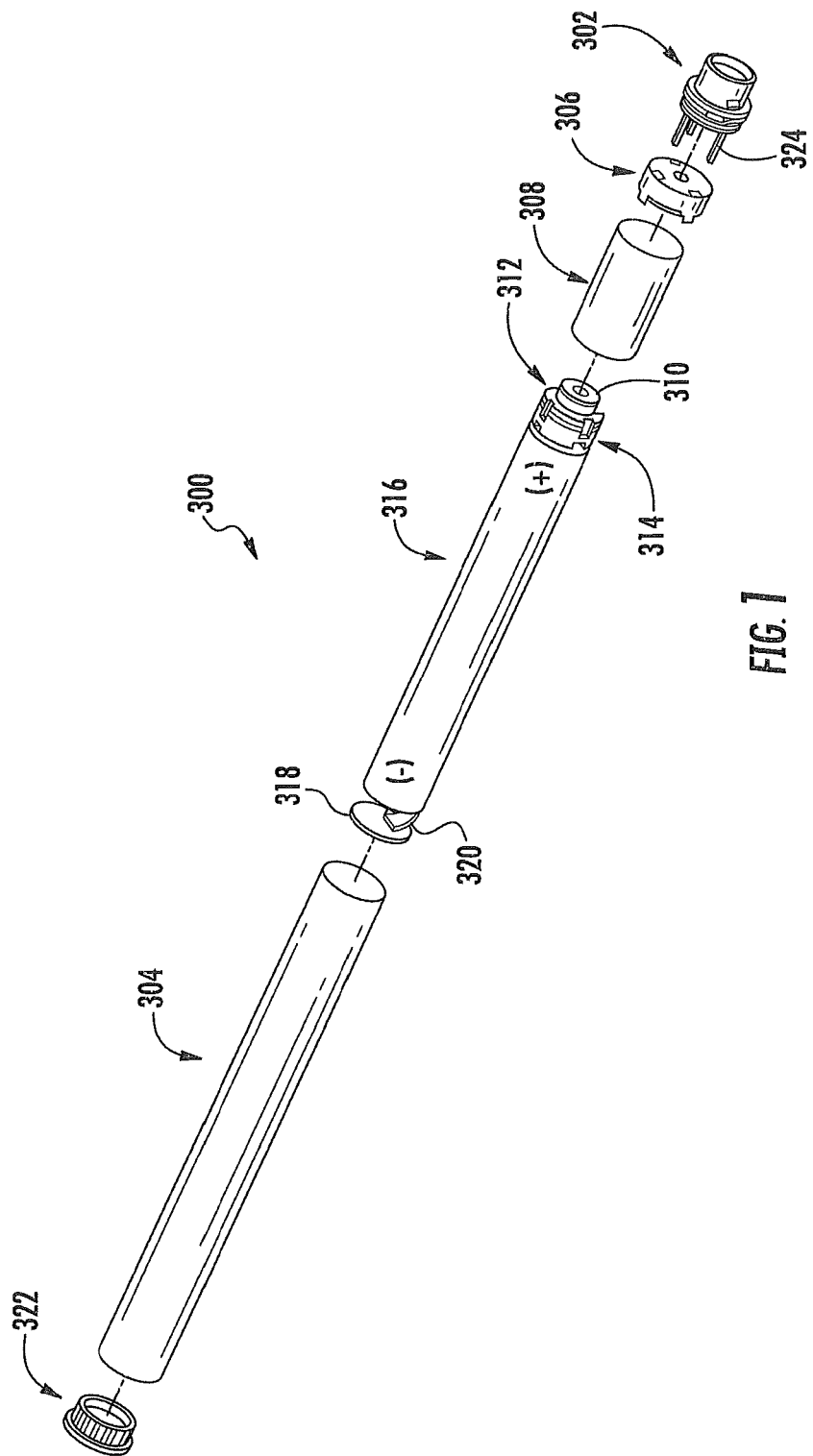
Figure 2:
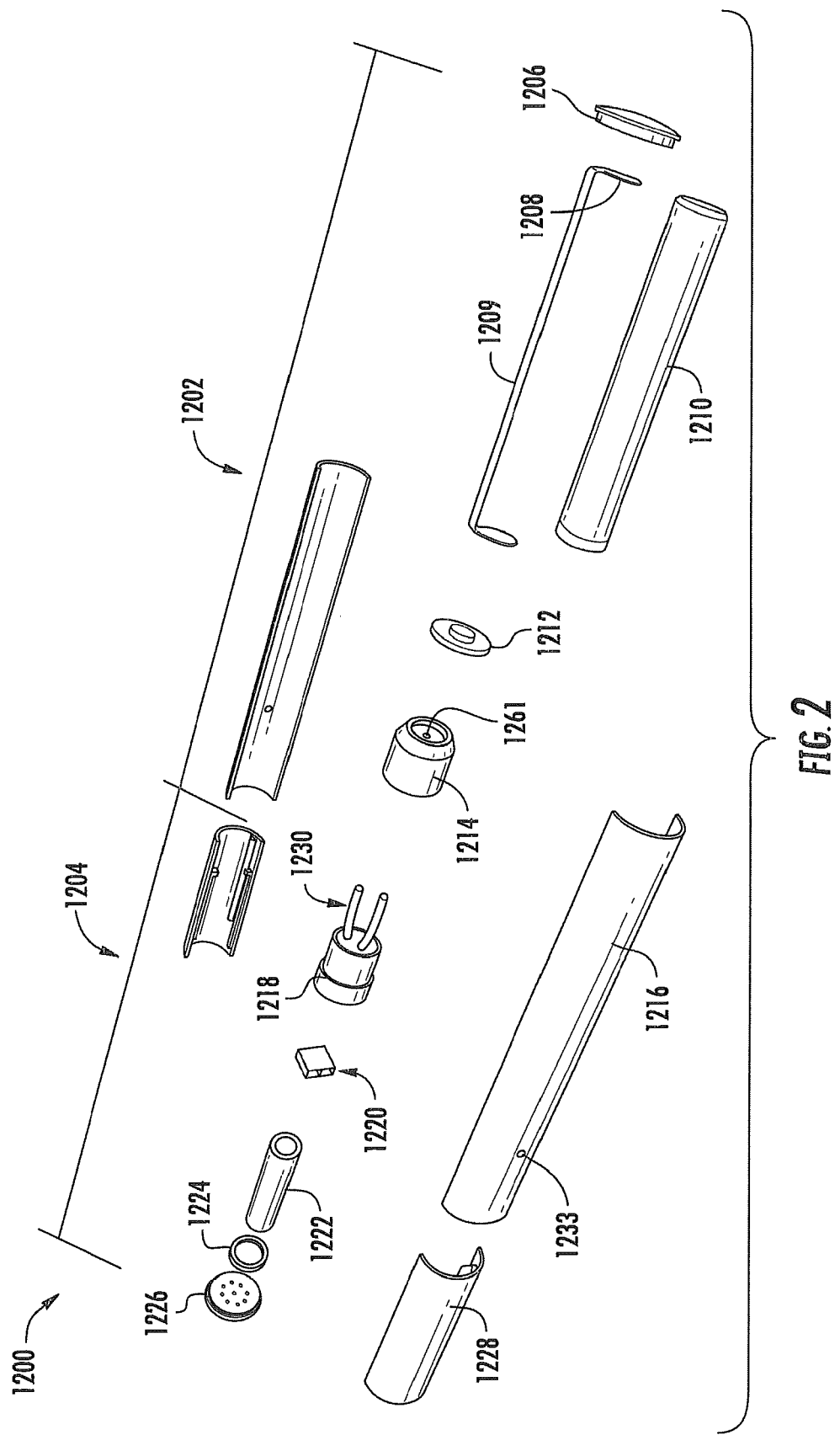
Figure 3:
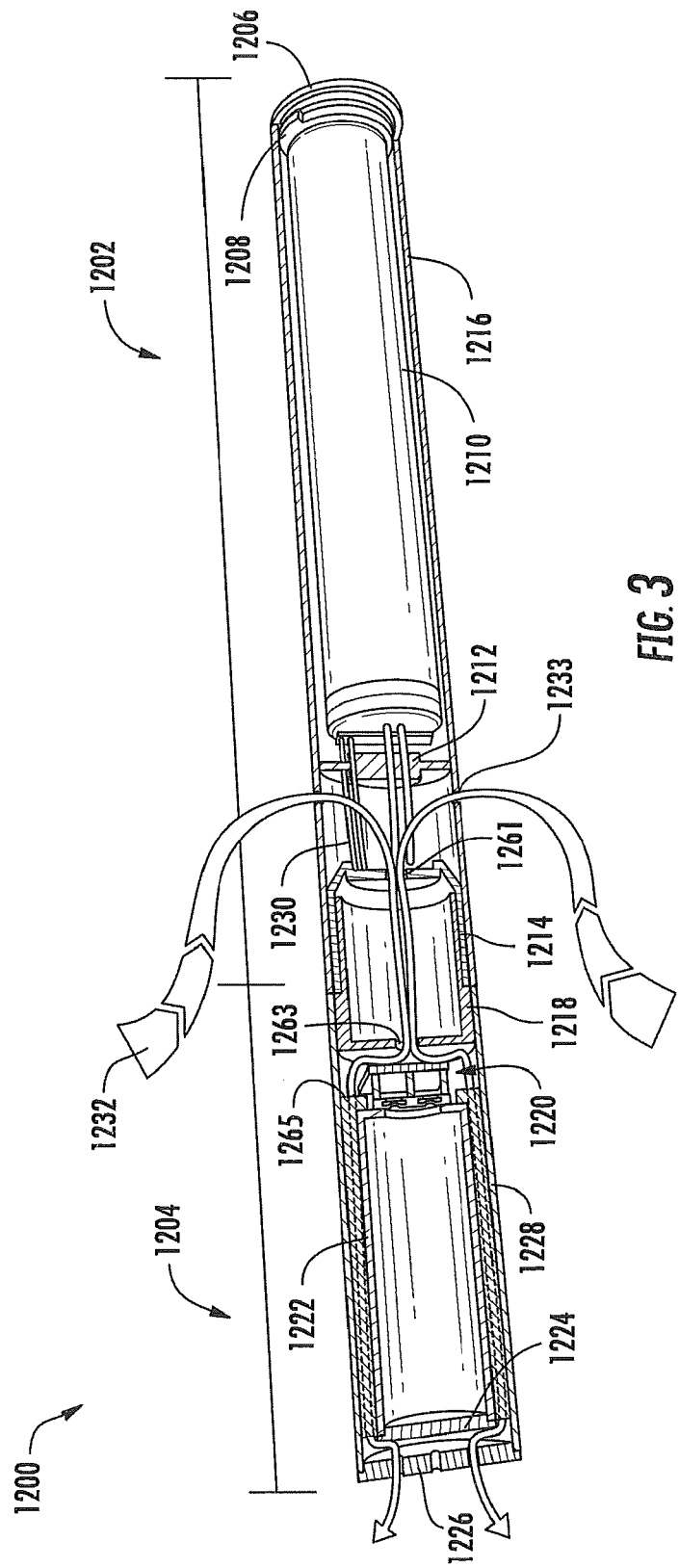
Figure 4:
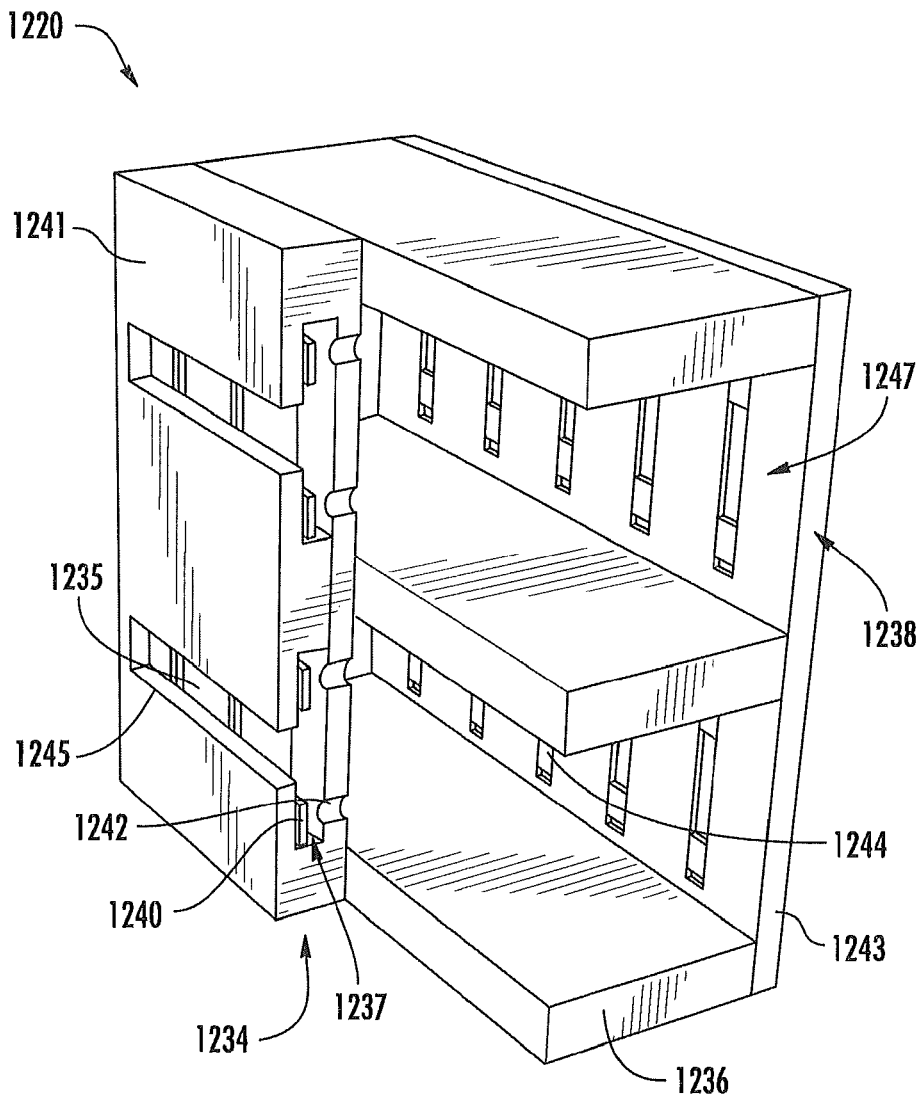
Figure 5:
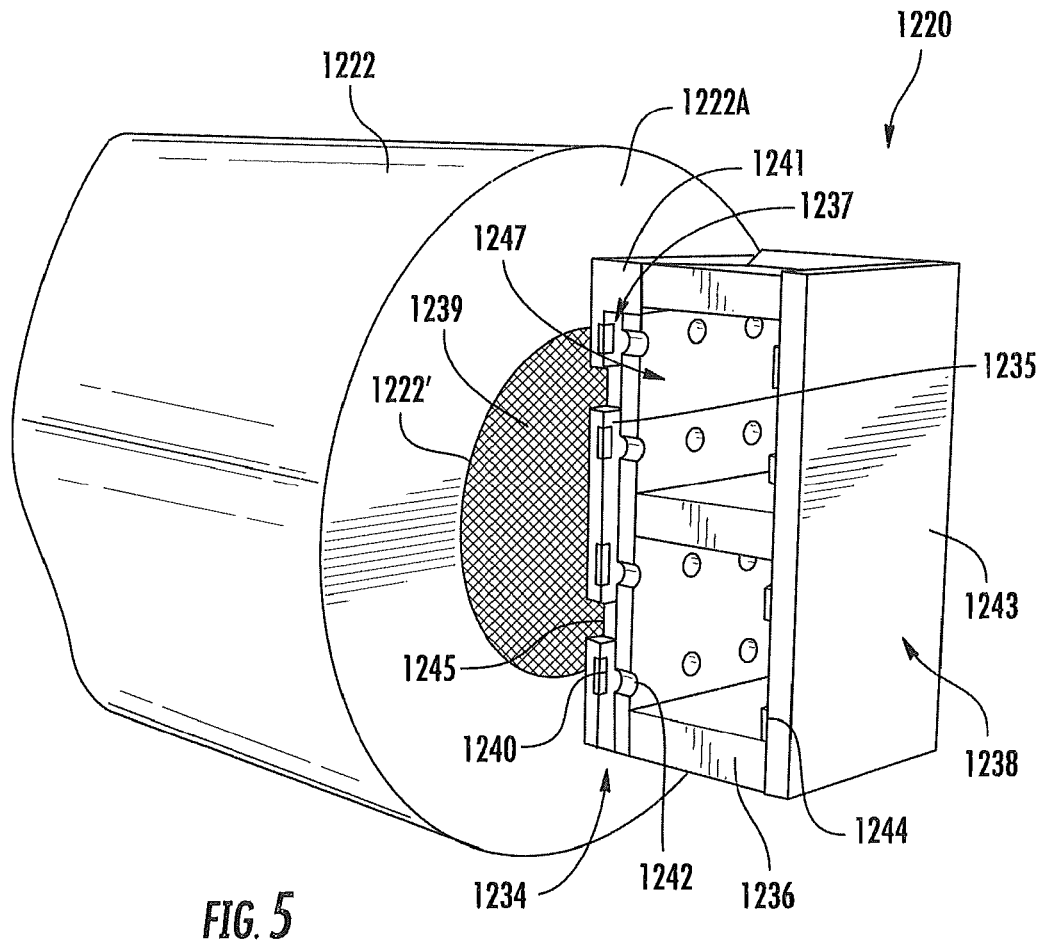
Figure 6:
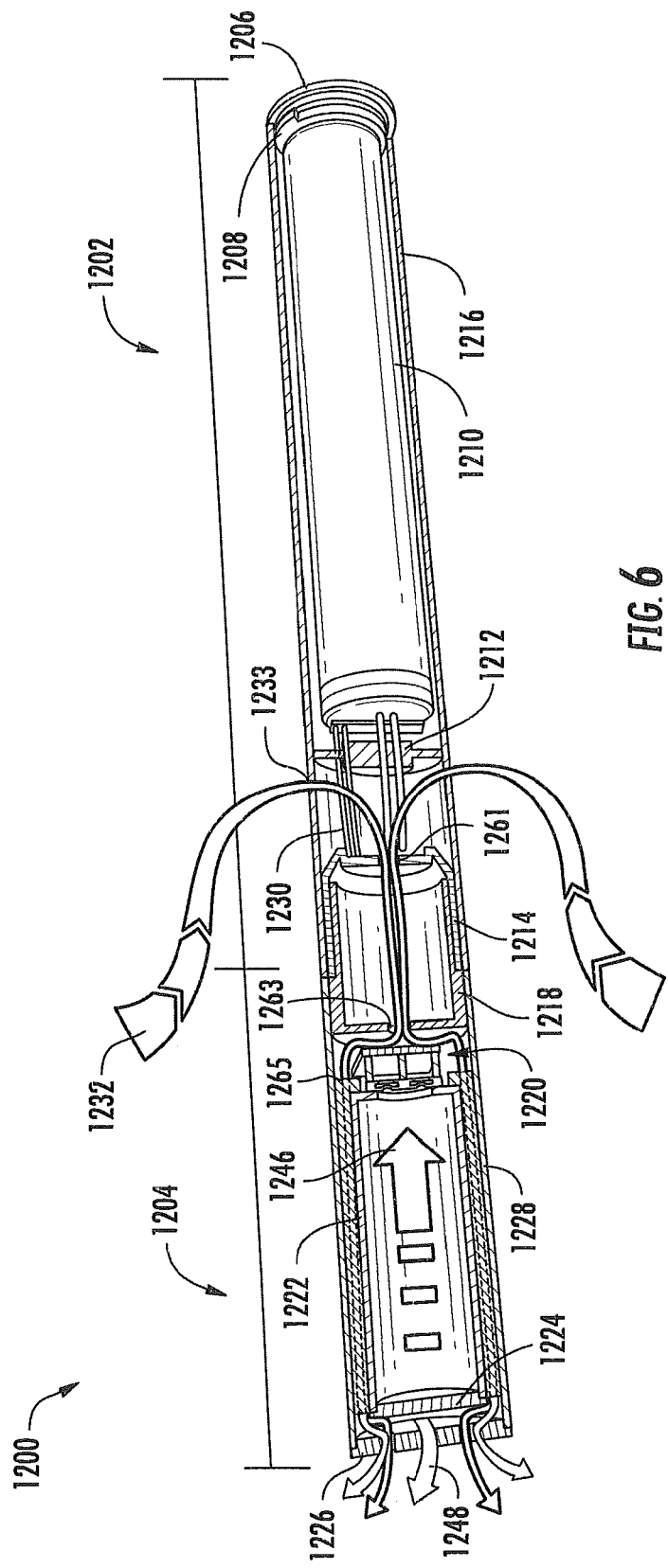
Figure 7:
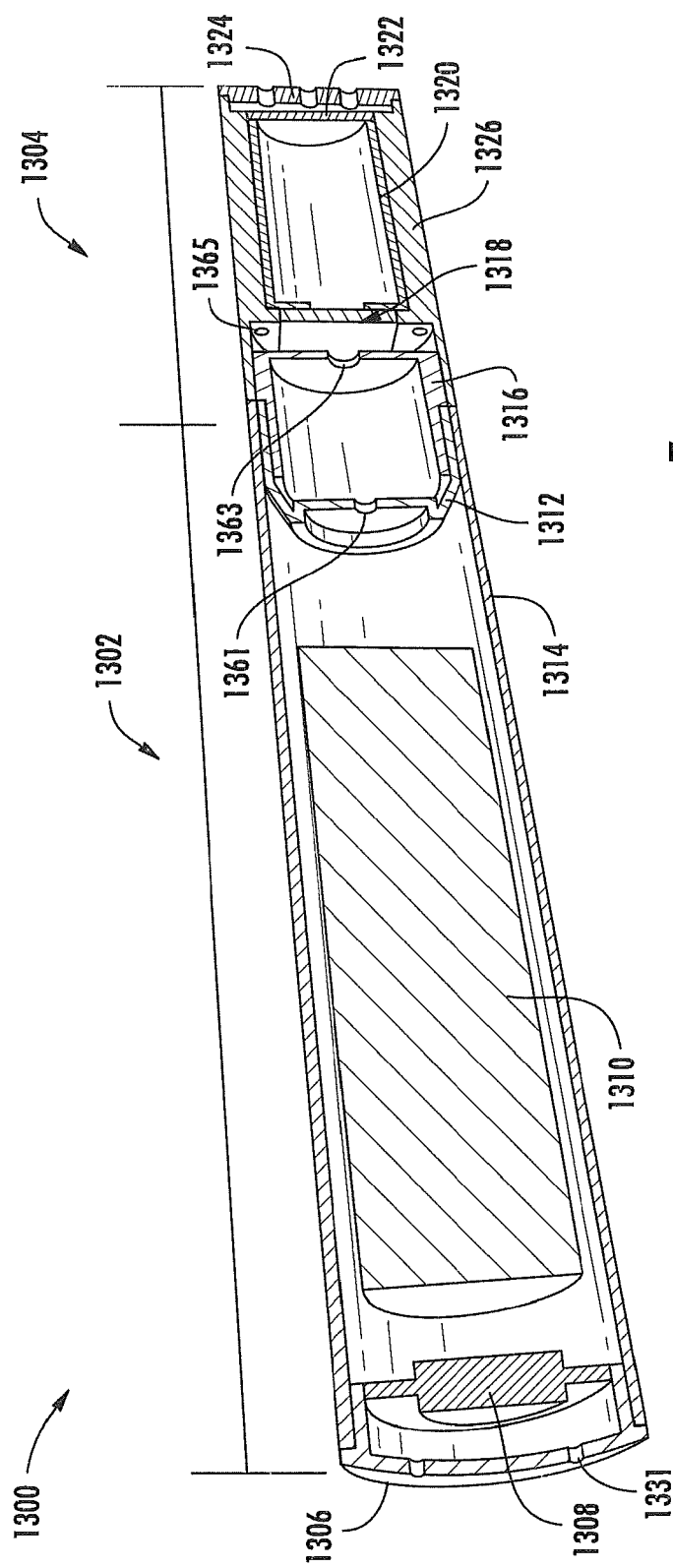
Figure 8:
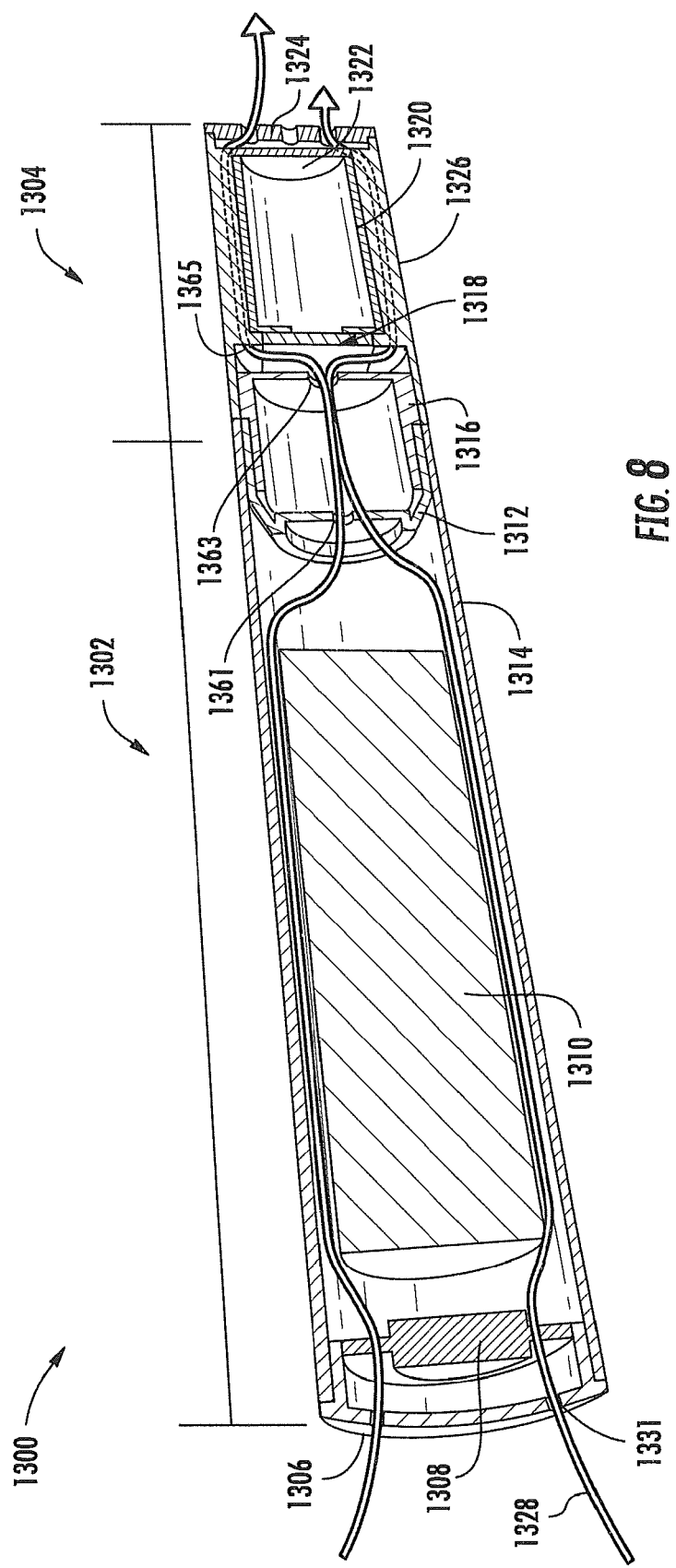
Figure 9:
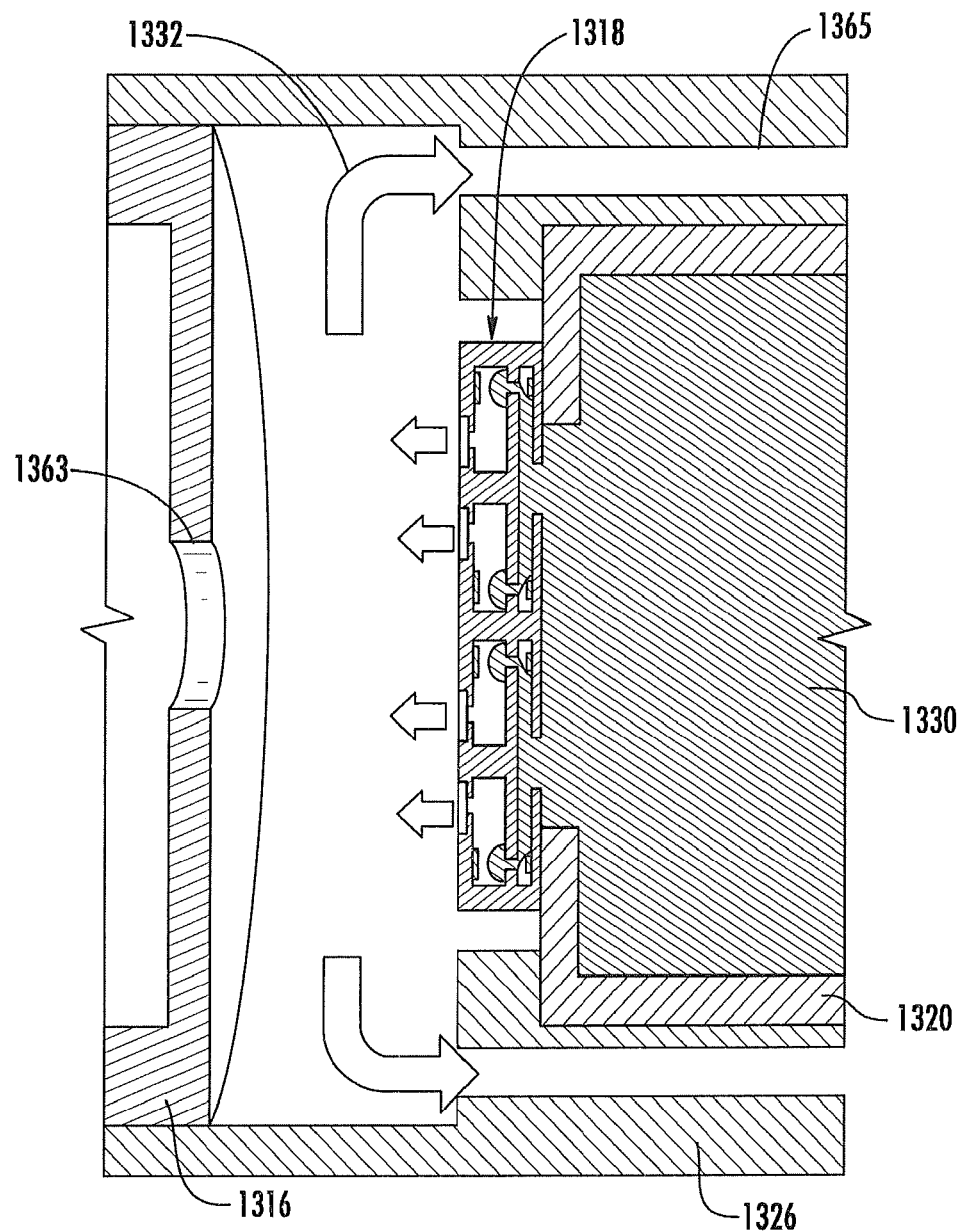
Figure 10:
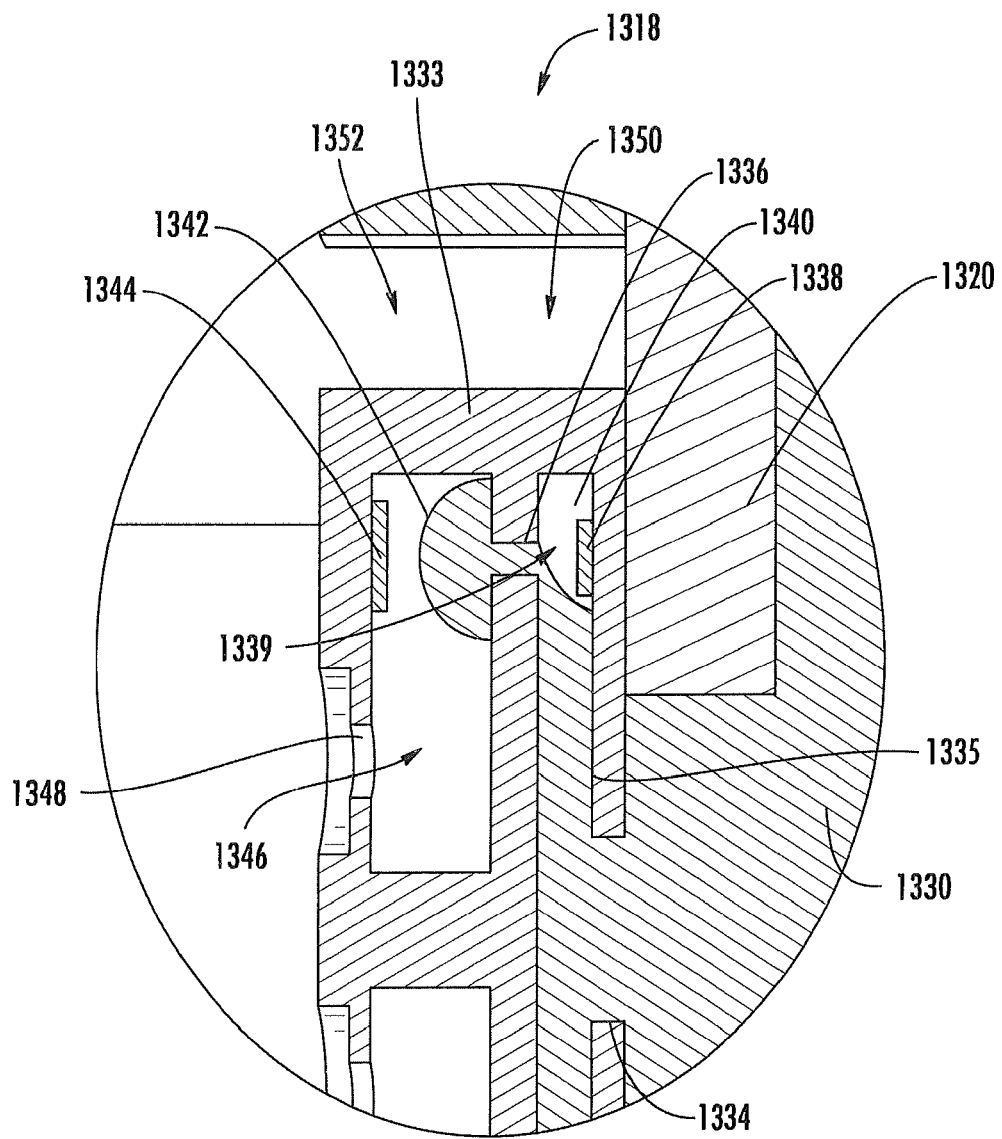
Figure 11:
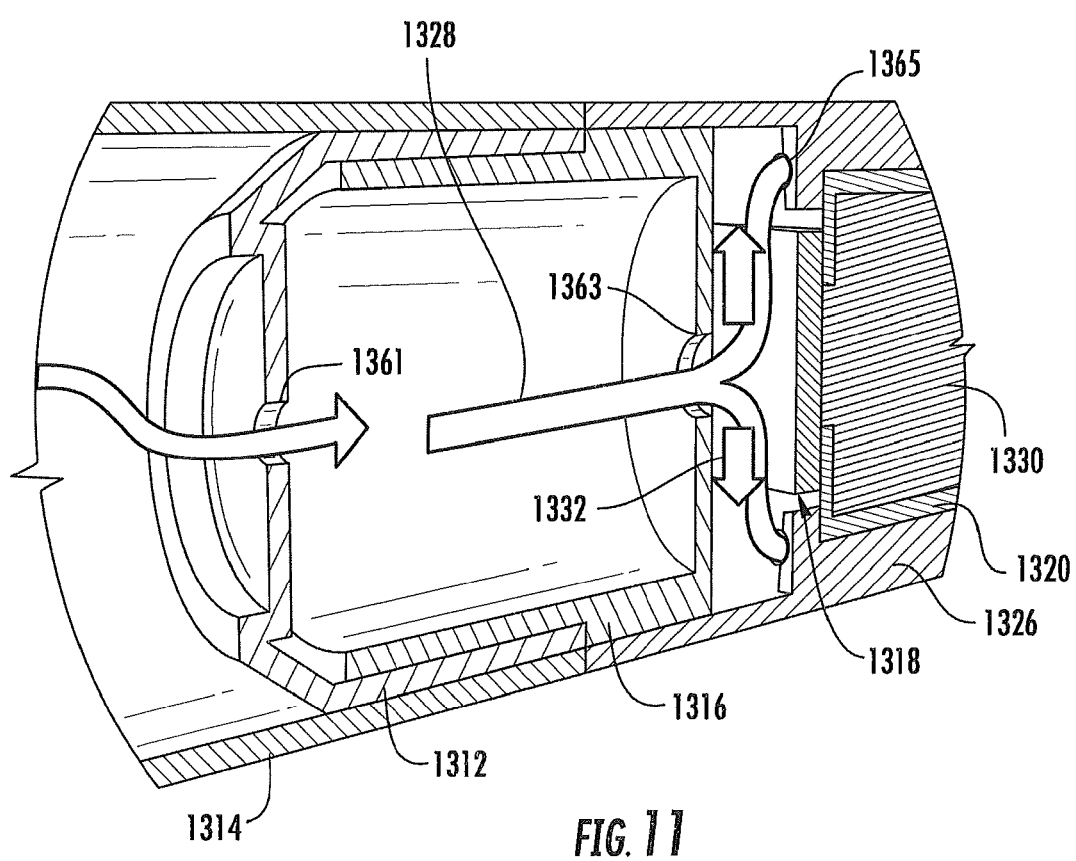
Figure 12:
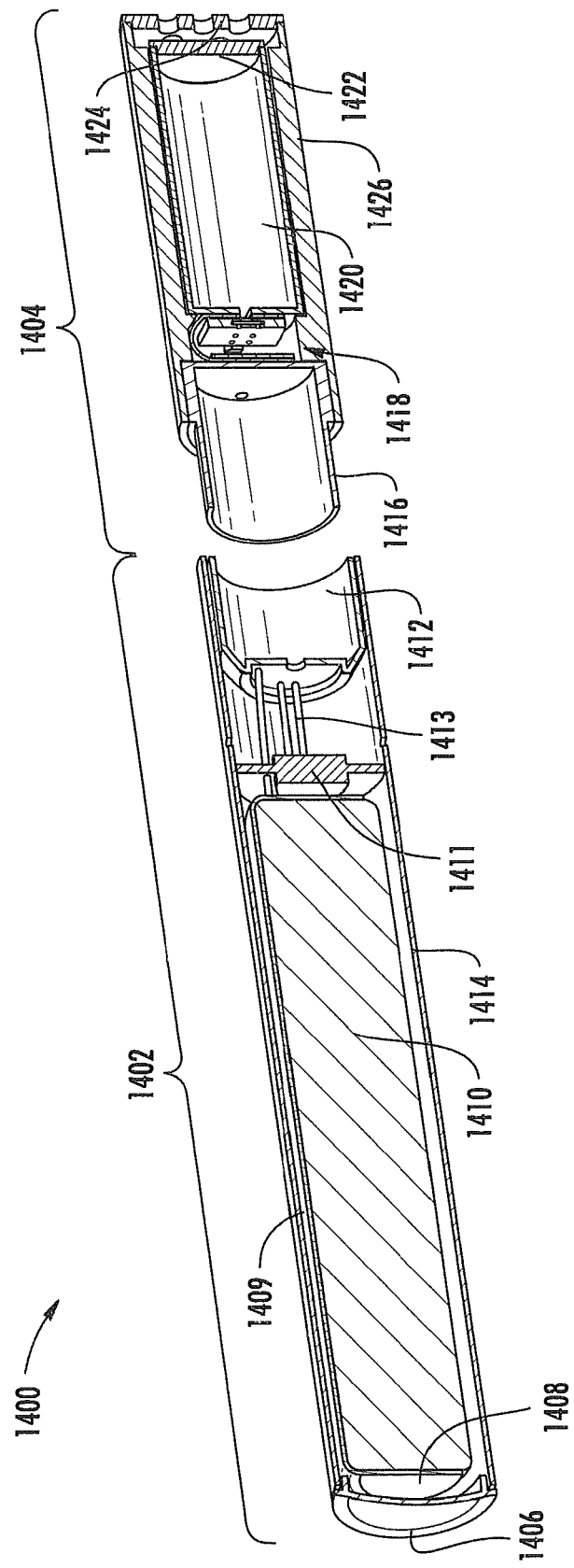
Figure 13:
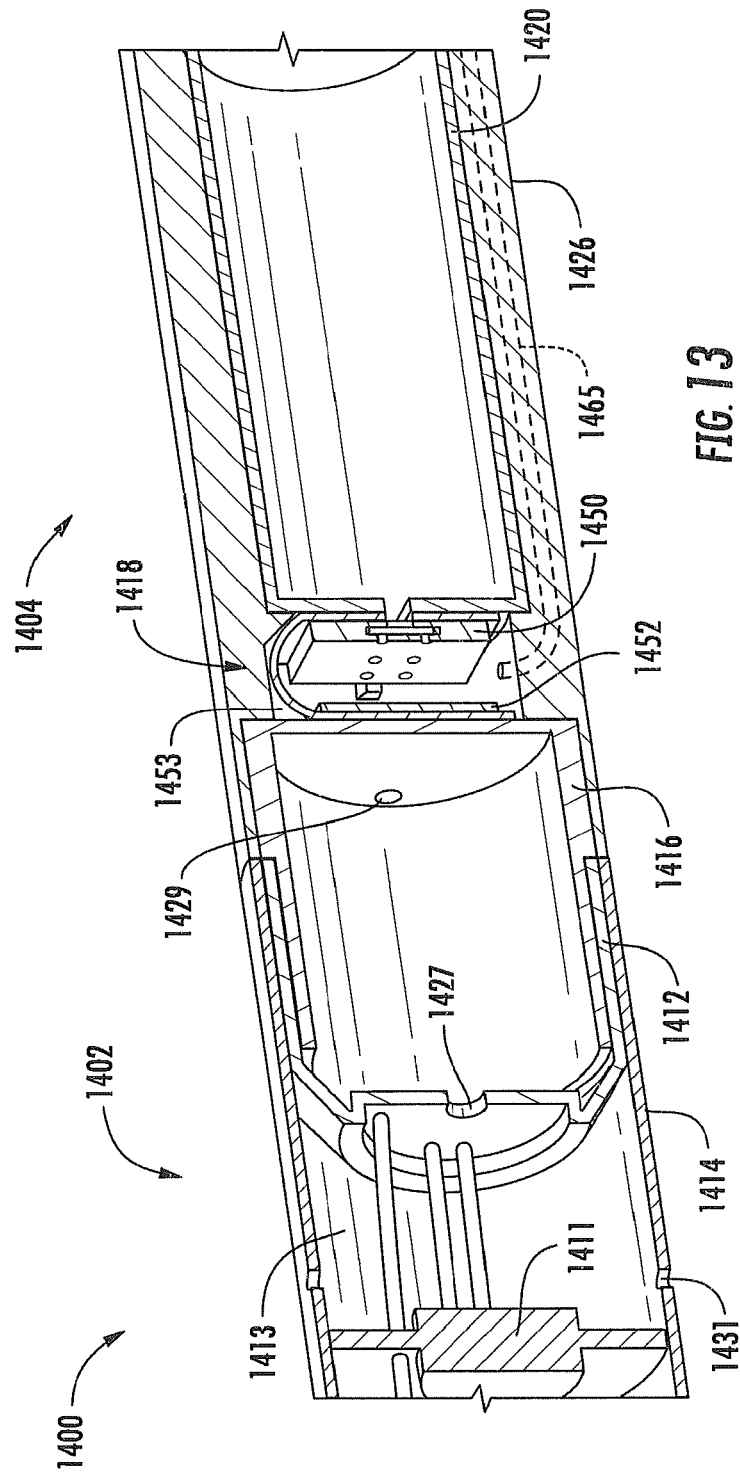
Figure 14:
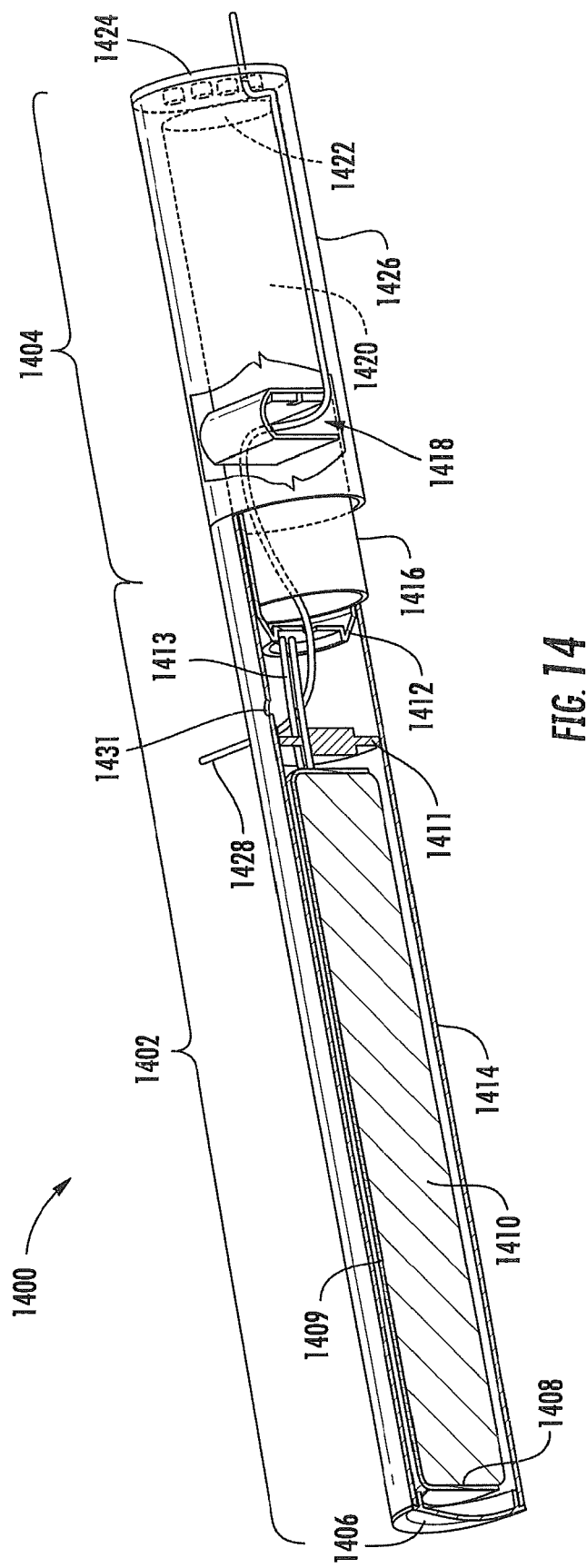
Figure 15:
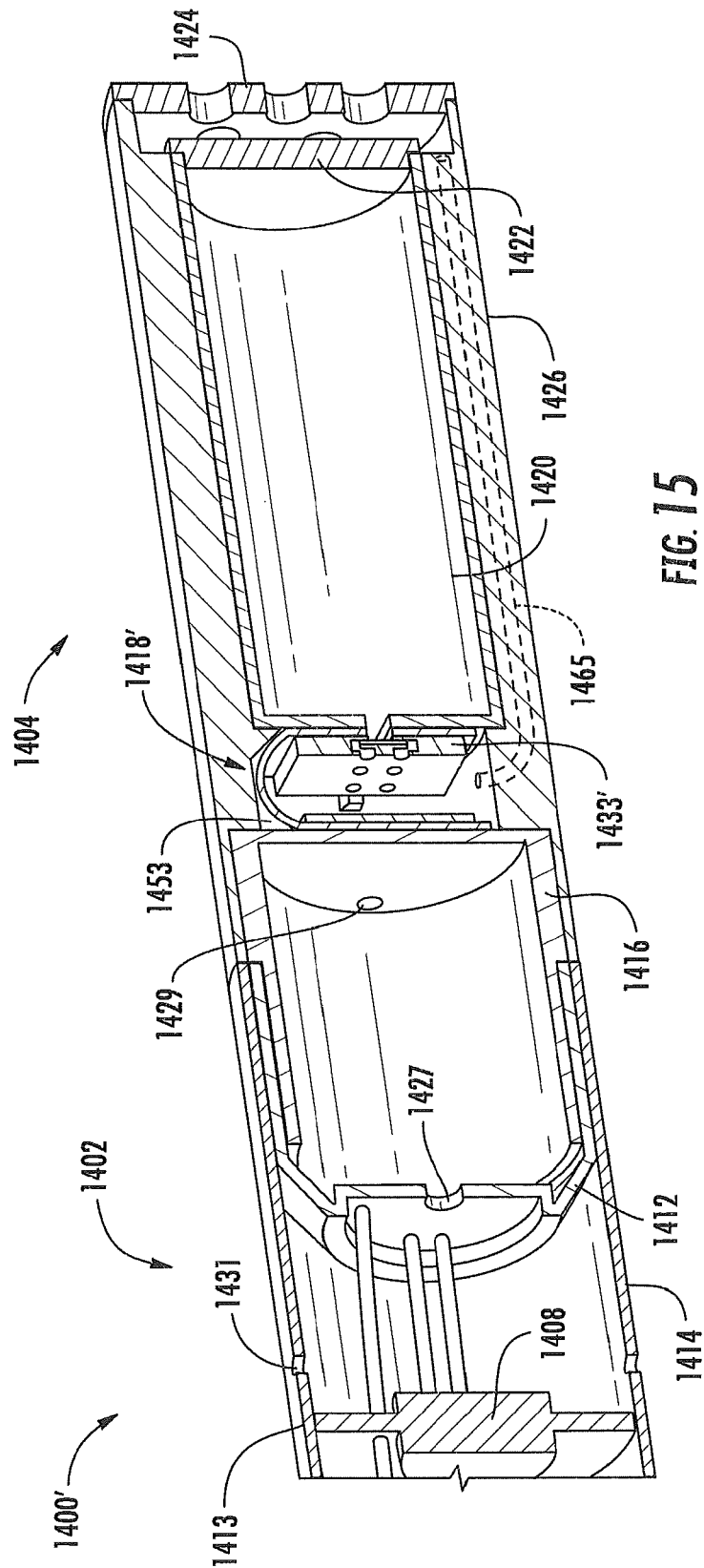
Figure 16:
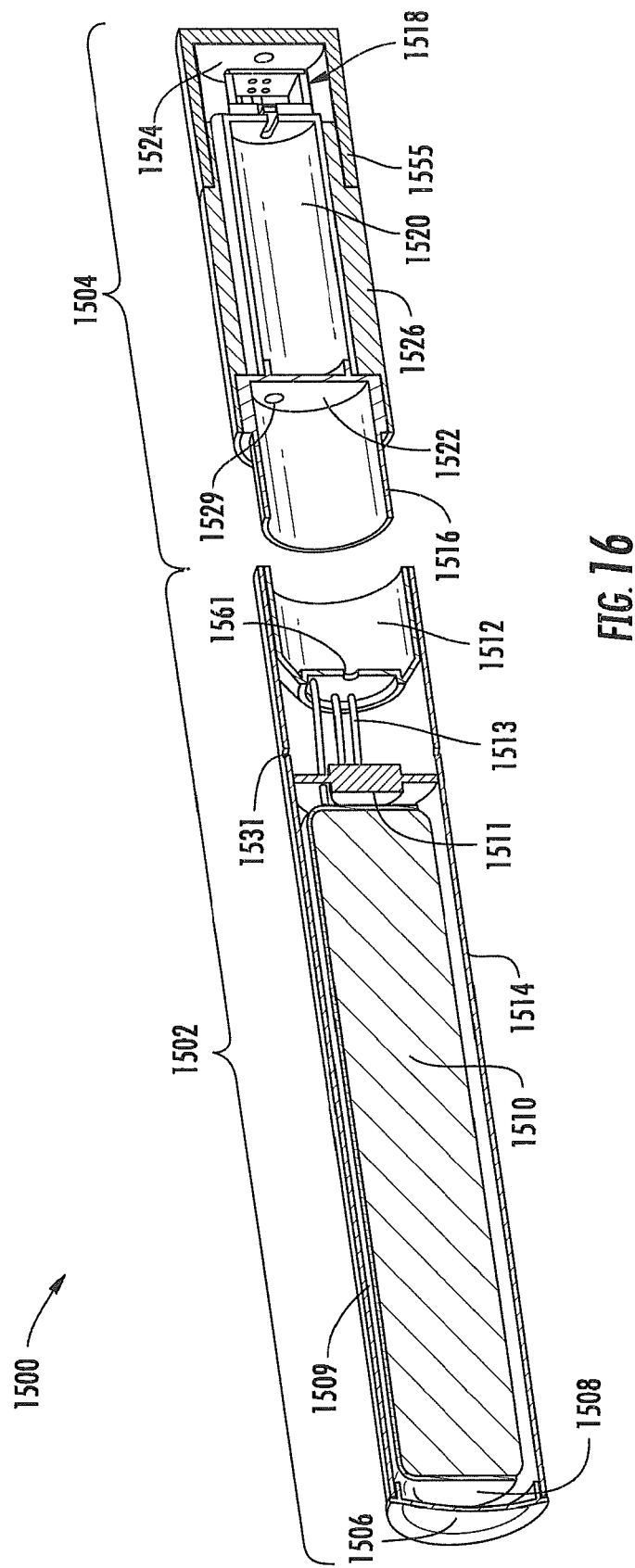
Figure 17:
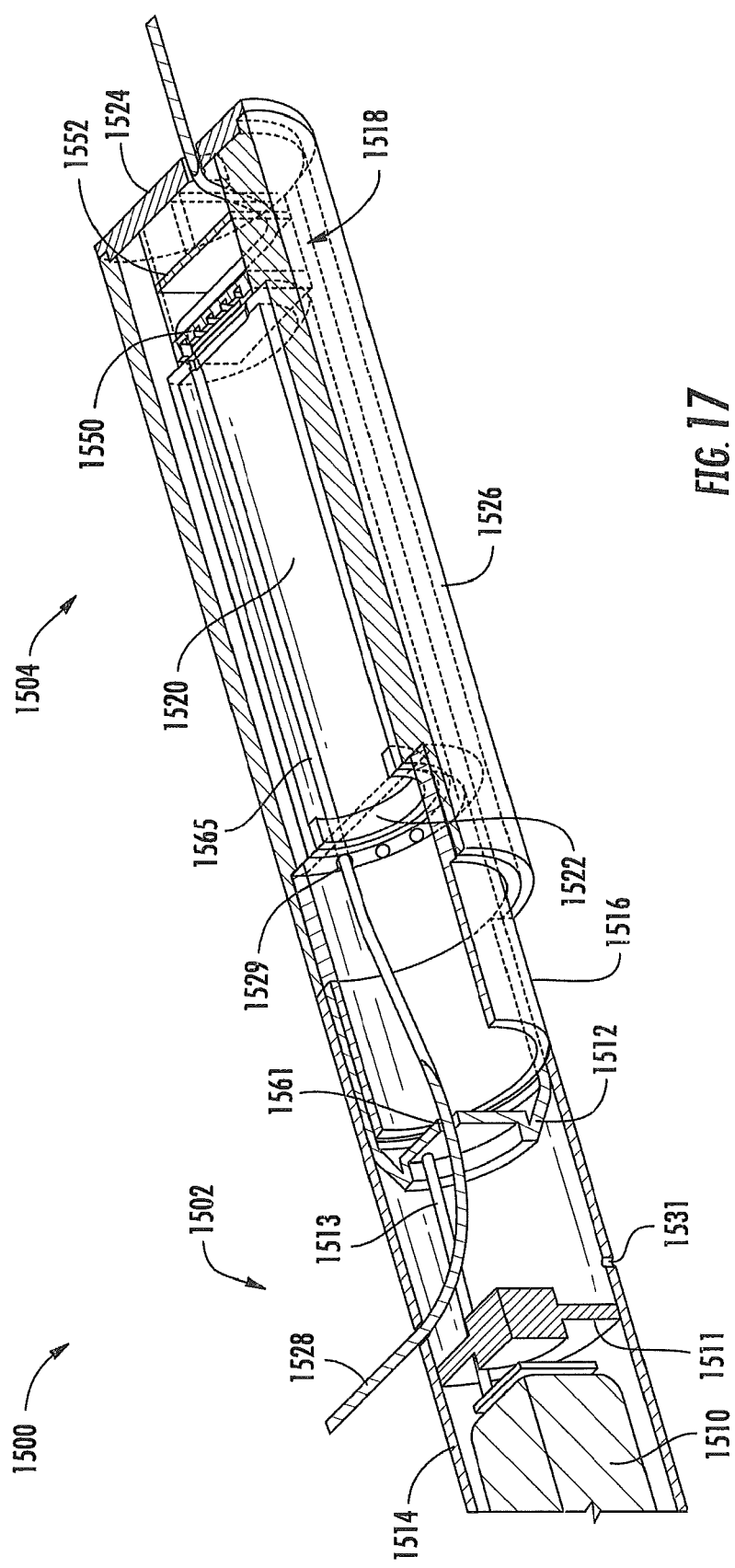
Figure 18:
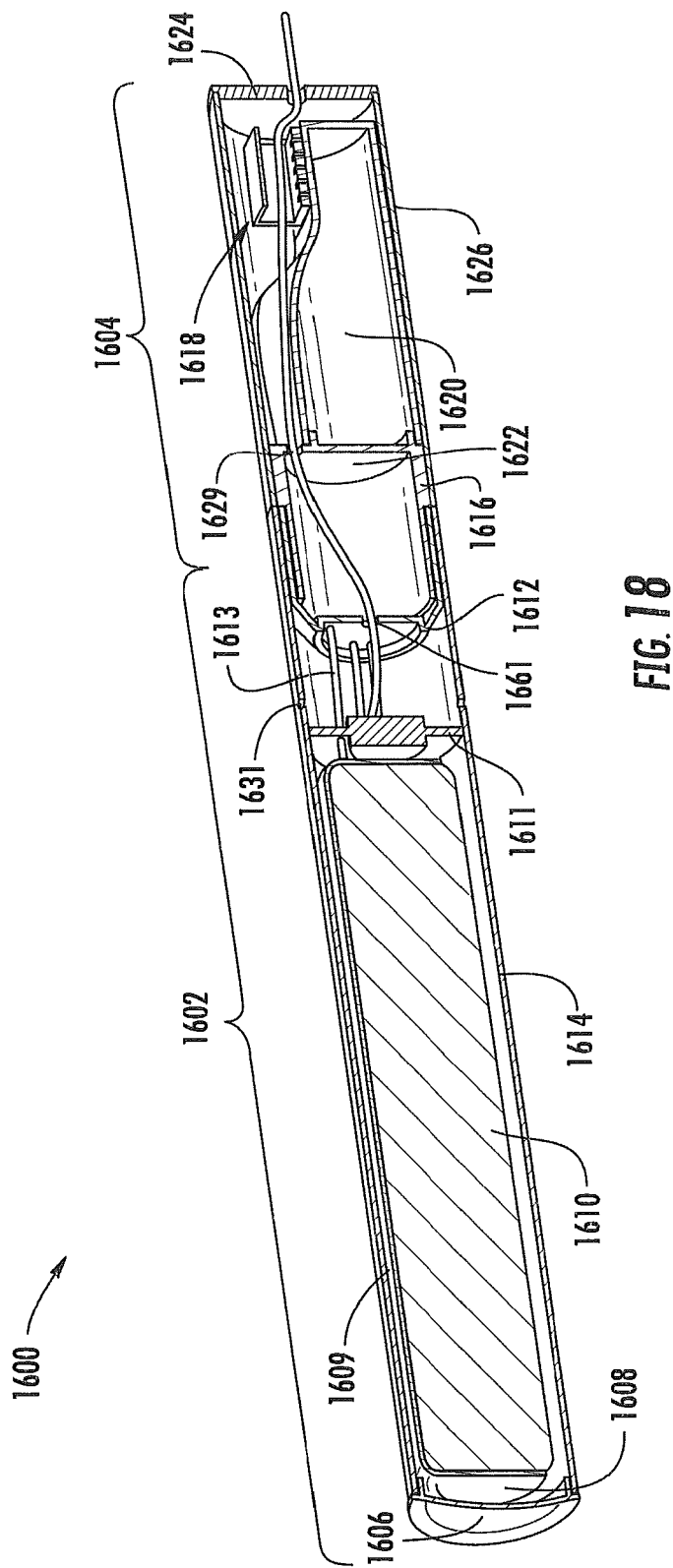
Figure 19:
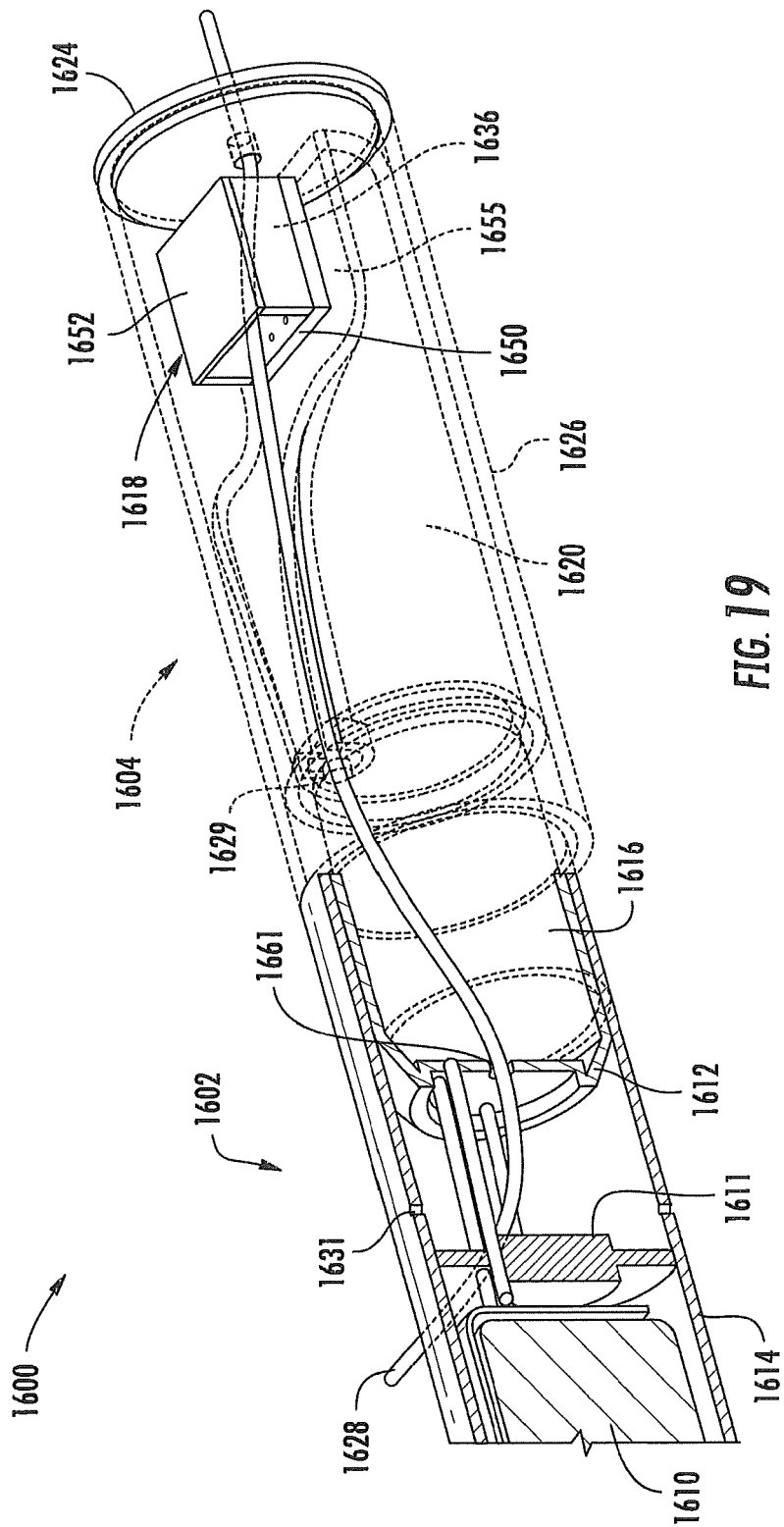
Figure 20:
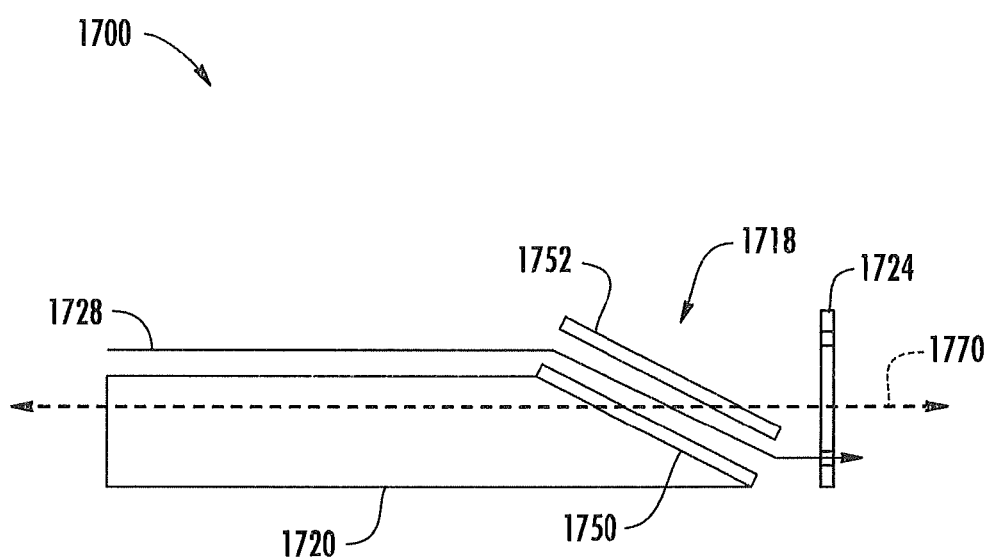
Figure 21:
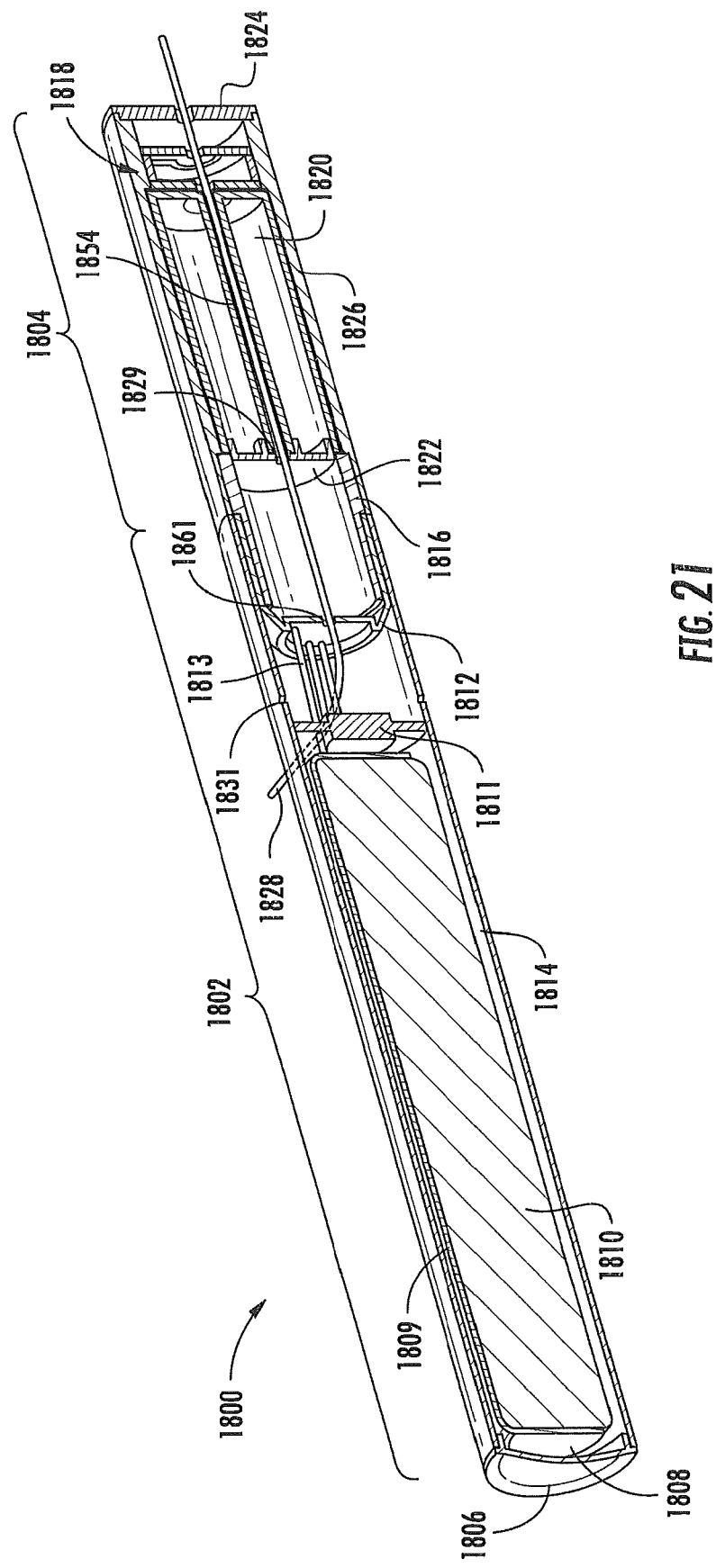
Figure 22:
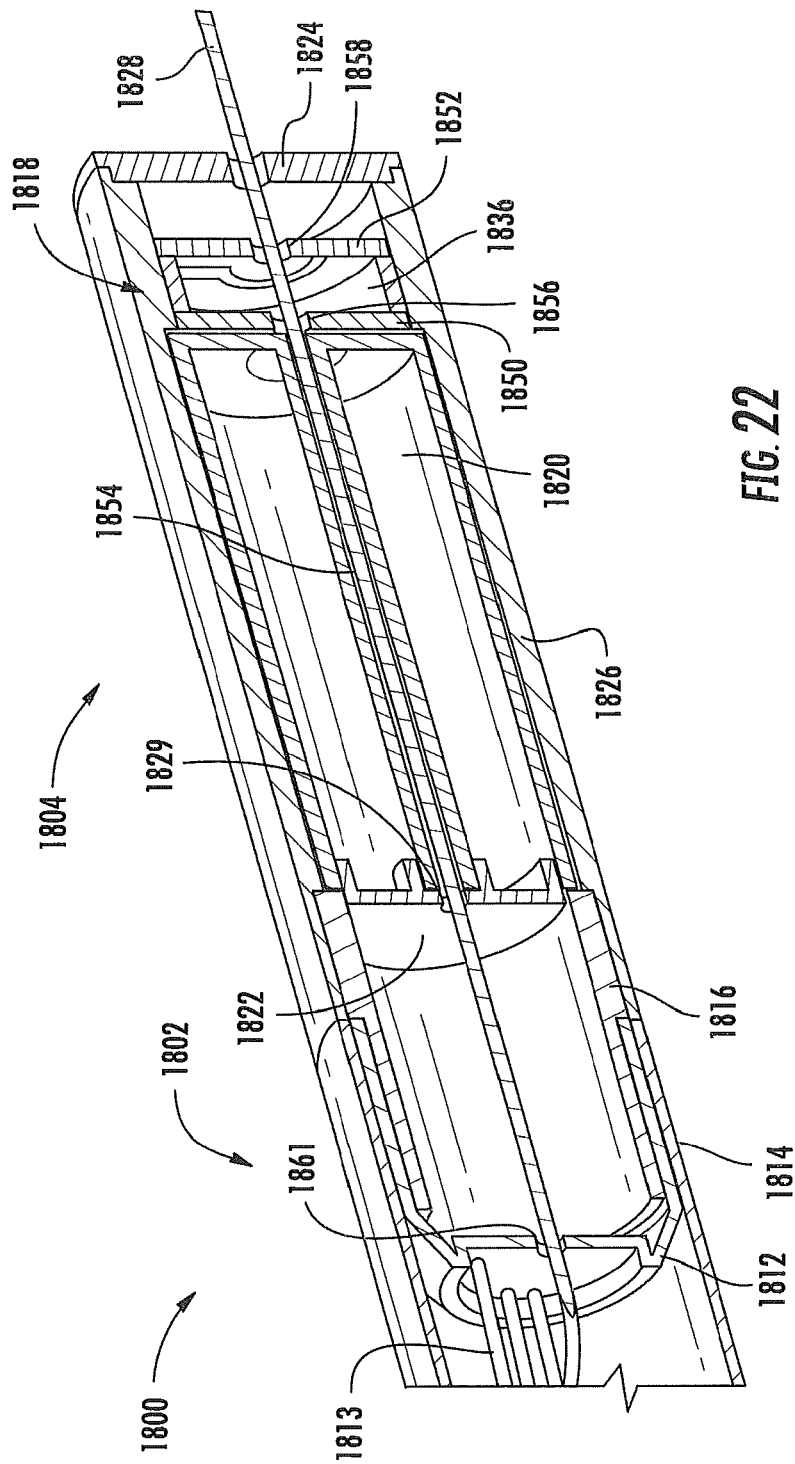
Figure 23:
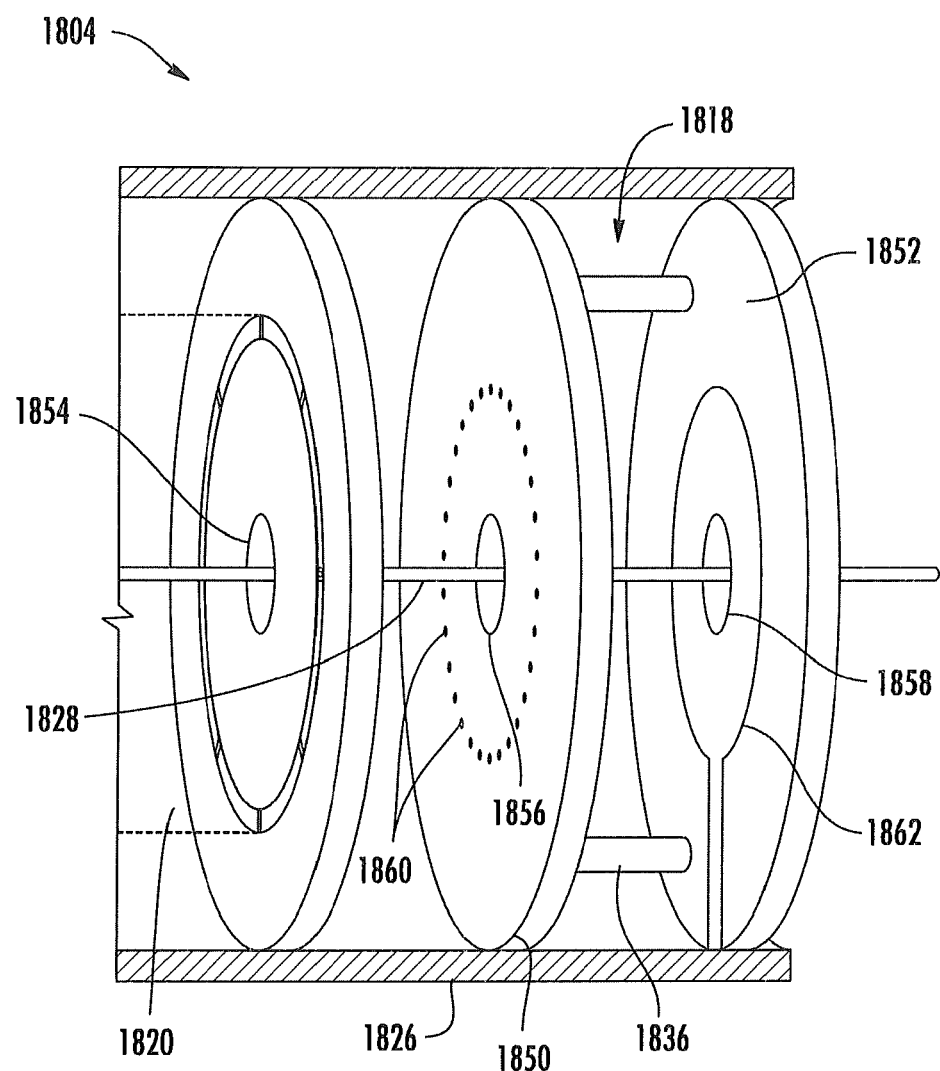
Figure 24:
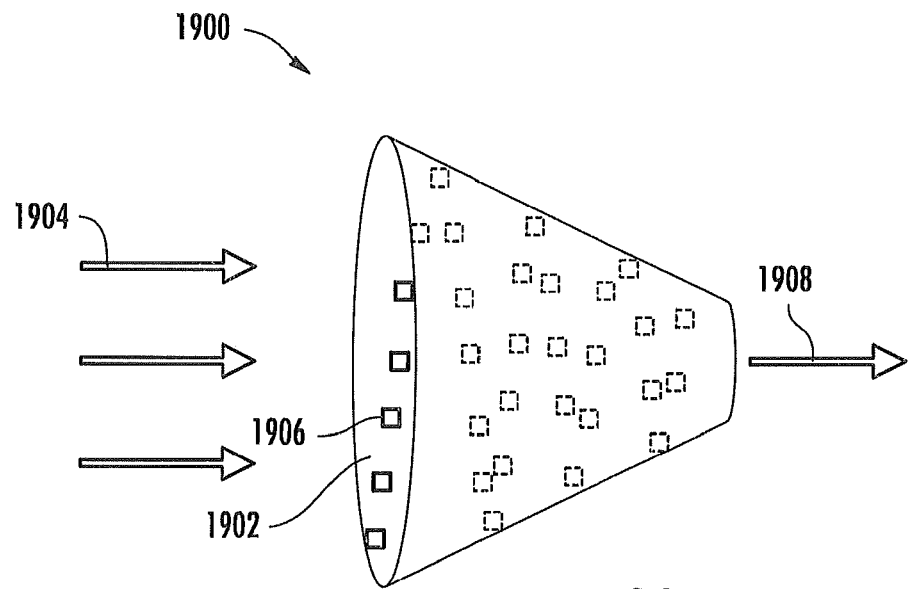
Figure 25:
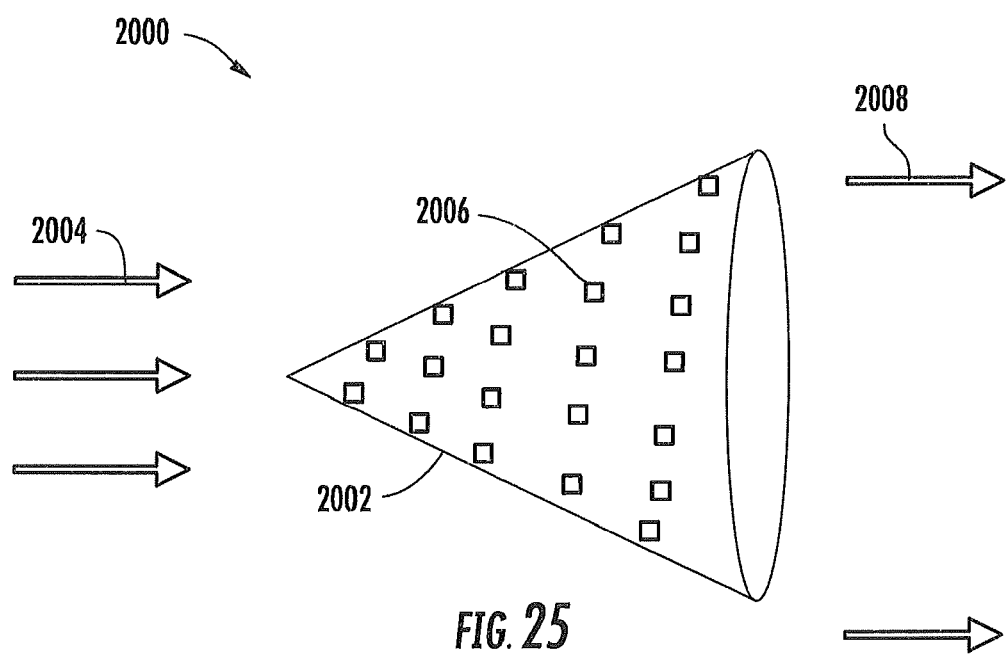
Figure 26:
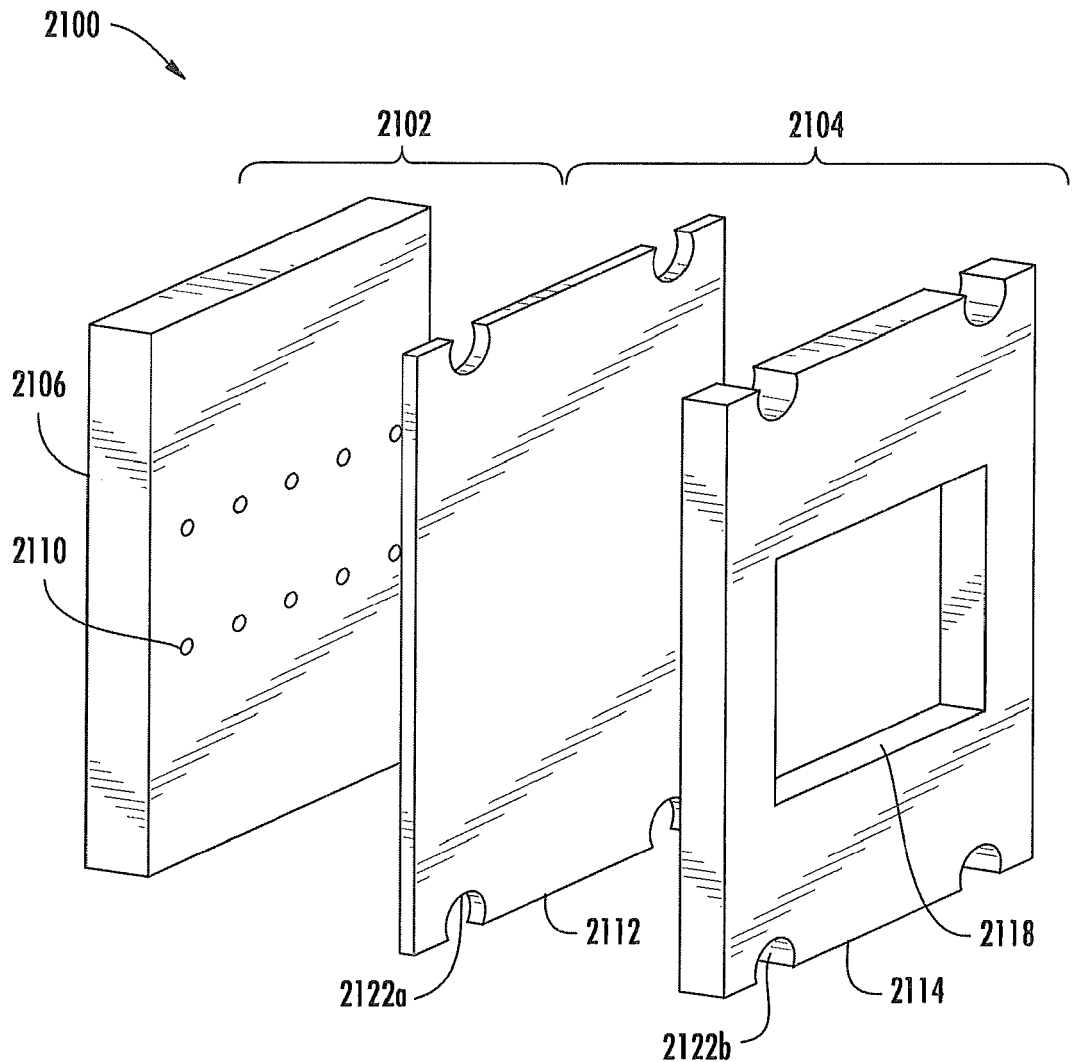
Figure 27:
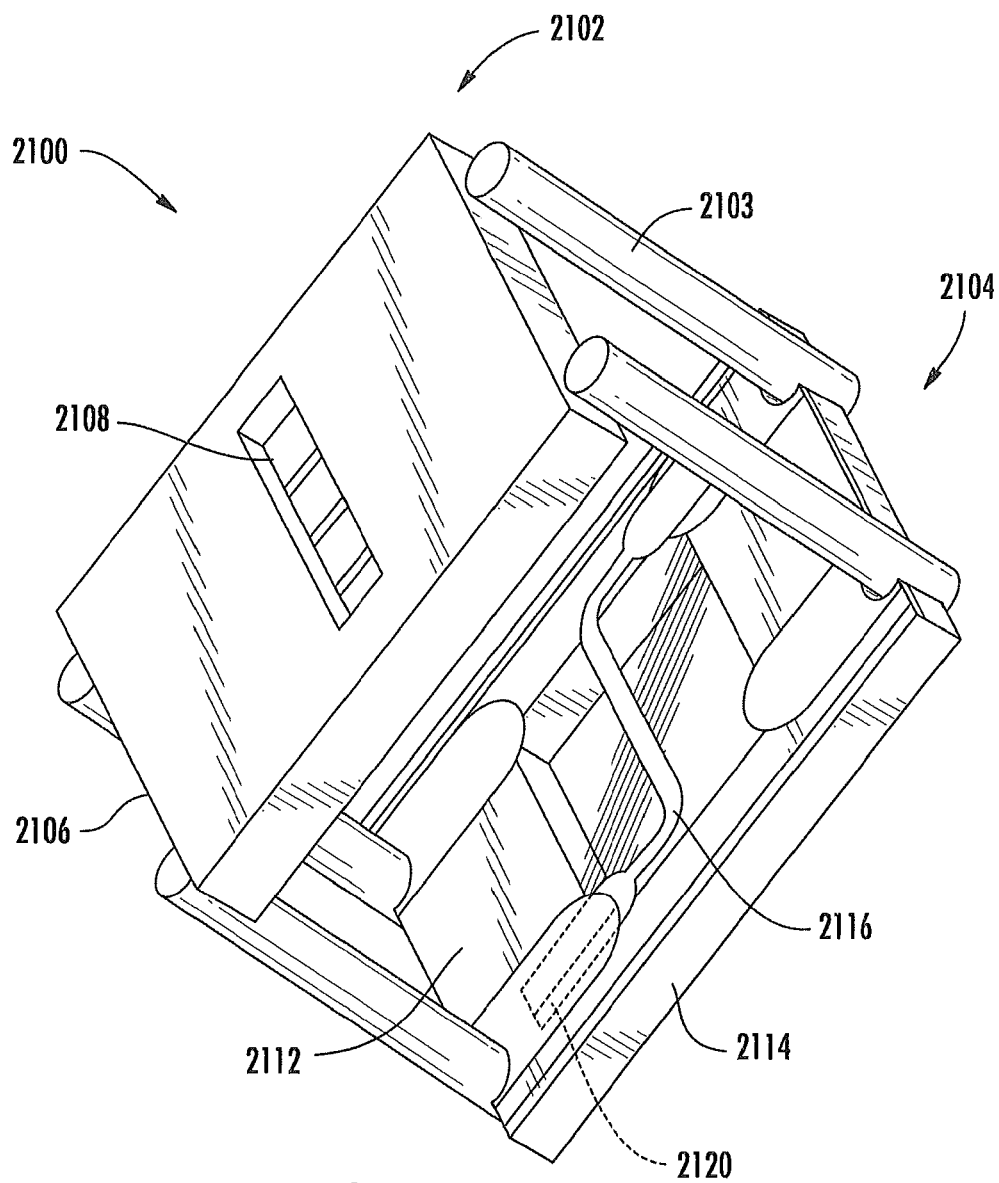
Figure 28A:
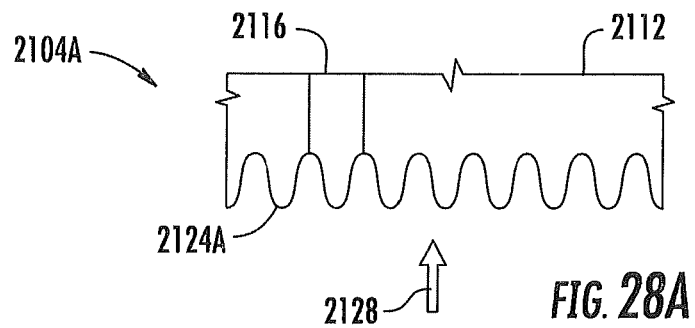
Figure 28B:
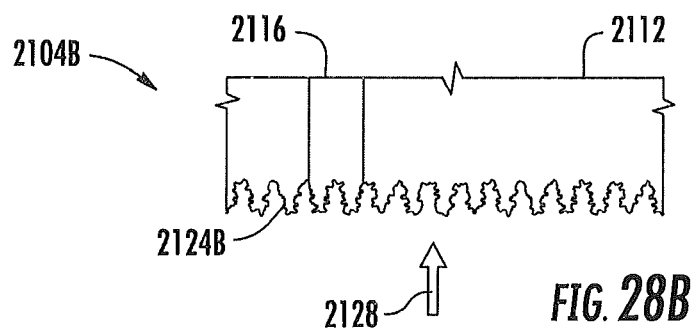
Figure 28C:
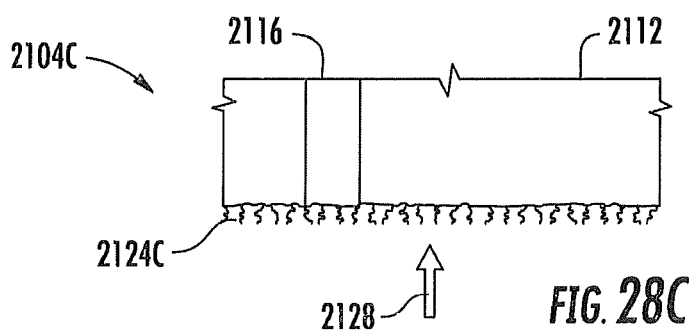
Figure 29:
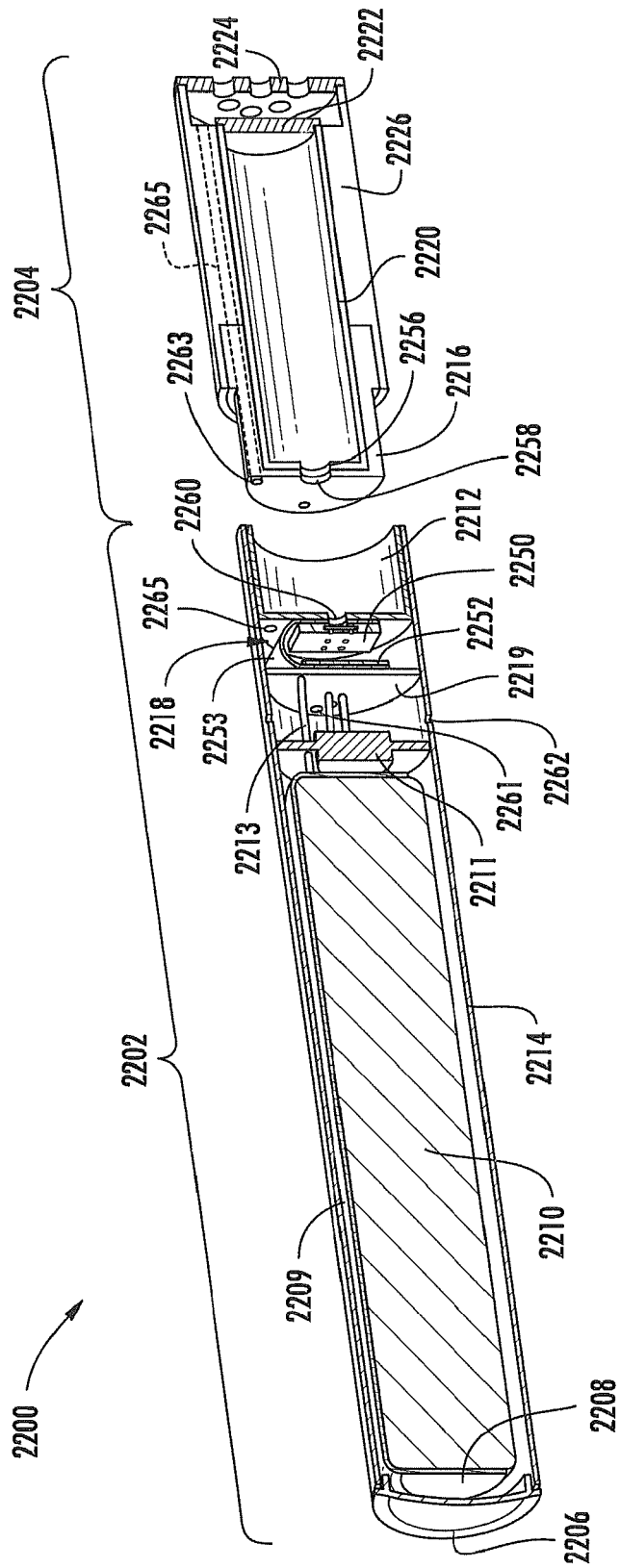
Figure 30:
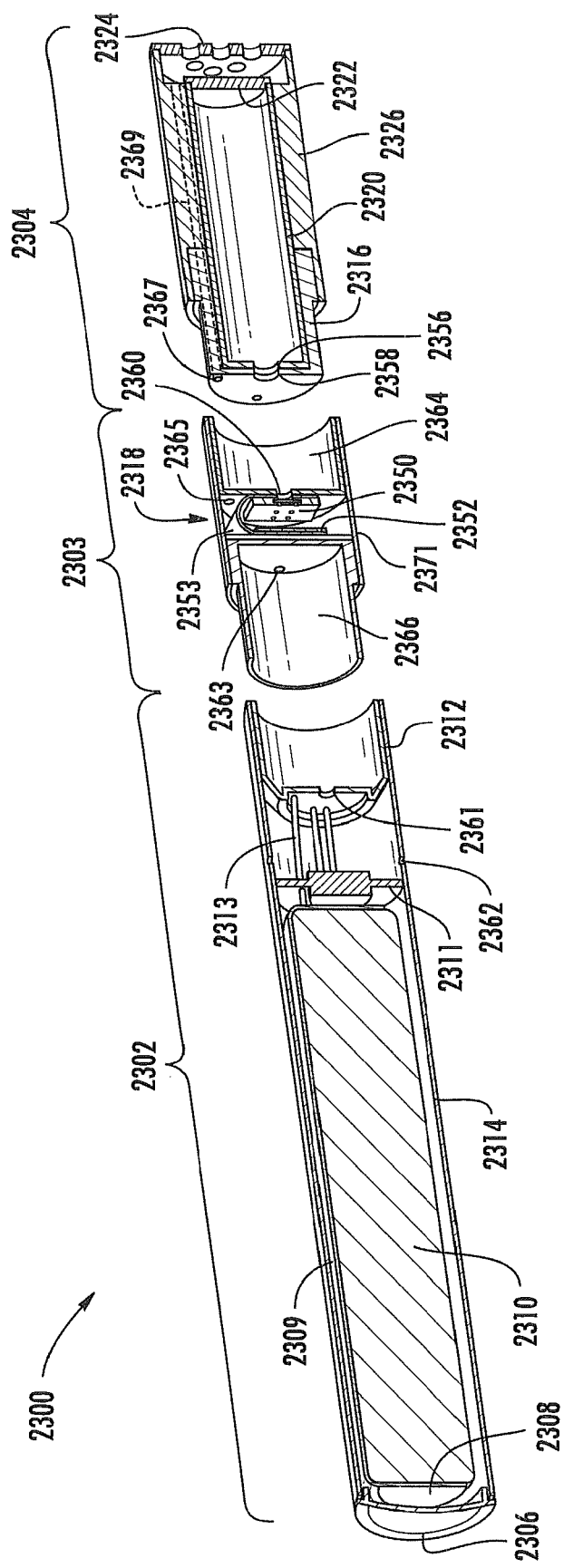

Having thus described the disclosure in the foregoing general terms, reference will now be made to the accompanying drawings, which are not necessarily drawn to scale, and wherein:

FIG. 1 illustrates an exploded view of a control body according to an example embodiment of the present disclosure;

FIG. 2 illustrates an exploded view of an aerosol delivery device including a combined dispenser and atomizer assembly comprising a standard bubble jet head according to an example embodiment of the present disclosure;

FIG. 3 illustrates a modified sectional view through the aerosol delivery device of FIG. 2 showing airflow therethrough according to an example embodiment of the present disclosure;

FIG. 4 illustrates a modified sectional view through the combined dispenser and atomizer assembly of the aerosol delivery device of FIG. 2 according to an example embodiment of the present disclosure;

FIG. 5 illustrates a perspective modified sectional view through the aerosol delivery device of FIG. 2 at the combined dispenser and atomizer assembly and a reservoir according to an example embodiment of the present disclosure;

FIG. 6 illustrates a modified sectional view through the aerosol delivery device of FIG. 2 showing production of vapor according to an example embodiment of the present disclosure;

FIG. 7 illustrates a sectional view through an additional embodiment of an aerosol delivery device including an integral combined dispenser and atomizer assembly according to an example embodiment of the present disclosure;

FIG. 8 illustrates a sectional view through the aerosol delivery device of FIG. 7 showing airflow therethrough according to an example embodiment of the present disclosure;

FIG. 9 illustrates a sectional view through the combined dispenser and atomizer assembly of the aerosol delivery device of FIG. 7 according to an example embodiment of the present disclosure;

FIG. 10 illustrates an enlarged sectional view through the combined dispenser and atomizer assembly of the aerosol delivery device of FIG. 7 according to an example embodiment of the present disclosure;

FIG. 11 illustrates a partial sectional view through the aerosol delivery device of FIG. 7 showing production of vapor according to an example embodiment of the present disclosure;

FIG. 12 illustrates a sectional view through an aerosol delivery device including a combined dispenser and atomizer assembly including a flexible circuit according to an additional example embodiment of the present disclosure;

FIG. 13 illustrates an enlarged, partial, sectional view through the aerosol delivery device of FIG. 12 at the combined dispenser and atomizer assembly according to an example embodiment of the present disclosure;

FIG. 14 illustrates a modified sectional view through the aerosol delivery device of FIG. 12 showing airflow therethrough according to an example embodiment of the present disclosure;

FIG. 15 illustrates a partial sectional view through an aerosol delivery device that is substantially similar to the aerosol delivery device of FIG. 12, except the aerosol delivery device includes an integral combined dispenser and atomizer assembly according to an additional example embodiment of the present disclosure;

FIG. 16 illustrates a sectional view through an aerosol delivery device including a combined dispenser and atomizer assembly positioned between a reservoir and a mouthpiece according to an additional example embodiment of the present disclosure;

FIG. 17 illustrates an enlarged, partial, sectional view through the aerosol delivery device of FIG. 16 showing airflow therethrough according to an example embodiment of the present disclosure;

FIG. 18 illustrates a sectional view through an aerosol delivery device including a combined dispenser and atomizer assembly coupled to a lateral side of a reservoir according to an additional example embodiment of the present disclosure;

FIG. 19 illustrates an enlarged, partial, modified sectional view through the aerosol delivery device of FIG. 18 showing airflow therethrough according to an example embodiment of the present disclosure;

FIG. 20 illustrates a partial, schematic view of an aerosol delivery device wherein respective ejection and heating surfaces of a bubble jet head and an atomizer are oriented at a non-zero angle with respect to a longitudinal axis of the aerosol delivery device according to an additional example embodiment of the present disclosure;

FIG. 21 illustrates a sectional view through an aerosol delivery device including a combined dispenser and atomizer assembly wherein airflow occurs centrally therethrough according to an additional example embodiment of the present disclosure;

FIG. 22 illustrates an enlarged sectional view through the aerosol delivery device of FIG. 21 showing airflow therethrough according to an example embodiment of the present disclosure;

FIG. 23 schematically illustrates an enlarged exploded view of the combined dispenser and atomizer assembly of the aerosol delivery device of FIG. 21 according to an example embodiment of the present disclosure;

FIG. 24 illustrates a perspective view of a substantially conical atomizer defining an inner heating surface according to an additional example embodiment of the present disclosure;

FIG. 25 illustrates a perspective view of a substantially conical atomizer defining an outer heating surface according to an additional example embodiment of the present disclosure;

FIG. 26 illustrates an exploded view of a combined dispenser and atomizer assembly including a reinforcement member according to an additional example embodiment of the present disclosure;

FIG. 27 illustrates an opposing view of the combined dispenser and atomizer assembly of FIG. 26 wherein the reinforcement member is in an assembled configuration according to an example embodiment of the present disclosure;

FIG. 28A illustrates an enlarged sectional view through an atomizer of the combined dispenser and atomizer assembly of FIG. 26 wherein the atomizer defines a crenellated heating surface according to an additional example embodiment of the present disclosure;

FIG. 28B illustrates an enlarged sectional view through an atomizer of the combined dispenser and atomizer assembly of FIG. 26 wherein the atomizer defines a partially porous heating surface according to an additional example embodiment of the present disclosure;

FIG. 28C illustrates an enlarged sectional view through an atomizer of the combined dispenser and atomizer assembly of FIG. 26 wherein the atomizer defines a fully porous heating surface according to an additional example embodiment of the present disclosure;

FIG. 29 illustrates a sectional view through an aerosol delivery device wherein a combined dispenser and atomizer assembly is positioned in a control body according to an additional example embodiment of the present disclosure;

FIG. 30 illustrates a sectional view through an aerosol delivery device comprising a control body, a dispenser and atomizer cartridge, and a reservoir cartridge according to an additional example embodiment of the present disclosure; and FIG. 31 schematically illustrates a method for aerosolization in an aerosol delivery device according to an additional example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As described hereinafter, embodiments of the present disclosure relate to aerosol delivery systems, devices, and components therefor. Aerosol delivery systems according to the present disclosure use electrical energy to heat a material (preferably without combusting the material to any significant degree) to form an inhalable substance; and components of such systems have the form of articles that are most preferably sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being suitable vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas).

Aerosol delivery systems of the present disclosure most preferably comprise some combination of a power source (i.e., an electrical power source), at least one control component (e.g., means for actuating, controlling, regulating and/or ceasing power supplied for heat generation, such as by controlling electrical current flow from an electrical power release unit to other components of the aerosol generating piece), a heater or heat generation component (e.g., an electrical resistance heating element and related components commonly referred to as providing an "atomizer"), and an aerosol precursor (e.g., a composition that commonly is a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the aerosol generation piece such that aerosol generated can be withdrawn therefrom upon draw by a user).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

Alignment of the components within the aerosol delivery device can vary. In specific embodiments, the aerosol precursor composition can be located near an end of the article (e.g., within a cartridge, which in certain circumstances can be replaceable and disposable), which may be configured to be positioned proximal to the mouth of a user so as to maximize aerosol delivery to the user. Other configurations, however, are not excluded. Generally, the components can be configured relative to one another so that heat from the heating element can volatilize the aerosol precursor composition (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof.

An aerosol delivery device incorporates a battery or other electrical power source to provide current flow sufficient to provide various functionalities to the article, such as powering of a heater, powering of control systems, powering of indicators, and the like. The power source can take on various embodiments. Preferably, the power source is able to deliver sufficient power to rapidly heat the heating element to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

An aerosol delivery device can include a cartridge and a control body that can be permanently or detachably aligned in a functioning relationship. Various embodiments of engagement between the cartridge and the control body may be employed such as a threaded engagement, a press-fit engagement, an interference fit, a magnetic engagement, or the like. The aerosol delivery device may be substantially rod-like, substantially tubular shaped, or substantially cylindrically shaped in some embodiments when the cartridge and the control body are in an assembled configuration.

In specific embodiments, one or both of the cartridge and the control body may be referred to as being disposable or as being reusable. For example, the control body may have a replaceable battery or a rechargeable battery and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge may comprise a single-use cartridge, as disclosed in U.S. Pat. Pub. No. 2014/0060555 to Chang et al., which is incorporated herein by reference in its entirety.

In some embodiments a cartridge may include a base that may comprise anti-rotation features that substantially prevent relative rotation between the cartridge and the control body as disclosed in U.S. Pat. App. Pub. No. 2014/0261495 to Novak et al., which is incorporated herein by reference in its entirety.

An aerosol delivery device may include a component configured to hold an aerosol precursor composition. The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al.; U.S. Pat. No. 5,101,839 to Jakob et al.; U.S. Pat. Pub. No. 2013/0008457 to Zheng et al.; PCT WO 98/57556 to Biggs et al.; and Chemical and Biological Studies on New Cigarette Prototypes that Heat Instead of Burn Tobacco, R. J. Reynolds Tobacco Company Monograph (1988); the disclosures of which are incorporated herein by reference in their entireties.

A variety of heater components may be used in the present aerosol delivery device. In various embodiments, one or more microheaters or like solid state heaters may be used. Embodiments of microheaters that may be utilized are further described herein. Further microheaters and atomizers incorporating microheaters suitable for use in the presently disclosed devices are described in U.S. Pat. Pub. No. 2014/0060554 to Collett et al., which is incorporated herein by reference in its entirety. In some embodiments a heating element may be formed by winding a wire about a liquid transport element as described in U.S. Pat. App. Pub. No. 2014/0157583 to Ward et al., which is incorporated herein by reference in its entirety. Further, in some embodiments the wire may define a variable coil spacing, as described in U.S. Pat. App. Pub. No. 2014/0270730 to DePiano et al., which is incorporated herein by reference in its entirety. Various embodiments of materials configured to produce heat when electrical current is applied therethrough may be employed to form a resistive heating element. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic). In further embodiments a stamped heating element may be employed in the atomizer, as described in U.S. Pat. App. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. Pub. No. 2014/0060554 to Collett et al., which is incorporated herein by reference, as noted above.

In some embodiments the aerosol delivery devices of the present disclosure may include a control body and a cartridge. When the control body is coupled to the cartridge, an electrical control component in the cartridge may form an electrical connection with the control body. The control body may thus employ the electronic control component to determine whether the cartridge is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on a mouthpiece of the cartridge of the aerosol delivery device. This may pull air through an opening in the control body or in the cartridge. For example, in one embodiment an opening may be defined between the coupler and the outer body of the control body, as described in U.S. Pat. App. Pub. No. 2014/0261408 to DePiano et al., which is incorporated herein by reference in its entirety. However, the flow of air may be received through other parts of the aerosol delivery device in other embodiments.

A sensor in the aerosol delivery device (e.g., a puff or flow sensor in the control body) may sense the puff. When the puff is sensed, the control body may direct current to the heater through a circuit. Accordingly, the heater may vaporize the aerosol precursor composition, and the mouthpiece may allow passage of air and entrained vapor (i.e., the components of the aerosol precursor composition in an inhalable form) from the cartridge to a consumer drawing thereon.

Various other details with respect to the components that may be included in the cartridge, are provided, for example, in U.S. Pat. App. Pub. No. 2014/0261495 to Novak et al., which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heater terminals of an atomizer in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow tube, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 11 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 20 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 21 thereof illustrates a perspective view of a base with an anti-rotation mechanism; FIG. 22 thereof illustrates a perspective view of a coupler with an anti-rotation mechanism; and FIG. 23 thereof illustrates a sectional view through the base of FIG. 21 thereof and the coupler of FIG. 22 thereof in an engaged configuration.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. Pub. No. 2014/0000638 to Sebastian et al., which is incorporated herein by reference in its entirety.

In the present disclosure, FIG. 1 illustrates an exploded view of a control body 300 of an aerosol delivery device according to an example embodiment. As illustrated, the control body 300 may comprise a coupler 302, an outer body 304, a sealing member 306, an adhesive member 308 (e.g., KAPTON® tape), a flow sensor 310 (e.g., a puff sensor or pressure switch), a control component 312, a spacer 314, an electrical power source 316 (e.g., a battery, which may be rechargeable), a circuit board with an indicator 318 (e.g., a light emitting diode (LED)), a connector circuit 320, and an end cap 322. Examples of electrical power sources are described in U.S. Pat. App. Pub. No. 2010/0028766 by Peckerar et al., the disclosure of which is incorporated herein by reference in its entirety. An exemplary mechanism that can provide puff-actuation capability includes a Model 163PC01D36 silicon sensor, manufactured by the Micro-Switch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present aerosol delivery device, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties. Reference also is made to the control schemes described in U.S. App. Pub. No. 2014/0270727 to Ampolini et al., which is incorporated herein by reference in its entirety.

In one embodiment the indicator 318 may comprise one or more light emitting diodes. The indicator 318 can be in communication with the control component 312 through the connector circuit 320 and illuminate, for example, during a user drawing on a cartridge coupled to the coupler 302, as detected by the flow sensor 310. The end cap 322 may be adapted to make visible the illumination provided thereunder by the indicator 318. Accordingly, the indicator 318 may illuminate during use of the aerosol delivery device to simulate the lit end of a smoking article. However, in other embodiments the indicator 318 can be provided in varying numbers and can take on different shapes and can even be an opening in the outer body (such as for release of sound when such indicators are present).

Still further components can be utilized in the aerosol delivery devices of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat.

No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al. and U.S. Pat. No. 8,851,083 to Oglesby et al.; U.S. Pat. App. Pub. Nos. 2006/0196518 and 2009/0188490 to Hon; U.S. Pat. App. Pub. Nos. 2009/0260641 and 2009/0260642 to Monsees et al.; U.S. Pat. App. Pub. No. 2010/0024834 to Oglesby et al.; U.S. Pat. App. Pub. No. 2010/0307518 to Wang; U.S. Pat. App. Pub. No. 2014/0261408 to DePiano et al.; WO 2010/091593 to Hon; WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

Accordingly, example embodiments of aerosol delivery devices are described above. However, the present disclosure provides various other embodiments of aerosol delivery devices. As described hereinafter, such aerosol delivery devices may include differing configurations of components for storing, delivering, and/or vaporizing an aerosol precursor composition. Some of the components of the aerosol delivery devices may be substantially similar to the components described above, and hence details with respect to these components and the function thereof will not be repeated or only briefly described. However, it should be understood that the description of components provided above is equally applicable to the embodiments of aerosol delivery devices described hereinafter unless otherwise noted.

In this regard, FIG. 2 illustrates an exploded view of an aerosol delivery device 1200 according to an additional example embodiment of the present disclosure. As illustrated, the aerosol delivery device 1200 may include a control body 1202 and a cartridge 1204. The control body 1202 may include an end cap 1206, a circuit board with an indicator 1208 (e.g., a light emitting diode (LED)), a connector circuit 1209, an electrical power source 1210 (e.g., a battery, which may be rechargeable), a flow sensor 1212, a coupler 1214, and an outer body 1216 (which may include one or more inlet apertures 1233). The cartridge 1204 may include a base 1218, a combined dispenser and atomizer assembly 1220, a reservoir 1222, a lid 1224, a mouthpiece 1226, and an outer body 1228.

FIG. 3 illustrates a modified sectional view through the aerosol delivery device 1200 of FIG. 2. As illustrated therein, the base 1218 of the cartridge 1204 may be configured to engage the coupler 1214 of the control body 1202 to form a mechanical and electrical connection therebetween. The connection between the base 1218 of the cartridge 1204 and the coupler 1214 of the control body 1202 may be releasable such that, for example, the cartridge may be replaced when an aerosol precursor composition 1246 (see, FIG. 6) received therein is expended. Although FIG. 2 illustrates wiring 1230 as being coupled to the base 1218, the wiring may actually be coupled to the coupler 1214 so as to allow for releasable connection between the cartridge 1204 and the control body 1202 in some embodiments.

FIG. 3 further illustrates a flow path of air through the aerosol delivery device 1200 when a user draws on the mouthpiece 1226. As illustrated, an airflow or flow of ambient air 1232 may enter the aerosol delivery device 1200 through the one or more inlet apertures 1233 and travel proximate or past the flow sensor 1212. The air 1232 may then travel through at least one coupler aperture 1261 in the coupler 1214 and at least one base aperture 1263 in the base 1218, around the combined dispenser and atomizer assembly 1220 and the reservoir 1222 (e.g., via one or more aerosol delivery apertures 1265 defined in the outer body 1228 or a space between the reservoir and the outer body), and out the mouthpiece 1226.

The inlet apertures 1233 may be defined in the outer body 1216 of the control body 1202 such that the flow sensor 1212, which may also be positioned in the control body, may detect flow of the air 1232. The control body 1202 may be reusable, whereas the cartridge 1204 may be disposable. In this regard, whereas certain components within the cartridge 1204 may degrade or be depleted, the flow sensor 1212 and other components within the control body may maintain full functionality despite repeated use. Accordingly, positioning the flow sensor 1212 in the control body 1202 and providing a corresponding flow path of the air 1232 through the control body, or otherwise providing for fluid communication of the air traveling through the aerosol delivery device 1200 with the flow sensor, may decrease the cost of the cartridge 1204 by decreasing the number and type of components received therein. In this regard, although airflow is generally described as occurring through the control body in this and other embodiments disclosed herein, in additional embodiments a pressure tap may be employed to allow a flow sensor in a control body to detect a flow of air through a cartridge substantially without any airflow through the control body as described, for example, in U.S. patent application Ser. No. 14/193,961, filed Feb. 28, 2014, to Worm et al., which is incorporated herein by reference in its entirety.

The lid 1224 and the combined dispenser and atomizer assembly 1220 may be coupled to opposing ends of the reservoir 1222. Accordingly, the lid 1224 and the combined dispenser and atomizer assembly 1220 may enclose the reservoir 1222 and retain the aerosol precursor composition 1246 (see, FIG. 6) therein. However, when the flow sensor 1212 detects the puff, the combined dispenser and atomizer assembly 1220 may be actuated such that the aerosol precursor composition 1246 (see, FIG. 6) is controllably dispensed from the reservoir 1222.

In this regard, FIG. 4 illustrates a partial sectional view through the combined dispenser and atomizer assembly. As illustrated, in one embodiment the combined dispenser and atomizer assembly 1220 may include a bubble jet head 1234 and an atomizer 1238 fixedly coupled thereto. As discussed in detail below, the bubble jet head 1234 may be configured to dispense the aerosol precursor composition 1246 from the reservoir 1222 (see, e.g., FIG. 6). Further, the atomizer 1238 may be configured to heat the aerosol precursor composition 1246 to produce an aerosol or vapor 1248 (see, FIG. 6).

The bubble jet head 1234 may include one or more precursor inlets 1245, one or more precursor channels 1235, one or more first or ejection heating elements 1240, one or more precursor nozzles 1242, and a wafer, substrate, or housing 1241 respectively associated therewith. In some embodiments the housing 1241 may comprise silicon, ceramic, graphite, or other lower thermally-conductive and/or insulating materials. The precursor inlets 1245, the precursor channels 1235, and/or precursor nozzles 1242 may be defined by apertures in the housing 1241 in some embodiments. Alternatively, the precursor inlets, the precursor channels, and/or the precursor outlets may comprise separate elements coupled to the housing. Further, the ejection heating elements 1240 may be positioned within one or more first or ejection chambers 1237, which may be defined by the housing 1241 of the bubble jet head 1234. In some embodiments the bubble jet head 1234 may comprise a standard inkjet printer head (e.g., a standard bubble jet print head sold by ImTech of Corvallis, Oregon or a 45 style jet head sold by Hewlett Packard of Palo Alto, California).

The atomizer 1238 may be positioned relative to the bubble jet head 1234 so as to receive the aerosol precursor composition 1246 dispensed from the reservoir 1222 (see, FIG. 6). In some embodiments the atomizer 1238 may be fixedly coupled to the bubble jet head 1234 such that the combined dispenser and atomizer assembly 1220 may be inserted into the outer body 1228 of the cartridge 1204 (see, e.g., FIG. 3) as a unit, rather than separately inserted into the outer body. By way of example, the combined dispenser and atomizer assembly 1220 may be engaged with the reservoir 1222 and the combined assembly may be inserted into the outer body 1228 (see, e.g., FIG. 3). Further, fixedly coupling the bubble jet head 1234 to the atomizer 1238 may allow for precise placement of these two components relative to one another such that the dispensed aerosol precursor composition 1246 (see, FIG. 6) is received at a proper location on the atomizer for atomization.

As illustrated in FIG. 4, in one embodiment the bubble jet head 1234 may be fixedly coupled to the atomizer 1238 via one or more spacers 1236. In particular, the atomizer 1238 may include a wafer, substrate, or housing 1243 that is coupled to the housing 1241 of the bubble jet head 1234 via the spacers 1236. In some embodiments the housing 1243 may comprise silicon, ceramic, graphite, or other nonconductive and/or insulating materials. The spacers 1236 may be configured to provide a gap between the bubble jet head 1234 and the atomizer 1238. In some embodiments the gap may be from about 1 mm to about 10 mm, and more preferably from about 1 mm to about 3 mm in order to reduce splattering of the aerosol precursor composition. However, gaps defining differing dimensions may be employed in other embodiments. In this regard, the gap between the bubble jet head 1234 and the atomizer 1238 may be selected or adjusted to provide accurate delivery of the aerosol precursor composition to the heating surface of the atomizer based on a droplet dispersion pattern associated with ejection of the aerosol precursor composition from the bubble jet head (e.g., to prevent pooling of the aerosol precursor composition on one or more portions of the atomizer, to provide a thin, even film of the aerosol precursor composition across the heating surface of the atomizer, and/or to target a specific region of the atomizer). The atomizer 1238 may further include one or more second or vaporization heating elements 1244. For example, a respective one of the vaporization heating elements 1244 may be associated with each ejection heating element 1240 and each nozzle 1242.

The bubble jet head 1234 may be coupled to the reservoir 1222 or otherwise positioned in fluid communication therewith. For example, as illustrated in FIG. 5, in some embodiments the bubble jet head 1234 may be coupled to a distal end 1222A of the reservoir 1222 so as to block an opening 1222' to the reservoir and retain the aerosol precursor composition 1246 (see, FIG. 6) therein as described above. Thus, the precursor inlets 1245 in the bubble jet head 1234 may be in fluid communication with the reservoir 1222 and thereby the precursor channels 1235 may direct the aerosol precursor composition 1246 (see, FIG. 6) to the ejection chambers 1237 in which the ejection heating elements 1240 are positioned.

Coupling the bubble jet head 1234 to the distal end 1222A of the reservoir 1222 may be advantageous in that it provides a relatively simple mechanism for attachment and fluid coupling. In this regard, the reservoir 1222 may define a hollow, substantially cylindrical configuration, and the distal end 1222A may define a substantially planar configuration. Thereby, the bubble jet head 1234 may be coupled (e.g., glued, adhered, or welded) to the distal end 1222A of the reservoir 1222 to enclose the reservoir and provide fluid communication between the reservoir and the bubble jet head.

Accordingly, the bubble jet head 1234 may receive the aerosol precursor composition 1246 (see, FIG. 6) from the reservoir 1222. In some embodiments, as illustrated in FIG. 5, the reservoir 1222 may include a reservoir substrate 1239 configured to direct the aerosol precursor composition 1246 (see, FIG. 6) to the bubble jet head 1234. In this regard, the reservoir substrate 1239 may comprise any material configured to wick or otherwise transport the aerosol precursor composition 1246 (see, FIG. 6) to the bubble jet head 1234, such as cellulose acetate, polyethylene terephthalate (PET), or any polymeric material, whether woven or nonwoven and whether fibrous or nonfibrous. Further, in other embodiments the reservoir substrate 1239 may comprise one or more nonpolymeric materials that may be manufactured as an open cell foam or the like (e.g., ceramic foam, carbon foam, sintered glass), such that the material(s) define a porous media that provides wicking channels. Accordingly, by employing the reservoir substrate 1239, the aerosol precursor composition 1246 (see, FIG. 6) may be directed to the bubble jet head 1234 regardless of the orientation of the aerosol delivery device 1200 (see, e.g., FIG. 2), such that the aerosol delivery device does not have to be oriented in a particular manner during usage. In some embodiments the reservoir substrate may occupy only a portion of the longitudinal length of the reservoir. For example, the reservoir substrate may only be positioned proximate the distal end of the reservoir to which the bubble jet head is attached. This configuration may provide substantially the same benefits noted above, because movement of the aerosol delivery device may cause the aerosol precursor composition to contact the reservoir substrate, while reducing the volume within the reservoir occupied by the reservoir substrate so as to allow for a greater fluid capacity therein.

The aerosol precursor composition 1246 (see, FIG. 6) may initially be prevented from traveling through the remainder of the combined dispenser and atomizer assembly 1220 by the precursor nozzles 1242. In this regard, the precursor nozzles 1242 may be appropriately sized to resist flow therethrough due to, for example, surface tension. Alternatively or additionally, a negative pressure in the reservoir (e.g., as created by a spring and a piston within the reservoir or as a result of applying a negative pressure to the reservoir prior to sealing it shut, may resist passive leakage of the aerosol precursor composition out of the reservoir and through the bubble jet head.

However, when a puff is detected by the flow sensor 1212, the bubble jet head 1234 may direct the aerosol precursor composition 1246 (see, FIG. 6) in the reservoir 1222 toward the atomizer 1238. In particular, current from the power source 1210 (see, e.g., FIG. 2) may be directed to the ejection heating elements 1240 to heat the aerosol precursor composition 1246 (see, FIG. 6) received through the precursor inlets 1245 and the precursor channels 1235 such that bubbles of vapor form, which eject droplets of the aerosol precursor composition through the precursor nozzles 1242 toward the atomizer 1238, as described and illustrated in greater detail below with respect to alternative embodiments of the present disclosure.

Current from the power source 1210 (see, e.g., FIG. 2) may be applied to the vaporization heating elements 1244 prior to, simultaneously with, or after applying current to the ejection heating elements 1240. However, delaying application of the current to the vaporization heating elements 1244 until after the ejection heating elements 1240 receive current may assist in preventing wasted energy. In this regard, some of the heat produced by the vaporization heating elements 1244 prior to the aerosol precursor composition 1246 (see, FIG. 6) coming in contact therewith may be undesirably transferred to surrounding portions of the aerosol delivery device 1200 or air within the aerosol delivery device, rather than applied to the aerosol precursor composition as desired.

In one embodiment a plurality of walls defined by the housing 1241 of the bubble jet head 1234, the spacers 1236, and/or the housing 1243 of the atomizer 1238 may cooperatively define a second or vaporization chamber 1247 (see, e.g., FIG. 4) in which the vaporization heating elements 1244 are positioned and to which the aerosol precursor composition 1246 (see, FIG. 6) is delivered. Thus, issues with respect to the aerosol precursor composition 1246 (see, FIG. 6) being directed into the air 1232 and to a user without being vaporized may be avoided. In this regard, the aerosol precursor composition 1246 may be directed into contact with the vaporization heating elements 1244 at the vaporization chamber 1247 to ensure vaporization thereof, prior to being directed into the flow of air 1232 through the aerosol delivery device 1200. As illustrated in FIG. 6, the flow of air 1232 may extend generally around the combined dispenser and atomizer assembly 1220, rather than flow between the bubble jet head 1234 and the atomizer 1238 such that the flow of air does not direct the aerosol precursor composition away from the atomizer prior to atomization. Note that if the aerosol precursor composition were to be directed into the air without being vaporized, the aerosol precursor composition may separate from the air and accumulate in the aerosol delivery device at a location outside of the reservoir. This could result in undesirable fluid leakage from the aerosol delivery device. Alternatively or additionally, the liquid aerosol precursor composition could reach the user's mouth, which may cause an undesirable taste or sensation.

Thereby, the droplets of the aerosol precursor composition 1246 ejected from the nozzles 1242 may be vaporized by the vaporization heating elements 1244 of the atomizer 1238 to produce an aerosol or vapor 1248 (see, FIG. 6). As illustrated in FIG. 6, the vapor 1248 produced by the vaporization heating elements 1244 may then exit the combined dispenser and atomizer assembly 1220 and intermix and travel with the air 1232 to the mouthpiece 1226. Accordingly, the bubble jet head 1234 may be employed to precisely dispense the aerosol precursor composition 1246 (see, FIG. 6) to the atomizer 1238, which may provide advantages in terms of ensuring that there is a consistent amount of aerosol delivered with each draw on the aerosol delivery device 1200 as compared to embodiments of aerosol delivery devices that rely on passive aerosol precursor composition delivery mechanisms such as wicks.

The electrical power directed to the bubble jet head 1234 and the atomizer 1238 from the power source 1210 may be controlled in one or more manners. For example, the power directed to the bubble jet head 1234 may be independently controlled relative to the atomizer 1238 in one or more manners. Further, pulse width and/or pulse amplitude modulation may be employed to provide an appropriate amount of current to the bubble jet head 1234 and the atomizer 1238. Relatively larger pulse widths and/or amplitudes may be employed to produce a relatively larger amount of heat. In this regard, the ejection heating elements 1240 may have a relatively lower thermal mass and may be configured to heat the aerosol precursor composition 1246 to a relatively lesser degree than the vaporization heating elements 1244 in order to eject and dispense the aerosol precursor composition, rather than fully vaporize the aerosol precursor composition, which occurs at the atomizer 1238. In this regard, while ejection of the aerosol precursor composition may involve vaporization, only a small portion of the aerosol precursor composition is vaporized and the vaporization occurs in the substantially enclosed ejection chamber 1237 such that one or more droplets of the aerosol precursor composition are ejected therefrom. In contrast, the vaporization heating elements may be configured to vaporize an entirety of the aerosol precursor composition directed thereto. Thus, in order to heat the ejection heating elements 1240 to a relatively lesser degree than the vaporization heating elements 1244, relatively smaller pulse widths and/or amplitudes of power may be directed to the ejection heating elements as compared to the pulse widths and/or amplitudes of power directed to the vaporization heating elements. Further, the application of power to the vaporization heating elements 1244 may be delayed in relation to application of power to the ejection heating elements 1240, such that energy is not wasted at the vaporization heating elements prior to ejection of the aerosol precursor composition.

As noted above, in one embodiment the bubble jet head may comprise a substantially conventional bubble jet head, such as an ink jet head employed in a printer. However, the ink jet head may be modified for use in the aerosol delivery devices of the present disclosure. For example, the number of precursor nozzles and precursor inlets leading thereto may be adjusted, the diameter and/or shape of the precursor inlets and/or the precursor nozzles may be adjusted, the size of the ejection heating elements in the bubble jet head may be adjusted, the heat outputted by the ejection heating elements may be adjusted, the pulse width of power applied to the ejection heating elements in the bubble jet head may be adjusted, and/or various other characteristics may be adjusted. These changes may accommodate the differences in viscosity of the aerosol precursor composition versus ink as well as the goal of directing the aerosol precursor composition at an atomizer to vaporize the aerosol precursor composition, as opposed to printing ink on a substrate such as paper.

The present disclosure provides various additional embodiments of aerosol delivery devices including bubble jet heads configured to dispense an aerosol precursor composition to an atomizer. For brevity purposes, description with respect to certain features and components of the aerosol delivery devices that are described above will not be repeated below in detail. However, it should be understood that the description provided above is applicable to the embodiments of aerosol delivery devices described below, except where otherwise indicated.

FIG. 7 illustrates a sectional view through an aerosol delivery device 1300 according to an additional example embodiment of the present disclosure. As illustrated, the aerosol delivery device 1300 may include a control body 1302 and a cartridge 1304. The control body 1302 may include an end cap 1306, a flow sensor 1308, an electrical power source 1310 (e.g., a battery, which may be rechargeable), a coupler 1312 defining at least one coupler aperture 1361, and an outer body 1314. The control body may additionally include a circuit board with an indicator (e.g., a light emitting diode (LED)) and a connector circuit as described elsewhere herein. The cartridge 1304 may include a base 1316 defining at least one base aperture 1363, a combined dispenser and atomizer assembly 1318, a reservoir 1320, a lid 1322 that encloses the reservoir, a mouthpiece 1324, and an outer body 1326 defining one or more aerosol delivery apertures 1365. The base 1316 of the cartridge 1304 may be configured to engage the coupler 1312 of the control body 1302 to form a mechanical and electrical connection therebetween, which may be releasable to allow for replacement of the cartridge.

FIG. 8 illustrates a sectional view through the aerosol delivery device 1300 showing a flow path of air through the aerosol delivery device when a user draws on the mouthpiece 1324. As illustrated, an airflow or flow of ambient air 1328 may enter the aerosol delivery device 1300 through one or more inlet apertures 1331 and travel past or proximate the flow sensor 1308 and around the electrical power source 1310. Although the ambient air 1328 is illustrated as flowing around the electrical power source 1310, in other embodiments the air may not flow past the electrical power source and/or the flow sensor may be positioned at an alternative location. Further, the inlet apertures 1331 may be positioned at various alternate locations and defined in other components, such as in the outer body 1314 of the control body 1302 between the electrical power source 1310 and the coupler 1312. The air 1328 may flow from the control body 1302 through the aperture 1361 in the coupler 1312 and into and through the base aperture 1363 in the base 1316, around the combined dispenser and atomizer assembly 1318 and the reservoir 1320 (e.g., via the aerosol delivery apertures 1365 defined in the outer body 1326 or between the reservoir and the outer body), and out the mouthpiece 1324.

When the flow sensor 1308 detects the puff, the combined dispenser and atomizer assembly 1318 may be activated. In this regard, as illustrated in the partial sectional view of FIG. 9, the combined dispenser and atomizer assembly 1318 may receive an aerosol precursor composition 1330 from the reservoir 1320 and produce an aerosol or vapor 1332. More particularly, as illustrated in the enlarged partial sectional view of FIG. 10, the combined dispenser and atomizer assembly 1318 may include a wafer, substrate, or housing 1333 defining at least one precursor inlet 1334 through which the aerosol precursor composition 1330 is received. The aerosol precursor composition 1330 may then travel through one or more precursor channels 1335 to one or more precursor nozzles 1336. In some embodiments the precursor inlet 1334, the precursor channels 1335, and/or the precursor nozzles 1336 may be defined by the housing 1333. Alternatively, the precursor inlets, the precursor channels, and/or the precursor outlets may comprise separate components coupled to the housing. The aerosol precursor composition 1330 may initially be prevented from traveling through the remainder of the combined dispenser and atomizer assembly 1318 by the precursor nozzles 1336 leading thereto. In this regard, the precursor nozzles 1336 may be appropriately sized to resist flow therethrough due to, for example, surface tension. Alternatively or additionally, the aerosol precursor composition may be exposed to a negative pressure within the reservoir as discussed above to reduce the likelihood of fluid leakage through the combined dispenser and atomizer assembly.

However, when the flow sensor 1308 (see, e.g., FIG. 8) detects the puff on the aerosol delivery device 1300, current may be directed from the power source 1310 (see, e.g., FIG. 8) to one or more first or ejection heating elements 1338 positioned within a first or ejection chamber 1339 defined by the housing 1333. Thereby, the ejection heating elements 1338 may heat the aerosol precursor composition 1330 such that the aerosol precursor composition 1330 boils and bubbles of vapor 1340 form. Each bubble of vapor 1340 expands extremely rapidly, creating a pressure pulse that then causes a droplet 1342 of the aerosol precursor composition 1330 to eject through a respective one of the precursor nozzles 1336. After the application of power to the ejection heating element 1338 ends, the bubble of vapor 1340 collapses as the aerosol precursor composition 1330 and the bubble of vapor 1340 cools. Surface tension and surface energy associated with the aerosol precursor composition 1330 at the precursor nozzle 1336 and capillary forces due to interaction of aerosol precursor composition with the microfluid channel defined by the precursor inlet 1334, the precursor channels 1335, and the precursor nozzles may cause more of the aerosol precursor composition to be directed from the reservoir toward the ejection heating element 1338, such that the aerosol precursor composition replenishes the ejection chamber 1337 and such that the ejection cycle may be repeated. Thus, use of a separate valve may not be required to dispense the aerosol precursor composition 1330. Accordingly, the combined bubble jet head and dispenser 1318 may comprise a bubble jet head 1350 including the ejection heating elements 1338, the precursor inlets 1334, the precursor channels 1335, and the precursor nozzles 1336.

As further illustrated in FIG. 10, the droplets 1342 of the aerosol precursor composition 1330 may be ejected through the precursor nozzles 1336 toward one or more second or vaporization heating elements 1344. In this regard, each ejection heating element 1338, precursor nozzle 1336, and vaporization heating element 1344 of a respective portion of the combined dispenser and atomizer assembly 1318 may be axially aligned such that aerosol precursor composition 1330 is ejected onto the vaporization heating elements. The vaporization heating elements 1344 may be positioned in a second or vaporization chamber 1346 defined by the housing 1333 and to which droplets 1342 of the aerosol precursor composition 1330 are delivered. A respective one of the vaporization heating elements 1344 may be associated with each ejection heating element 1338 and each of the precursor nozzles 1336. Thereby, the droplets 1342 of the aerosol precursor composition 1330 ejected from the precursor nozzles 1336 may be vaporized by the vaporization heating elements 1344 to produce the vapor 1332 (see, e.g., FIG. 9).

In this regard, the ejection heating elements 1338 may have a relatively lower thermal mass and may be configured to heat the aerosol precursor composition 1330 to a relatively lesser degree as compared to the vaporization heating elements 1344. The vapor 1332 (see, e.g., FIG. 9) produced by the vaporization heating elements 1344 may then exit the combined dispenser and atomizer assembly 1318 through one or more aerosol outlets 1348, which may be defined by the housing 1333 at the second chamber 1346. In order to cause the vapor 1332 to exit through the aerosol outlets 1348, rather than travel backwards through the precursor nozzles 1336, the aerosol outlets may define a larger area than an area of the precursor nozzles. Further, by providing the aerosol outlets 1348 with a relatively larger area and/or providing the second chamber 1346 with a relatively large volume, issues with respect to the rapid expansion of the aerosol precursor composition 1330 into the vapor 1332 (see, e.g., FIG. 9) causing damage to the combined dispenser and atomizer assembly 1318 may be avoided.

As illustrated in FIG. 11, the vapor 1332 may intermix and travel with the air 1328 toward the mouthpiece 1324 (see, e.g., FIG. 8). For example, the vapor 1332 and the air 1328 may travel through the aerosol delivery apertures 1365 defined in the outer body 1326 of the cartridge 1304. As described above, the aerosol precursor composition may be ejected into, and vaporized within, the vaporization chambers 1346. Thereby, issues with respect to the aerosol precursor composition being directed into the air 1328 (see, e.g., FIG. 8) without first being atomized may be avoided.

Accordingly, the combined dispenser and atomizer assembly 1318 of FIGS. 7-11 may be an integral unit (e.g., provided as a silicon chip) including both the bubble jet head 1350 (e.g., comprising the ejection heating elements 1338, the precursor inlets 1334, the precursor channels 1335, and the precursor nozzles 1336) and an atomizer 1352 (e.g., comprising the aerosol outlets 1348 and the vaporization heating elements 1344) fixedly coupled to one another via the housing 1333, which is configured for receipt within the outer body 1326 of the cartridge 1304 (see, e.g., FIG. 8). In contrast, the combined dispenser and atomizer assembly 1220 illustrated in FIGS. 2-6 may include a standard bubble jet head 1234 (e.g., a bubble jet head from an inkjet printer) which may be fixedly coupled to an atomizer 1238 (e.g., via the spacers 1236) and modified to act as a dispenser for dispensing an aerosol precursor composition to the atomizer.

FIG. 12 illustrates a sectional view through an aerosol delivery device 1400 according to an additional example embodiment of the present disclosure. As illustrated, the aerosol delivery device 1400 may include a control body 1402 and a cartridge 1404, which are illustrated in a decoupled configuration. The control body 1402 may include an end cap 1406, a circuit board with an indicator 1408 (e.g., a light emitting diode (LED)), a connector circuit 1409, an electrical power source 1410 (e.g., a battery, which may be rechargeable), a flow sensor 1411 (e.g., a puff sensor or pressure switch), a coupler 1412, wiring 1413, and an outer body 1414. The cartridge 1404 may include a base 1416, a combined dispenser and atomizer assembly 1418, a reservoir 1420, a lid 1422 that encloses the reservoir, a mouthpiece 1424, and an outer body 1426. The base 1416 of the cartridge 1404 may be configured to engage the coupler 1412 of the control body 1402 to form a mechanical and electrical connection therebetween, which may be releasable to allow for replacement of the cartridge.

FIG. 13 illustrates an enlarged partial sectional view of the aerosol delivery device 1400 wherein the control body 1402 and the cartridge 1404 are coupled to one another. As illustrated, the combined dispenser and atomizer assembly 1418 may comprise a bubble jet head 1450 and an atomizer 1452. The bubble jet head 1450 and the atomizer 1452 may comprise any of the components and features of the bubble jet heads and atomizers described elsewhere herein.

As further illustrated in FIG. 13, the bubble jet head 1450 and the atomizer may be coupled via a flexible circuit 1453. In particular, the flexible circuit 1453 may be electrically coupled to the base 1416 such that the dispenser and atomizer assembly 1418 is electrically connected to the cartridge 1402 through the base and the coupler 1412. The flexible circuit 1453 may additionally electrically couple the bubble jet head 1450 to the atomizer 1452 such that power may be directed to the bubble jet head and the atomizer in the manners described elsewhere herein.

Further, in some embodiments the flexible circuit may mechanically couple the bubble jet head 1450 to the atomizer 1452 such that the bubble jet head and the atomizer are fixedly coupled to one another. In this regard, the flexible circuit 1453 may comprise a high temperature polyamide substrate or other flexible, nonconductive material with a circuit printed, etched, or otherwise formed thereon. Further, in some embodiments the combined dispenser and atomizer assembly 1418 may be coupled to the reservoir 1420 and then this assembly may be inserted into the outer body 1426 of the cartridge 1404. In this regard, the mechanical coupling between the bubble jet head 1450 and the atomizer 1452 via the flexible circuit 1453 may allow for insertion in this manner. Further, the flexible circuit 1453 may be configured to flex such that, for example, the combined dispenser and atomizer assembly 1418 may be pressed against the base 1416 to define a desired gap or separation between the bubble jet head 1450 and the atomizer 1452. In this regard, for example, the flexible circuit 1453 may initially position the bubble jet head 1450 and the atomizer 1452 at a relatively large separation and the flexible circuit may flex during assembly for example, as a result of contact with the base 1416 to define the desired separation.

As further illustrated in FIG. 13, in some embodiments the outer body 1414 of the control body 1402 may define one or more inlet apertures 1431, the coupler 1412 may define at least one coupler aperture 1427, the base 1416 may define at least one base aperture 1429, and the outer body 1426 of the cartridge 1404 may define at least one aerosol delivery aperture 1465, which may allow flow of air through the aerosol delivery device 1400. In this regard, FIG. 14 illustrates a sectional view through the aerosol delivery device 1400 showing a flow path of air through the aerosol delivery device when a user draws on the mouthpiece 1424. As illustrated, an airflow or flow of ambient air 1428 may enter the aerosol delivery device 1400 through the inlet apertures 1431 which may be defined in the outer body 1414 of the control body 1402 and travel past or proximate the flow sensor 1411. The air 1428 may flow from the control body 1402 through the coupler 1412 at the coupler aperture 1427 (see, FIG. 13) and through the base aperture 1429 defined in the base 1416 of the cartridge 1404, through and/or around the combined dispenser and atomizer assembly 1418, around the reservoir 1420 (e.g., through the aerosol delivery aperture 1465 defined in the outer body 1426 or between the reservoir and the outer body, as illustrated in FIG. 15), and out the mouthpiece 1424. Note that although the aerosol delivery aperture 1465 is illustrated as defining a nonlinear flow path, in other embodiments the aerosol delivery aperture may define a linear flow path (e.g., extending parallel to the longitudinal length of the cartridge) in order to simplify manufacturing of the cartridge and provide a flow path with a smaller pressure drop.

In particular, the air 1428 may travel through the base 1416 via the at least one base aperture 1429 (see, FIG. 13). As illustrated in FIG. 13, the base aperture 1429 may be positioned proximate a radially outer edge of the base 1412. Thereby, as illustrated in FIG. 14, the air 1428 may enter the cartridge proximate an inner surface of the outer body 1426. The air 1428 may flow around and partially through the combined dispenser and atomizer assembly 1418 between the bubble jet head 1450 and the atomizer 1452 (see, FIG. 13).

When the flow sensor 1411 detects the puff, the combined dispenser and atomizer assembly 1418 may be activated such that the bubble jet head 1450 ejects the aerosol precursor composition from the reservoir 1420 toward the atomizer 1452 (see, FIG. 13). Although the above-described configuration of the flow of at least part of the air 1428 through the combined dispenser and atomizer assembly 1418 may result in the aerosol precursor composition being ejected into the flow of air 1428 prior to atomization, usage of the base aperture 1429 may regulate flow of the air through the combined dispenser and atomizer assembly such that substantially all of the aerosol precursor composition may come into contact with the atomizer 1452 (see, FIG. 13) and become atomized, rather than become entrained with the air in liquid form and thereafter potentially separate therefrom. Further, some of the air 1428 may flow around, rather than through, the combined dispenser and atomizer assembly 1418, such that the flow of the air may be distributed across a relatively large area and thereby the flow of the air through the combined dispenser and atomizer assembly may define a relatively low velocity which may not affect dispensing of the aerosol precursor composition onto the atomizer 1452 (see, FIG. 13) to a great extent. Additionally, the flexible circuit 1453 and/or housings of the bubble jet head 1450 and the atomizer 1452 may define a vaporization chamber that further resists directing the aerosol precursor composition into the flow of air 1428 without being atomized. In some embodiments the atomizer may be shifted downstream of the bubble jet head to account for movement of the aerosol precursor composition caused by the flow of air. Following atomization, the air and vapor may travel around the reservoir 1422 and out the mouthpiece 1424 to the user. Note that the embodiments of the aerosol delivery device including a flex circuit may be configured to avoid issues with respect to liquid aerosol precursor composition becoming entrained with air without being vaporized. In this regard, for example, the bubble jet head and the atomizer may be spaced relatively close to one another and the atomizer may be heated to such a temperature that the aerosol precursor composition may be atomized even if it does not contact the atomizer.

As noted above, the flexible circuit 1453 may be employed to establish a mechanical and electrical connection between a bubble jet head 1450 and an atomizer 1452 of a combined dispenser and atomizer assembly 1418. However, the flexible circuit 1453 may also be configured to electrically connect the combined dispenser and atomizer assembly 1418 and the power source 1410 in the cartridge through the coupler 1412 and the base 1416. In this regard, various other embodiments of combined dispensers and atomizer assemblies may be electrically connected to one or more other components of an aerosol delivery device via a flexible circuit.

For example, FIG. 15 illustrates a partial sectional view of an embodiment of an aerosol delivery device 1400' that is substantially similar to the aerosol delivery device 1400 of FIGS. 12-14. However, as illustrated, the aerosol delivery device 1400' of FIG. 15 may include a combined dispenser and atomizer assembly 1418' comprising a shared wafer, substrate, or housing 1433', in which both a bubble jet head and an atomizer are housed. In this regard, for example, the combined dispenser and atomizer assembly 1418' of FIG. 15 may be substantially similar to the combined dispenser and atomizer assembly 1318 of FIG. 9. In this embodiment, the flexible circuit 1453 may be employed to provide an electrical connection to the combined dispenser and atomizer assembly regardless of whether or not the bubble jet head and the atomizer are positioned within separate housings or a shared housing. Note also that usage of the combined dispenser and atomizer assembly 1418' including a bubble jet head and the atomizer within the shared housing 1433', through which air does not flow, may avoid any issues with respect to the liquid precursor composition being carried by the flow of air without atomization.

FIG. 16 illustrates a sectional view through an aerosol delivery device 1500 according to an additional example embodiment of the present disclosure. As illustrated, the aerosol delivery device 1500 may include a control body 1502 and a cartridge 1504, which are illustrated in a decoupled configuration. In this regard, a base 1516 of the cartridge 1504 may be configured to engage a coupler 1512 of the control body 1502 to form a mechanical and electrical connection therebetween, which may be releasable to allow for replacement of the cartridge.

The control body 1502 may include an end cap 1506, a circuit board with an indicator 1508 (e.g., a light emitting diode (LED)), a connector circuit 1509, an electrical power source 1510 (e.g., a battery, which may be rechargeable), a flow sensor 1511 (e.g., a puff sensor or pressure switch), the coupler 1512, wiring 1513, and an outer body 1514. The cartridge 1504 may include the base 1516, a combined dispenser and atomizer assembly 1518, a reservoir 1520, a mouthpiece 1524, an insulator 1555, and an outer body 1526. In the illustrated embodiment the coupler 1516 defines a lid 1522 that encloses the reservoir 1520. In this regard, by sealing shut an end of the reservoir 1520 with the coupler 1516, assembly of the cartridge 1504 may be simplified. However, in other embodiments the lid may comprise a component that is separate from the coupler.

FIG. 17 illustrates an enlarged partial sectional view of the aerosol delivery device 1500 wherein the control body 1502 and the cartridge 1504 are coupled to one another. As illustrated, the combined dispenser and atomizer assembly 1518 may comprise a bubble jet head 1550 and an atomizer 1552, which may be fixedly coupled to one another (e.g., by one or more spacers). The bubble jet head 1550 and the atomizer 1552 may comprise any of the components and features of the bubble jet heads and atomizers described elsewhere herein.

FIG. 17 further illustrates a flow path of air through the aerosol delivery device 1500 when a user draws on the mouthpiece 1524. As illustrated, an airflow or flow of ambient air 1528 may enter the aerosol delivery device 1500 through one or more inlet apertures 1531 which may be defined in the outer body 1514 of the control body 1502 and travel past or proximate the flow sensor 1511. The air 1528 may flow from the control body 1502 through at least one coupler aperture 1561 defined in the coupler 1512 and through one or more base apertures 1529 defined in the base 1516 of the cartridge 1504, around the reservoir 1520 (e.g., through one or more air delivery channels 1565 defined in the outer body 1526 or between the reservoir and the outer body), around and partially through the combined dispenser and atomizer assembly 1518, and out the mouthpiece 1524.

As a result of this configuration, some or all of the air 1528 may flow laterally across the cartridge 1504 through the combined dispenser and atomizer assembly 1518 between a bubble jet head 1550 and an atomizer 1552. When the flow sensor 1511 detects the puff, the combined dispenser and atomizer assembly 1518 may be activated such that the bubble jet head 1550 ejects the aerosol precursor composition from the reservoir 1520 toward the atomizer 1552.

Although the above-described configuration of the flow of at least part of the air 1528 through the combined dispenser and atomizer assembly 1518 may result in the aerosol precursor composition being ejected into the flow of air 1528 prior to atomization, usage of the one or more base apertures 1529 may regulate flow of the air through the combined dispenser and atomizer assembly such that substantially all of the aerosol precursor composition may come into contact with the atomizer 1552 (see, FIG. 13) and become atomized, rather than become entrained with the air in liquid form and thereafter potentially separate therefrom. Further, some of the air 1528 may flow around, rather than through, the combined dispenser and atomizer assembly 1518, such that the flow of the air may be distributed across a relatively large area and thereby the flow of the air through the combined dispenser and atomizer assembly may define a relatively low velocity which may not affect dispensing of the aerosol precursor composition onto the atomizer 1552 (see, FIG. 13) to a great extent. Further, as described above, one or more spacers and/or housings of the bubble jet head 1550 and the atomizer 1552 may define a vaporization chamber that further resists directing the aerosol precursor composition into the flow of air 1528 without being atomized and/or the atomizer may be positioned downstream of the bubble jet head to account for movement of the aerosol precursor composition caused by the flow of air. Following atomization, the air and vapor may travel around the reservoir 1522 and out the mouthpiece 1524 to the user.

Note that in the aerosol delivery devices 1200, 1300, 1400 of FIGS. 2-15 the reservoir is positioned between the mouthpiece and the combined dispenser and atomizer assembly, which may comprise a bubble jet head and an atomizer. This configuration may be desirable in that it positions the atomizer distally from the mouthpiece such that the user's mouth does not come into contact with a heated surface. In contrast, the combined dispenser and atomizer assembly 1518 of the aerosol delivery device 1500 of FIGS. 16 and 17 is positioned between the reservoir 1520 and the mouthpiece 1524. This configuration may be preferable in that the aerosol produced by the atomizer may only have to travel a relatively short distance to the mouthpiece 1524 such that the potential for the aerosol precursor composition to condense out of the air 1528 after vaporization is reduced. However, in order to keep the mouthpiece 1524 and/or the outer body 1526 cool to the touch at areas which a user may contact with his or her lips, the aerosol delivery device 1500 may further comprise an insulator 1555, as illustrated in FIG. 16. The insulator 1555 may comprise any embodiment of insulating materials such as plastic, fiberglass, or phenolic materials. Further, the insulator 1555 may be positioned proximate, or define, one or both of the outer body 1526 and the mouthpiece 1524 or a portion thereof.

FIG. 18 illustrates a sectional view through an aerosol delivery device 1600 according to an additional example embodiment of the present disclosure. As illustrated, the aerosol delivery device 1600 may include a control body 1602 and a cartridge 1604, which are illustrated in a coupled configuration. In this regard, a base 1616 of the cartridge 1604 may be configured to engage a coupler 1612 of the control body 1602 to form a mechanical and electrical connection therebetween, which may be releasable to allow for replacement of the cartridge.

The control body 1602 may include an end cap 1606, a circuit board with an indicator 1608 (e.g., a light emitting diode (LED)), a connector circuit 1609, an electrical power source 1610 (e.g., a battery, which may be rechargeable), a flow sensor 1611 (e.g., a puff sensor or pressure switch), the coupler 1612, wiring 1613, and an outer body 1614. The cartridge 1604 may include the base 1616, a combined dispenser and atomizer assembly 1618, a reservoir 1620, a mouthpiece 1624, and an outer body 1626. In the illustrated embodiment the coupler 1616 defines a lid 1622 that encloses the reservoir 1620. In this regard, by sealing shut an end of the reservoir 1620 with the coupler 1616, assembly of the cartridge 1604 may be simplified. However, in other embodiments the lid may comprise a component that is separate from the coupler.

FIG. 19 illustrates an enlarged partial sectional view of the aerosol delivery device 1600 wherein the control body 1602 and the cartridge 1604 are coupled to one another. As illustrated, the combined dispenser and atomizer assembly 1618 may comprise a bubble jet head 1650 and an atomizer 1652, which may be fixedly coupled to one another (e.g., by one or more spacers 1636). The bubble jet head 1650 and the atomizer 1652 may comprise any of the components and features of the bubble jet heads and atomizers described elsewhere herein.

As further illustrated in FIG. 18, outer body 1614 of the control body 1602 may define one or more inlet apertures 1631, the coupler 1612 may define at least one coupler aperture 1661, the base 1616, and may define at least one base aperture 1629, which may allow flow of air through the aerosol delivery device 1600. In this regard, FIG. 19 further illustrates a flow path of air through the aerosol delivery device 1600 when a user draws on the mouthpiece 1624. As illustrated, an airflow or flow of ambient air 1628 may enter the aerosol delivery device 1600 through the inlet apertures 1631, which may be defined in the outer body 1614 of the control body 1602, and travel past or proximate the flow sensor 1611. The air 1628 may flow from the control body 1602 through the coupler aperture 1661 defined in the coupler 1612 and through the base 1616 of the cartridge 1604 via the base aperture 1629, between the reservoir 1620 and the outer body 1626, around and partially through the combined dispenser and atomizer assembly 1618, and out the mouthpiece 1624. When the flow sensor 1611 detects the puff, the combined dispenser and atomizer assembly 1618 may be activated such that the bubble jet head 1650 ejects the aerosol precursor composition from the reservoir 1620 toward the atomizer 1652.

Although the above-described configuration of the flow of at least part of the air 1628 through the combined dispenser and atomizer assembly 1618 may result in the aerosol precursor composition being ejected into the flow of air 1628 prior to atomization, usage of the at least one base aperture 1629 may regulate flow of the air through the combined dispenser and atomizer assembly such that substantially all of the aerosol precursor composition may come into contact with the atomizer 1652 and become atomized, rather than become entrained with the air in liquid form and thereafter potentially separate therefrom. Further, some of the air 1628 may flow around, rather than through, the combined dispenser and atomizer assembly 1618, such that the flow of the air may be distributed across a relatively large area and thereby the flow of the air through the combined dispenser and atomizer assembly may define a relatively low velocity which may not affect dispensing of the aerosol precursor composition onto the atomizer 1652 to a great extent. Further, as described above, the spacers 1636 and/or housings of the bubble jet head 1650 and the atomizer 1652 may define a vaporization chamber that further resists directing the aerosol precursor composition into the flow of air 1628 without being atomized, and/or the atomizer may be positioned downstream from the bubble jet head to account for movement of the aerosol precursor composition caused by the flow of air. Following atomization, the air and vapor may travel around the reservoir 1620 and out the mouthpiece 1624 to the user.

As illustrated in FIGS. 18 and 19, the combined dispenser and atomizer assembly may be positioned proximate the mouthpiece 1624, which may provide benefits in terms of avoiding condensation of the vaporized aerosol precursor condensation within the aerosol delivery device as described above. An insulator may be employed proximate the mouthpiece in order to reduce the amount of heat transferred to a user's lips as further described above. As further illustrated in FIG. 19, in some embodiments the combined dispenser and atomizer assembly 1618 may be coupled to a lateral side 1655 of the reservoir 1620. This configuration may allow for substantially longitudinal flow through the combined dispenser and atomizer assembly 1618 and to the mouthpiece 1624. In this regard, a heating surface of the atomizer 1652 (e.g., comprising the outer surfaces of vaporization heating elements as described above) and an ejection surface of the bubble jet head 1650 (e.g., comprising the precursor nozzles) may be oriented substantially parallel to a longitudinal axis of the outer body 1626 of the cartridge 1604 and a longitudinal axis of the aerosol delivery device 1600 as a whole. Thereby, flow of the air 1628 may occur between parallel surfaces defined by the bubble jet head 1650 and the atomizer 1652 such that the flow of air and aerosol may proceed in a substantially linear manner to the mouthpiece 1624.

In contrast, the embodiments of aerosol delivery devices 1200, 1300, 1400, 1500 described above include embodiments of a combined dispenser and atomizer assembly attached to a distal end of the reservoir in a manner whereby the heating surface of the atomizer and the ejection surface of the bubble jet head are oriented substantially perpendicular to the outer body of the cartridge and a longitudinal axis of the aerosol delivery device as a whole. Although attaching the combined dispenser and atomizer assembly to the distal end of the reservoir provides for simplified construction of the aerosol delivery device, this configuration may result in a non-linear air flow path through the aerosol delivery device. For example, as illustrated in FIG. 14, the air may make one or more sharp turns entering and/or exiting the combined dispenser and atomizer assembly when the bubble jet head and the atomizer are oriented perpendicularly to a longitudinal axis of the aerosol delivery device. These sharp turns may undesirably increase the pressure drop associated with usage of the aerosol delivery device such that a draw thereon may require relatively greater effort. Further, sharp turns in the air flow path at or downstream of the combined dispenser and atomizer assembly may be detrimental in that such transitions may cause the aerosol to condense back into liquid form as a result of impacting surrounding structures within the aerosol delivery device (e.g., the outer body of the cartridge). Thus, usage of an air flow path that is generally oriented parallel to a longitudinal axis of the cartridge, and which does not include sharp turns may be desirable. In this regard, the aerosol delivery device 1600 illustrated in FIGS. 18 and 19 is configured to avoid the above-noted problems. However, it should also be noted that usage of bubble jet heads and atomizers oriented such that respective ejection and heating surfaces thereof are substantially perpendicular to a longitudinal axis of the cartridge, as described in the embodiments of aerosol delivery devices of FIGS. 2-17, may be desirable in that such a configuration may define a relatively slower airflow therethrough, such that atomization of the aerosol precursor composition may be improved.

Although the bubble jet head and the atomizer of the aerosol delivery device of FIGS. 18 and 19 are illustrated as being configured such that respective ejection and heating surfaces thereof are oriented substantially parallel to the longitudinal axis of the cartridge and the aerosol delivery device as a whole, certain embodiments of aerosol delivery devices including bubble jet heads and the atomizers in which respective ejection and heating surfaces are oriented at non-zero angles with respect to a longitudinal axis of the outer body may still provide many of the benefits described above with respect to the aerosol delivery device 1600 of FIGS. 18 and 19. In this regard, FIG. 20 illustrates a partial, schematic view of an aerosol delivery device 1700 including a combined dispenser and atomizer assembly 1718 wherein respective ejection and heating surfaces of a bubble jet head 1750 and an atomizer 1752 thereof are oriented at a non-zero angle with respect to a longitudinal axis 1770 of the aerosol delivery device. However, the angle between these surfaces and the longitudinal axis 1770 are relatively small (e.g., less than about 45 degrees), such that a pressure drop caused by the turns in a flow path of air 1728 before exiting a mouthpiece 1724 is reduced as compared to embodiments of aerosol delivery devices that are otherwise similar but define sharper turns in the flow path. Further, the relatively small angles between the ejection and heating surfaces of the bubble jet head 1750 and the atomizer 1752 and the longitudinal axis 1770 may also assist in avoiding issues with respect to condensation of the aerosol following vaporization and introduction into the flow of the air 1728, because the air and aerosol exiting the combined dispenser and atomizer assembly may smoothly exit therefrom without making a sharp turn.

FIG. 21 illustrates a sectional view through an aerosol delivery device 1800 according to an additional example embodiment of the present disclosure. As illustrated, the aerosol delivery device 1800 may include a control body 1802 and a cartridge 1804, which are illustrated in a coupled configuration. In this regard, a base 1816 of the cartridge 1804 may be configured to engage a coupler 1812 of the control body 1802 to form a mechanical and electrical connection therebetween, which may be releasable to allow for replacement of the cartridge.

The control body 1802 may include an end cap 1806, a circuit board with an indicator 1808 (e.g., a light emitting diode (LED)), a connector circuit 1809, an electrical power source 1810 (e.g., a battery, which may be rechargeable), a flow sensor 1811 (e.g., a puff sensor or pressure switch), the coupler 1812, wiring 1813, and an outer body 1814. The cartridge 1804 may include the base 1816, a combined dispenser and atomizer assembly 1818, a reservoir 1820, a mouthpiece 1824, and an outer body 1826. In the illustrated embodiment the coupler 1816 defines a lid 1822 that encloses the reservoir 1820. In this regard, by sealing shut an end of the reservoir 1820 with the coupler 1816, assembly of the cartridge 1804 may be simplified. However, in other embodiments the lid may comprise a component that is separate from the coupler.

FIG. 22 illustrates an enlarged partial sectional view of the aerosol delivery device 1800 wherein the control body 1802 and the cartridge 1804 are coupled to one another. As illustrated, the combined dispenser and atomizer assembly 1818 may comprise a bubble jet head 1850 and an atomizer 1852, which may be fixedly coupled to one another (e.g., by one or more spacers 1836). The bubble jet head 1850 and the atomizer 1852 may comprise any of the components and features of the bubble jet heads and atomizers described elsewhere herein.

FIGS. 21 and 22 further illustrate a flow path of air through the aerosol delivery device 1800 when a user draws on the mouthpiece 1824. As illustrated in FIG. 21, an airflow or flow of ambient air 1828 may enter the aerosol delivery device 1800 through one or more inlet apertures 1831 which may be defined in the outer body 1814 of the control body 1802 and travel past or proximate the flow sensor 1811. As illustrated in FIG. 22, the air 1828 may flow from the control body 1802 through a coupler inlet 1861 defined in the coupler 1812 and into the base 1816 of the cartridge 1804, through the reservoir 1820, through the combined dispenser and atomizer assembly 1818, and out the mouthpiece 1824.

In particular, the air 1828 may travel through the base 1816 via at least one base aperture 1829. Further, the reservoir 1820 may define a channel 1854 extending therethrough. In this regard, the reservoir 1820 may define an elongated annular configuration such that the aerosol precursor enclosed therein is separated from the channel 1854 (e.g., by an inner wall of the reservoir defining the channel). The channel 1854 may direct the flow of air 1828 to the combined dispenser and atomizer assembly 1818. In this regard, the bubble jet head 1850 may include an air flow aperture 1856 and the atomizer 1852 may include an aerosol delivery aperture 1858 configured to direct the flow of air 1828 therethrough. In the illustrated embodiment the base aperture 1829, the channel 1854 through the reservoir 1820, the air flow aperture 1856 through the bubble jet head 1850, and the aerosol delivery aperture 1858 through the atomizer 1852 are linearly arranged along a longitudinal axis extending through the cartridge 1804 such that the flow of air 1828 travels along a substantially linear path and thereby issues with respect to increasing a pressure drop of the aerosol delivery device 1800 and causing condensation may be averted. The aerosol delivery device 1800 may be further configured to avoid the production of condensation as a result of the combined dispenser and atomizer assembly 1818 being positioned between the reservoir 1820 and the mouthpiece 1824. As discussed above, an insulator may be employed to reduce heat transfer to the mouthpiece and the outer body.

FIG. 23 schematically illustrates an enlarged exploded view of the cartridge 1804 proximate the combined dispenser and atomizer assembly 1818. As illustrated, the reservoir 1820, the bubble jet head 1850, and the atomizer 1852 may be configured to dispense and atomize the aerosol precursor composition in a radial or an annular manner. In this regard, as schematically illustrated, the precursor inlets, precursor channels, ejection heating elements, and/or precursor nozzles of the bubble jet head 1850 may be positioned at a plurality of radial positions 1860 annularly about the air flow aperture 1856 extending through the bubble jet head. Similarly, a vaporization heating element 1862 of the atomizer 1852 may extend substantially radially and annularly about the aerosol delivery aperture 1858 extending through the atomizer. This configuration may allow for dispensing and atomizing of the aerosol precursor composition around, rather than in, the direct flow of air 1828 through the aerosol delivery device 1800, so as to avoid directing liquid aerosol precursor composition into the flow of air. This configuration may also facilitate the substantially linear flow of air 1828, to combine the benefits of the aerosol delivery devices described above.

In the embodiments of aerosol delivery devices described above, the atomizer has generally been described as defining a substantially planar heating surface at which the vaporization heating element(s) are positioned. In this regard, the bubble jet heads have defined an ejection surface on which the precursor nozzles are positioned that is also generally planar and parallel to the heating surface of the atomizer. Thereby, the bubble jet head has ejected the aerosol precursor composition substantially perpendicularly to the heating surface of the atomizer. However, various other configurations of atomizers may be employed.

For example, FIG. 24 illustrates an atomizer 1900 according to an alternate embodiment of the present disclosure. The atomizer 1900 may be employed in conjunction with any of the combined dispenser and atomizer assemblies discussed elsewhere herein. For example, the atomizer 1900 may be employed in place of the atomizer 1852 of the combined dispenser and atomizer assembly 1818 of the aerosol delivery device of FIGS. 21-23.

As illustrated, the atomizer 1900 may include an inner heating surface 1902 that is non-planar. In particular, the atomizer 1900 and the inner heating surface 1902 of the atomizer may be substantially conical (e.g., defining a hollow truncated conical configuration, as illustrated). In this regard, the atomizer 1900 may be configured to receive a flow of air and aerosol precursor composition 1904 therethrough, such that the inner heating surface 1902 of the atomizer receives the flow of air and aerosol precursor composition 1904 thereon.

Thereby, the heating surface 1902 may atomize the aerosol precursor composition. For example, a plurality of vaporization heating elements 1906 may be positioned on the inner heating surface 1902. By way of further example, in some embodiments the heating elements may be helically arranged on the inner heating surface 1902. This configuration may advantageously contact a majority of the aerosol precursor composition directed through the atomizer 1900. Thereby, a flow of air and aerosol 1908 may exit the atomizer 1900.

FIG. 25 illustrates an alternate embodiment of an atomizer 2000, which may be employed in place of the atomizer 1852 of the combined dispenser and atomizer assembly 1818 of the aerosol delivery device of FIGS. 21-23. The atomizer 2000 may include an outer heating surface 2002. As illustrated, the atomizer 2000 as a whole, in addition to the outer heating surface 2002, may define a substantially conical configuration. In this embodiment a flow of air and aerosol precursor composition 2004 may be directed toward a narrow end of the atomizer 2000. Thereby, the aerosol precursor composition may be vaporized by one or more vaporization heating elements 2006 positioned at the outer heating surface 2002 to produce a flow of air and aerosol 2008. The vaporization heating elements 2006 may be helically arranged on the outer heating surface 2002 in order to advantageously heat and vaporize the aerosol precursor composition.

Note also that although usage of multiple vaporization heating elements 1906, 2006 is generally discussed above, in other embodiments a single vaporization heating element may be employed. For example, the vaporization heating element may comprise a single, continuous embedded or printed filament at the heating surface. By way of further example, the single continuous filament may define a helical configuration (e.g., at the inner heating surface in the atomizer illustrated in FIG. 24 or at the outer heating surface in the atomizer illustrated in FIG. 25), as described above. Usage of a single continuous filament for the vaporization heating element may be preferable in that it may simplify construction of the atomizer.

Thus, in some embodiments a heating surface of an atomizer may define a non-planar configuration. Usage of an atomizer including a non-planar heating surface may allow for various alternate flow configurations through aerosol delivery devices. In particular, the substantially conical atomizers of FIGS. 24 and 25 may be respectively configured to focus or distribute air and aerosol while still providing for a substantially straight air flow path with a minimal increase in pressure drop associated with a puff on the aerosol delivery device. In these and other embodiments of combined dispenser and atomizers, the bubble jet head may direct the aerosol precursor composition at a non-perpendicular angle relative to the heating surface of the atomizer. By avoiding directing the aerosol precursor composition directly normal to the heating surface of the atomizer, issues with respect to aerosol precursor composition splattering may be avoided. In this regard, splattered aerosol precursor composition may deflect back toward the bubble jet head, which could cause the bubble jet head to clog. Further, in the embodiment of the atomizer 1900 of FIG. 24, any splattered aerosol precursor composition may be retained within the atomizer and contact another portion of the inner heating surface 1902, such that the splattered aerosol precursor still becomes vaporized due to the inner heating surface of the atomizer defining a chamber. Various other embodiments of frustoconical atomizers are described in U.S. patent application Ser. No. 14/329,334, filed Jul. 11, 2014, to Taluskie et al., which is incorporated herein by reference in its entirety.

FIG. 26 illustrates an exploded view of an alternate embodiment of a combined dispenser and atomizer assembly 2100 which may be included in embodiments of the aerosol delivery devices disclosed herein. As illustrated, the combined dispenser and atomizer assembly 2100 may include a bubble jet head 2102 and an atomizer 2104. Details with respect to embodiments of bubble jet heads are described above and will not be repeated in their entirety. Briefly, however, the bubble jet head 2102 may include a wafer, substrate, or housing 2106 which may define at least one precursor inlet 2108 (see, FIG. 27) configured to receive an aerosol precursor composition from a reservoir and at least one precursor nozzle 2110 configured to dispense the aerosol precursor composition to the atomizer 2104.

Further, the atomizer 2104 may comprise a wafer, substrate, or housing 2112. Additionally, as illustrated, in some embodiments the atomizer 2104 may further comprise a reinforcement member 2114. The reinforcement member 2114 may be configured to support the housing 2112 of the atomizer 2104 to provide structural stability thereto. For example, as illustrated in FIG. 27, the reinforcement member 2114 may be coupled to the housing 2112 of the atomizer 2104 such that the housing is supported. In particular, the reinforcement member 2114 may be coupled to a back of the housing 2112, wherein at least one vaporization heating element 2116 is coupled to the front of the housing, opposite thereto.

In this regard, the reinforcement member may be configured to provide stiffness, support, and structure to the atomizer 2014 without substantially increasing the thermal mass thereof. It may be desirable to provide the atomizer 2104 with a relatively low thermal mass such that the atomizer may rapidly heat to a temperature sufficient to vaporize the aerosol precursor composition when current is applied thereto. Thus, the atomizer 2104 may rapidly heat when a user draws on the associated aerosol delivery device.

By positioning the reinforcement member 2114 opposite from the vaporization heating element 2116, the reinforcement member may avoid direct contact with the heating element to reduce heat transfer to the reinforcement member. Further, as illustrated in FIG. 26, the reinforcement member 2114 may define a cutout 2118. The cutout 2118 may further reduce the thermal mass of the atomizer 2104 while still allowing the reinforcement member 2114 to provide the atomizer with improved strength. In this regard, the cutout may be centrally located such that the reinforcement member defines a frame extending around an outer edge of the housing 2112. This configuration results in only a relatively small loss in the moment of inertia of the reinforcement member 2114 while also positioning the mass thereof away from the vaporization heating element 2116 to further reduce heat transfer to the reinforcement member. Additionally, the reinforcement member 2114 may comprise plastic, ceramic, glass, or other embodiments of insulating and non-conductive materials that are configured to avoid heat and electrical transfer thereto.

As illustrated in FIG. 27, the atomizer 2104 may further comprise one or more conductive pads 2120. The conductive pads 2120 may be configured to contact the vaporization heating element 2116 to direct current thereto. However, in order to prevent the conductive pads 2120 from undesirably producing heat, the conductive pads may comprise a material and/or configuration (e.g., thicker gauge) that defines a lower resistance than a material of the vaporization heating element 2116. For example, the conductive pads 2120 may comprise silver palladium and the vaporization heating element 2116 may comprise platinum. By way of further example, in some embodiments the conductive pads 2120 may comprise silver palladium, and the vaporization heating element 2116 may comprise a silver palladium formulation defining a relatively greater resistance. However, as may be understood, various other materials may be employed in other embodiments including, for example, gold, silver, platinum, palladium, tungsten and combinations thereof. The materials defining the conductive pads and the vaporization heating element may be selected to define a desired resistance and appropriate bonding attributes with respect to the housing and/or other portions of the atomizer.

In some embodiments the atomizer 2104 may be configured to fixedly engage the bubble jet head 2102 via posts 2103 (see, FIG. 27). In this regard, as illustrated in FIG. 26, the housing 2112 and/or the reinforcement member 2114 may define recesses 2122a, 2122b configured to engage the posts 2103. In some embodiments the posts 2103 may electrically couple the bubble jet head 2102 to the atomizer 2104. Thus, for example, the conductive pads 2120 may be positioned proximate the recesses 2122a, 2122b defined in the atomizer 2104 such that an electrical connection may be established therebetween.

As noted above, it may be desirable to avoid splattering of an aerosol precursor composition dispensed onto an atomizer. Thus, embodiments of the aerosol delivery devices of the present disclosure may include additional or alternative features configured to mitigate splattering of the aerosol precursor composition and perform other functions. In this regard, FIGS. 28A-C illustrate enlarged partial views of embodiments of the atomizer 2104 of FIGS. 26 and 27 wherein the heating surface thereof is textured, rather than smooth. Note, however, that such texturing may be employed on any of the atomizers described herein.

In particular, FIG. 28A illustrates an embodiment of the atomizer 2104A wherein a heating surface 2124A is crenellated. In other words, the heating surface 2124A defines a substantially regular pattern of protrusions and recesses. FIG. 28B illustrates an embodiment of the atomizer 2104B wherein a heating surface 2124B is partially porous. In this regard, the topography of the heating surface 2124B may be substantially similar to that of a closed-cell foam. FIG. 28C illustrates an embodiment of the atomizer 2104C wherein a heating surface 2124C is fully porous. In this regard, the topography of the heating surface 2102C may be substantially similar to that of an open-celled foam or a sintered material.

In some embodiments the heating surface 2124A-C may be defined by, or coated with a passivation layer positioned at an outer surface thereof (e.g., on top of the housing 2112 and the vaporization heating element 2116. In this regard, the passivation layer is configured to prevent oxidation, catalytic reactions, and various other chemical reactions from occurring at the atomizer when an aerosol precursor composition 2128 is sprayed thereon. For example, the passivation layer may comprise aluminum oxide, glass, or a ceramic material, which may be sputtered or otherwise deposited over the vaporization heating elements 2116 and the housing 2112.

By employing a textured heating surface, the aerosol precursor composition may be less prone to splattering due to the textured heating surface capturing deflected aerosol precursor composition such that the aerosol precursor composition is less likely to deflect back to the bubble jet head. Further, usage of a textured heating surface may increase an effective area of the heating surface upon which the aerosol precursor composition is directed. Accordingly, heat may be more efficiently transferred to the aerosol precursor composition to improve vaporization of the aerosol precursor composition.

In some embodiments the heating surface may include a wicking or absorptive layer, which may optionally define the textured surface, and which may be configured to reduce splatter and heat loss and perform other functions as described hereinafter. The absorptive layer, which may comprise alumina paper in some embodiments, may be positioned outside of the passivation layer and may be configured to receive the aerosol precursor composition. Thereby, the aerosol precursor composition may saturate the absorptive layer, so that heat is applied to the aerosol precursor composition absorbed within this layer. In this embodiment the bubble jet head may replenish the aerosol precursor composition within the absorptive layer as it is vaporized. In this regard, the absorptive layer may be at least partially saturated with the aerosol precursor composition in advance of receiving a draw on the aerosol delivery device, such that aerosol may be produced more rapidly.

Note that although particular embodiments of atomizers are described above, various other embodiments of atomizers may be employed to vaporize the aerosol precursor composition in the embodiments of aerosol delivery devices provided herein. Such atomizers may include flat heaters, wound wire surfaces, micro heaters (e.g., embodied on a chip) glass plates, lasers, resistive heaters, and any other shape and embodiment of heater. For example, in one embodiment a vaporization heating element may be respectively associated with each precursor nozzle and each ejection heating element of the bubble jet head. However, in other embodiments multiple precursor nozzles and multiple ejection heating elements (e.g., all of the precursor nozzles and the ejection heating elements of the bubble jet head) may eject the aerosol precursor composition onto a single vaporization heating element to vaporize the aerosol precursor composition. Further, the materials employed in the ejection heating elements and the vaporization heating elements may vary. For example, the materials described above with respect to wire coil heating elements may be employed. Various other materials which may be employed in the ejection heating elements and the vaporization heating elements as well as the various other heating elements described herein may include platinum or a platinum-coated materials and resistive inks (e.g., printed on a ceramic material).

In another embodiment the housing for one or both of the bubble jet head and the atomizer may comprise a silicon chip. In this embodiment, one or both of the vaporization heating elements and the ejection heating elements may comprise the doped silicon of the silicon chip. In other words, part of the silicon chip may define a resistive circuit configured to produce heat to eject or vaporization the aerosol precursor composition.

In embodiments of aerosol delivery devices including a bubble jet head, it may be desirable to reduce the viscosity of the aerosol precursor composition to facilitate dispensing droplets of the aerosol precursor composition as discussed above. Accordingly, in one embodiment the aerosol precursor composition may be preheated. For example, the ejection heating elements may be employed to preheat the aerosol precursor composition prior to heating the aerosol precursor composition to an extent such that a bubble of vapor forms and a droplet of the aerosol precursor composition is ejected through a precursor nozzle. Such preheating may involve applying a pulsed current to the ejection heating elements. In this regard, a relatively smaller pulse width of power may be applied to the ejection heating elements of the bubble jet head during preheating the aerosol precursor composition as compared to a pulse width of the power applied to the ejection heating elements of the bubble jet head during dispensing of the aerosol precursor composition. In another embodiment the aerosol precursor composition may be diluted (e.g., with water) to decrease the viscosity thereof. Accordingly, use of the bubble jet head with an aerosol precursor composition may be facilitated in either or both of these manners. In one embodiment the viscosity of the aerosol precursor composition may initially define a range from about 5 to about 400 centipoise at 20 degrees Celsius. However, the viscosity of the aerosol precursor composition may be reduced through either or both of dilution (e.g., via water) or preheating to define a viscosity of less than about 100 centipoise at 20 degrees Celsius. In comparison, ink employed in inkjet printers may generally define a relatively lower viscosity (e.g., from about 10 to about 40 centipoise at 20 degrees Celsius).

In the embodiments provided herein, the combined dispenser and atomizer assembly has generally been described as being positioned in a cartridge. However, in another embodiment the bubble jet head and/or the atomizer may be positioned in the control body. For example, in one embodiment the bubble jet head may be positioned in the control body and configured to eject the aerosol precursor composition toward an atomizer in the cartridge. In this embodiment the aerosol precursor composition may be directed from a reservoir in the cartridge to the bubble jet head in the control body and back to the atomizer in the cartridge. In another embodiment the bubble jet head may be positioned in the cartridge and configured to eject the aerosol precursor composition from a reservoir in the cartridge toward an atomizer in the control body.

Further, FIG. 29 illustrates an alternate embodiment of an aerosol delivery device 2200 wherein a combined dispenser and atomizer assembly is positioned in the control body. As illustrated, the aerosol delivery device 2200 may include a control body 2202 and a cartridge 2204, which are illustrated in a decoupled configuration. In this regard, a base 2216 of the cartridge 2204 may be configured to engage a coupler 2212 of the control body 2202 to form a mechanical and electrical connection therebetween, which may be releasable to allow for replacement of the cartridge.

The control body 2202 may include an end cap 2206, a circuit board with an indicator 2208 (e.g., a light emitting diode (LED)), a connector circuit 2209, an electrical power source 2210 (e.g., a battery, which may be rechargeable), a flow sensor 2211 (e.g., a puff sensor or pressure switch), the coupler 2212, wiring 2213, a combined dispenser and atomizer assembly 2218, and an outer body 2214. In some embodiments the control body 2202 may further comprise a mounting plate 2219, and the combined dispenser and atomizer assembly 2218 may be mounted between the mounting plate and the coupler 2212. In the illustrated embodiment a bubble jet head 2250 of the combined dispenser and atomizer assembly 2218 may be coupled to the coupler 2212, an atomizer 2252 of the combined dispenser and atomizer assembly may be coupled to the mounting plate 2219, and the bubble jet head may be coupled to the atomizer via a flexible circuit 2253.

The cartridge 2204 may include the base 2216, a reservoir 2220, a lid 2222 that encloses the reservoir, a mouthpiece 2224, and an outer body 2226. When the cartridge 2204 is coupled to the control body 2202, the reservoir 2220 may be in fluid communication with the bubble jet head 2250. In this regard, the reservoir 2220 may define an outlet 2256. In some embodiments the base 2216 may also define an outlet 2258 that may align with the outlet 2256 to the reservoir 2220. One or both of the outlets 2256, 2258 may be initially sealed to retain an aerosol precursor composition in the reservoir 2220. In this regard, by way of example, a foil or plastic seal may cover the outlets 2256, 2258. However, the seal may be broken (e.g., by piercing the seal) when the base 2216 of the cartridge 2204 is engaged with the coupler 2212 of the control body 2202. Thereby, by positioning the bubble jet head 2250 in proximity to the coupler 2212, the bubble jet head may receive the aerosol precursor composition transferred from the reservoir 2220 through the outlets 2256, 2258 and through an inlet 2260 at the coupler. Thereby, the bubble jet head 2250 may dispense the aerosol precursor composition to the atomizer 2252 to produce an aerosol. A flow of air may enter through one or more inlet apertures 2262 in the outer body 2214 of the control body 2202 and travel through a mounting plate aperture 2261 defined in the mounting plate 2219 and through and/or around the combined dispenser and atomizer assembly 2218. The combined air and aerosol may thereby be directed through a coupler aperture 2267 defined in the coupler 2212, a base aperture 2263 defined in the base 2216, and through an aerosol delivery aperture 2265 defined in the outer body 2226 (or between the reservoir and the outer body) to the mouthpiece 2224.

Further, FIG. 30 illustrates an alternate embodiment of an aerosol delivery device 2300 wherein a combined dispenser and atomizer assembly is positioned in a separate dispenser and atomizer body. As illustrated, the aerosol delivery device 2200 may include a control body 2302, a dispenser and atomizer cartridge 2303, and a reservoir cartridge 2304, which are illustrated in a decoupled configuration. In this regard, a base 2316 of the reservoir cartridge 2304 may be configured to engage a coupler 2364 of the dispenser and atomizer cartridge 2303, and a base 2366 of the dispenser and atomizer cartridge may be configured to engage a coupler 2312 of the control body 2302 to form mechanical and electrical connections therebetween, which may be releasable to allow for replacement of the dispenser and atomizer cartridge and/or the reservoir cartridge.

The control body 2302 may include an end cap 2306, a circuit board with an indicator 2308 (e.g., a light emitting diode (LED)), a connector circuit 2309, an electrical power source 2310 (e.g., a battery, which may be rechargeable), a flow sensor 2311 (e.g., a puff sensor or pressure switch), the coupler 2312, and wiring 2313. The dispenser and atomizer cartridge 2303 may include an outer body 2371, the base 2366, the coupler 2364, and a combined dispenser and atomizer assembly 2318. As illustrated, in one embodiment the combined dispenser and atomizer assembly 2318 may be positioned between, and coupled to, the base 2366 and the coupler 2364. In particular, the combined dispenser and atomizer assembly 2318 may include a bubble jet head 2350 and an atomizer 2352, which may be connected via a flexible circuit 2353. In one embodiment the bubble jet head 2350 may be mounted to the coupler 2364 and the atomizer 2352 may be mounted to the base 2366 of the dispenser and atomizer cartridge 2303.

The reservoir cartridge 2304 may include the base 2316, a reservoir 2320, a lid 2322 that encloses the reservoir, a mouthpiece 2324, and an outer body 2326. When the reservoir cartridge 2304 is coupled to the dispenser and atomizer cartridge 2303, the reservoir 2320 may be in fluid communication with the bubble jet head 2350. In this regard, the reservoir 2320 may define an outlet 2356. In some embodiments the base 2316 of the reservoir cartridge 2304 may also define an outlet 2358 that may align with the outlet 2356 to the reservoir. One or both of the outlets 2356, 2358 may be initially sealed to retain an aerosol precursor composition in the reservoir 2320. In this regard, by way of example, a foil or plastic seal may cover the outlets 2356, 2358. However, the seal may be broken (e.g., by piercing the seal) when the base 2316 of the reservoir cartridge 2304 is engaged with the coupler 2364 of the dispenser and atomizer cartridge 2303. Thereby, by positioning the bubble jet head 2350 in proximity to the coupler 2364 of the dispenser and atomizer cartridge 2303, the bubble jet head may receive the aerosol precursor composition transferred from the reservoir 2320 through the outlets 2356, 2358 and through an inlet 2360 at the coupler of the dispenser and atomizer assembly. Thereby, the bubble jet head 2350 may dispense the aerosol precursor composition to the atomizer 2352 to produce an aerosol.

A flow of air may enter through one or more inlet apertures 2362 in the outer body 2314 of the control body 2302 and thereby be directed through at least one coupler aperture 2361 defined in the coupler 2312 of the control body, at least one base aperture 2363 defined in the base 2366 and through and/or around the aerosol dispenser and atomizer assembly 2318. The combined air and aerosol may then travel through a coupler aperture 2365 defined in the coupler 2364 of the dispenser and atomizer cartridge 2303, through a base aperture 2367 defined in the base 2316 of the reservoir cartridge 2304, through a vapor delivery aperture 2369 defined in the outer body 2326 of the reservoir cartridge (or between the reservoir and the outer body) to the mouthpiece 2324.

Accordingly, various alternative positional configurations may be employed for the components of the aerosol delivery devices discussed herein. As noted above, in one embodiment the combined dispenser and atomizer assembly may be positioned in the control body (see, e.g., FIG. 29). This configuration may be desirable in that the combined dispenser and atomizer assembly may have a usable life that exceeds that of the reservoir. However, in another embodiment the combined dispenser and atomizer assembly may be received in a separate dispenser and atomizer cartridge (see, e.g., FIG. 30). This configuration may be desirable in that although the combined dispenser and atomizer may have a usable life that exceeds that of the reservoir, the usable life of the combined dispenser and atomizer assembly may be less than that of the power source and other components of the control body, or vice versa. Further, this configuration may allow for substitution of alternate embodiments of combined dispensers and atomizer assemblies or control bodies to allow for customization of the aerosol delivery device to suit a user preferences (e.g., by employing a bubble jet head configured to produce a larger or smaller quantity of aerosol with each puff or by employing a control body with a larger battery).

In embodiments of aerosol delivery devices including a bubble jet head, the bubble jet head has generally been described as being fixedly coupled to the atomizer that vaporizes the aerosol precursor composition. For example, in one embodiment (see, e.g., FIGS. 2-6) the bubble jet head is coupled to the atomizer via spacers. In another embodiment (see, e.g., FIGS. 7-11), the bubble jet head is fixedly coupled to the atomizer via a shared housing. In an additional embodiment the bubble jet head is coupled to the atomizer via a flexible circuit and one or both of the atomizer and the bubble jet head is coupled to structure surrounding the combined dispenser and atomizer assembly (see, e.g., FIGS. 12-15). However, in another embodiment the bubble jet head may be decoupled from and aligned with the atomizer. Thereby, the space between the bubble jet head and the atomizer may be adjusted for the particular design of the bubble jet head, the viscosity of the aerosol precursor composition, and various other factors.

Further, in some embodiments the atomizer and/or the bubble jet head may be configured to perform a cleaning cycle (e.g., by producing heat to remove aerosol precursor composition residue therefrom) either automatically (e.g., after a specified number of users) or manually when so directed by a user. This may be particularly useful in embodiments in which the bubble jet head and/or the atomizer is positioned in the control body or a dispenser and atomizer cartridge and hence configured for reuse with multiple reservoirs.

The aerosol delivery devices described herein may avoid certain issues associated with conventional aerosol delivery devices that employ a wick to direct an aerosol precursor composition to an atomizer. In this regard, use of a wick may cause separation of the ingredients of an aerosol precursor composition. Further, use of a wick to transfer the aerosol precursor composition from a substrate to a heating element may result in leakage. Accordingly, the embodiments of the aerosol delivery devices disclosed herein may provide these and/or other advantages, including the advantages described above regarding greater control over the dispensed quantity of aerosol precursor composition. Additionally, the bubble jet heads and the atomizers described herein may require less energy to dispense and atomize an aerosol precursor composition than other embodiments of fluid delivery and vaporization mechanisms. Further, usage of a bubble jet head may allow for customization thereof (e.g., at the factory or by an end user). For example, the frequency and/or duration of dispensing by the bubble jet head may be adjusted to match a user's preferences. Thereby, for example, the aerosol delivery device may be configured to vaporize a relatively smaller or larger quantity of aerosol precursor composition with each puff on the aerosol delivery device, and such changes may be made without requiring a change in the hardware of the aerosol delivery device. In this regard, such changes may be implemented by software, or a change of electronic settings.

Note that while the aerosol delivery devices disclosed herein are generally described as including a cartridge (e.g., a replaceable cartridge) and a control body (e.g., a reusable control body), various other embodiments may be employed. For example, in other embodiments the aerosol delivery devices may include more than two-pieces, (e.g., as described above with reference to FIG. 30). In an additional embodiment the aerosol delivery device may define an integral, one-piece configuration. Thus, any of the aerosol delivery devices disclosed herein may be configured in any of a variety of manners in one or more outer bodies.

Various embodiments of atomizers and vaporization heating elements are described herein. As may be understood, various other embodiments of atomizers and vaporization heating elements may be employed in other embodiments. By way of example, in some embodiments the atomizer may comprise a coil heater, which may receive an aerosol precursor composition dispense by a bubble jet head.

Further, the particular configuration of the bubble jet head relative to the atomizer may vary. For example, in one embodiment a combined dispenser and atomizer assembly may include a housing with a first channel extending therethrough. The bubble jet head and the atomizer may be coupled to opposing sides of the first channel such that the bubble jet head may dispense an aerosol precursor composition onto the atomizer. For example, a second channel defined in the housing may supply the aerosol precursor composition to the bubble jet head. The resultant vapor may exit the housing via the first channel in which the bubble jet head and the atomizer are received.

In an additional embodiment, a method for aerosolization in an aerosol delivery device is provided. As illustrated in FIG. 31, the method may include directing an airflow from a control body comprising a power source through a cartridge comprising a reservoir at operation 2402. Further, the method may include dispensing an aerosol precursor composition from the reservoir via a bubble jet head at operation 2404. The method may additionally include heating the aerosol precursor composition dispensed from the reservoir by the bubble jet head with an atomizer at operation 2406.

In some embodiments of the method dispensing the aerosol precursor composition at operation 2404 and heating the aerosol precursor composition at operation 2406 comprise independently applying power from the power source to the bubble jet head and the atomizer. Further, dispensing the aerosol precursor composition at operation 2404 and heating the aerosol precursor composition at operation 2406 may comprise directing power to the atomizer after applying power to the bubble jet head. The method may further comprise preheating the aerosol precursor composition with the bubble jet head prior to dispensing the aerosol precursor composition at operation 2406. Additionally, the method may include detecting a temperature of the aerosol precursor composition, wherein preheating the aerosol precursor composition comprises preheating the aerosol precursor composition to a desired temperature. Preheating the aerosol precursor composition may comprise applying a relatively smaller pulse width of power to the bubble jet head as compared to dispensing the aerosol precursor composition.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. An aerosol delivery device, comprising:
   an outer body;
   a liquid reservoir within the outer body;
   an airflow path through at least a portion of the outer body; and
   a combined assembly comprising a bubble jet unit and a vaporization chamber defined in a substrate and positioned as the combined assembly within the outer body and configured to receive liquid from the liquid reservoir in a first portion of the combined assembly forming the bubble jet unit and dispense the liquid to a second portion of the combined assembly forming the vaporization chamber where the liquid is vaporized and provided into the airflow path; wherein the first portion defines at least two horizontal inlets, at least two liquid channels and the first portion includes one or more ejection elements positioned in each of the at least two liquid channels; wherein the first portion forms a divider positioned between and separating two liquid channels of the at least two liquid channels and, each horizontal inlet of the at least two horizontal inlets provides entry of the liquid into a respective liquid channel of the at least two liquid channels.

2. The aerosol delivery device of claim 1, wherein the combined assembly is coupled to the liquid reservoir.

3. The aerosol delivery device of claim 1, wherein the one or more ejectors are arranged to dispense the liquid to the second portion of the combined assembly as droplets.

4. The aerosol delivery device of claim 3, wherein the one or more ejectors comprise one or more heaters.

5. The aerosol delivery device of claim 3, wherein the combined assembly comprises one or more nozzles configured for passage of the droplets from the first portion to the second portion.

6. The aerosol delivery device of claim 1, wherein the positioning of the one or more ejectors in the at least two liquid channels is effective to both direct the liquid from the liquid reservoir through the at least two liquid channels and eject the liquid to the second portion of the combined assembly.

7. The aerosol delivery device of claim 1, wherein the second portion of the combined assembly comprises one or more vaporization elements positioned in the vaporization chamber, the one or more vaporization elements being configured to vaporize the liquid dispensed from the first portion of the combined assembly.

8. The aerosol delivery device of claim 7, wherein the one or more vaporization elements comprise one or more heating elements.

9. The aerosol delivery device of claim 1, wherein the combined assembly comprises one or more outlets from the vaporization chamber for exit of aerosol or vapor.

10. The aerosol delivery device of claim 1, wherein the combined assembly comprises one or more micro heaters.

11. The aerosol delivery device of claim 1, wherein the combined assembly is configured for electrical connection with a power source.

12. An aerosol delivery device, comprising:
    an outer body;
    a liquid reservoir within the outer body;
    an airflow path through at least a portion of the outer body; and
    a combined assembly comprising a bubble jet unit and a vaporization chamber defined in a substrate and positioned as the combined assembly within the outer body, the combined assembly comprising:
    a first portion including one or more liquid channels for passage of the liquid from the liquid reservoir and including one or more ejectors;
    a second portion including one or more vaporization elements;
    one or more nozzles opening from the first portion into the second portion; and
    one or more outlets from the second portion into the airflow path.

13. The aerosol delivery device of claim 12, wherein the combined assembly is coupled to the liquid reservoir.

14. The aerosol delivery device of claim 12, wherein the first portion of the combined assembly is the bubble jet unit.

15. The aerosol delivery device of claim 12, wherein the one or more ejectors comprise one or more heaters.

16. The aerosol delivery device of claim 12, wherein the one or more ejectors are positioned in the one or more liquid channels and are effective to both direct the liquid from the liquid reservoir through the one or more liquid channels and eject the liquid to the second portion of the combined assembly through the one or more nozzles.

17. The aerosol delivery device of claim 12, wherein the one or more ejectors are configured to dispense the liquid through the one or more nozzles as droplets.

18. The aerosol delivery device of claim 17, wherein the one or more vaporization elements are configured to vaporize the liquid droplets.

19. The aerosol delivery device of claim 12, wherein the one or more vaporization elements comprise one or more heating elements.

20. The aerosol delivery device of claim 12, wherein the combined assembly comprises one or more micro heaters.

21. The aerosol delivery device of claim 12, wherein the combined assembly is configured for electrical connection with a power source.

22. The aerosol delivery device of claim 12, wherein the one or more ejectors of the first portion of the combined assembly is axially aligned with a vaporization element of the second portion of the combined assembly.

* * * * *

UNITED STATES PATENT AND TRADEMARK OFFICE
CERTIFICATE OF CORRECTION

PATENT NO. : 12,128,179 B2
APPLICATION NO. : 17/895867
DATED : October 29, 2024
INVENTOR(S) : Brammer et al.

It is certified that error appears in the above-identified patent and that said Letters Patent is hereby corrected as shown below:

In the Claims

At Column 40, Claim 12, Lines 25 - 27, the text "a first portion including one or more liquid channels for passage of the liquid from the liquid reservoir and including one or more ejectors;" should be changed to -- a first portion defining at least two horizontal inlets, at least two liquid channels and the first portion includes one or more ejection elements, wherein the first portion forms a divider positioned between and separating two liquid channels of the at least two liquid channels, and each horizontal inlet of the at least two horizontal inlets provides entry of the liquid into a respective liquid channel of the at least two liquid channels; --

At Column 40, Claim 16, Line 42, the text "one or more liquid" should be changed to -- at least two liquid --

At Column 40, Claim 16, Line 44, the text "one or more liquid" should be changed to -- at least two liquid --

At Column 40, Claim 22, Line 64, the text "a vaporization element" should be changed to -- a vaporization element of the one or more vaporization elements --

Signed and Sealed this
Sixth Day of May, 2025

Coke Morgan Stewart
*Acting Director of the United States Patent and Trademark Office*